(12) United States Patent
Koya et al.

(10) Patent No.: US 7,763,658 B2
(45) Date of Patent: *Jul. 27, 2010

(54) TREATMENT FOR CANCERS

(75) Inventors: Keizo Koya, Chestnut Hill, MA (US);
Lijun Sun, Harvard, MA (US); Yaming Wu, Lexington, MA (US); Timothy Korbut, Brighton, MA (US); Dan Zhou, Lexington, MA (US); Zhenjian Du, Northborough, MA (US); Shoujun Chen, Bedford, MA (US); Noriaki Tatsuta, Lexington, MA (US); Guiqing Liang, Concord, MA (US); Mitsunori Ono, Lexington, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 1399 days.

This patent is subject to a terminal disclaimer.

(21) Appl. No.: 10/758,589

(22) Filed: Jan. 15, 2004

(65) Prior Publication Data
US 2004/0225016 A1    Nov. 11, 2004

Related U.S. Application Data

(60) Provisional application No. 60/440,406, filed on Jan. 15, 2003.

(51) Int. Cl.
*A61K 31/16* (2006.01)
(52) U.S. Cl. ........................ 514/599; 514/614
(58) Field of Classification Search ................. 514/599, 514/614
See application file for complete search history.

(56) References Cited

U.S. PATENT DOCUMENTS

| | | | |
|---|---|---|---|
| 4,012,360 A | 3/1977 | Schwarzenbach et al. | |
| 4,822,777 A | 4/1989 | Abra | |
| 5,498,421 A | 3/1996 | Grinstaff et al. | |
| 5,560,933 A | 10/1996 | Soon-Shiong et al. | |
| 5,665,382 A | 9/1997 | Grinstaff et al. | |
| 5,739,686 A | 4/1998 | Naughton et al. | |
| 5,840,746 A | 11/1998 | Ducharme et al. | |
| 5,916,596 A | 6/1999 | Desai et al. | |
| 6,013,836 A | 1/2000 | Hsu et al. | |
| 6,096,331 A | 8/2000 | Desai et al. | |
| 6,172,108 B1 | 1/2001 | Vega et al. | |
| 6,172,188 B1 | 1/2001 | Thastrup et al. | |
| 6,214,863 B1 | 4/2001 | Bissery et al. | |
| 6,235,787 B1 | 5/2001 | Broadhurst et al. | |
| 6,365,745 B1 | 4/2002 | Matsui et al. | |
| 6,399,659 B2 | 6/2002 | Usui et al. | |
| 6,435,787 B1 | 8/2002 | John | |
| 6,455,515 B2 | 9/2002 | Gypser et al. | |
| 6,506,405 B1 | 1/2003 | Desai et al. | |
| 6,537,579 B1 | 3/2003 | Desai et al. | |
| 6,656,971 B2 | 12/2003 | Wu et al. | |
| 6,703,426 B1 | 3/2004 | Miles et al. | |
| 6,749,868 B1 | 6/2004 | Desai et al. | |
| 6,753,006 B1 | 6/2004 | Desai et al. | |
| 6,762,204 B2 * | 7/2004 | Koya et al. | 514/599 |
| 6,800,660 B2 * | 10/2004 | Koya et al. | 514/614 |
| 6,825,235 B2 | 11/2004 | Chen et al. | |
| 6,924,312 B2 * | 8/2005 | Koya et al. | 514/614 |
| 7,001,923 B2 | 2/2006 | Koya et al. | |
| 7,037,940 B2 | 5/2006 | Koya et al. | |
| 7,074,952 B2 | 7/2006 | Chen et al. | |
| 7,250,432 B2 | 7/2007 | Kwon et al. | |

(Continued)

FOREIGN PATENT DOCUMENTS

AU    2006/228035 A1    11/2006

(Continued)

OTHER PUBLICATIONS

Goodman &Gilman's, The Pharmacological Basis of Therapeutics, Ninth Edition, (1996), Section X, Calabresi et al., pp. 1225-1232.*

(Continued)

*Primary Examiner*—Ardin Marschel
*Assistant Examiner*—James D Anderson
(74) *Attorney, Agent, or Firm*—Foley & Lardner LLP

(57) ABSTRACT

One embodiment of the present invention is a method of treating a subject with a multi-drug resistant cancer. The method comprises administering to the subject an effective amount of a compound represented by Structural Formula (I):

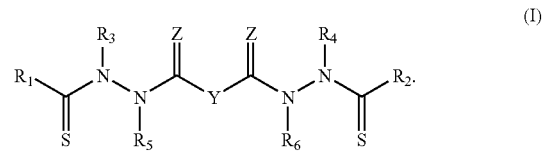

Y is a covalent bond or a substituted or unsubstituted straight chained hydrocarbyl group, or, Y, taken together with both >C=Z groups to which it is bonded, is a substituted or unsubstituted aromatic group.

$R_1$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring. Preferably $R_1$ and $R_2$ are the same and $R_3$ and $R_4$ are the same.

$R_5$-$R_6$ are independently —H, an aliphatic group, a substituted aliphatic group, an aryl group or a substituted aryl group.

Z is =O or =S.

6 Claims, 7 Drawing Sheets

U.S. PATENT DOCUMENTS

| | | | |
|---|---|---|---|
| 7,345,094 | B2 | 3/2008 | Koya et al. |
| 7,368,473 | B2 | 5/2008 | Koya et al. |
| 7,385,084 | B2* | 6/2008 | Koya et al. .................. 564/74 |
| 7,435,843 | B2 | 10/2008 | Chen et al. |
| 2002/0198160 | A1* | 12/2002 | Everitt et al. .................. 514/43 |
| 2003/0045518 | A1 | 3/2003 | Koya et al. |
| 2003/0119914 | A1 | 6/2003 | Koya et al. |
| 2003/0195258 | A1 | 10/2003 | Koya et al. |
| 2004/0022869 | A1 | 2/2004 | Chen et al. |
| 2004/0235813 | A1 | 11/2004 | Wanker et al. |
| 2005/0009920 | A1 | 1/2005 | Koya et al. |
| 2005/0154039 | A1 | 7/2005 | Glacera Contour et al. |
| 2006/0116374 | A1 | 6/2006 | Koya et al. |
| 2006/0122183 | A1 | 6/2006 | Koya et al. |
| 2006/0135595 | A1 | 6/2006 | Koya et al. |
| 2006/0142386 | A1 | 6/2006 | Barsoum |
| 2006/0142393 | A1 | 6/2006 | Sherman et al. |
| 2006/0167106 | A1 | 11/2006 | Zhang et al. |
| 2006/0270873 | A1 | 11/2006 | Chen et al. |
| 2006/0281811 | A1 | 12/2006 | Chen et al. |
| 2007/0088057 | A1 | 4/2007 | Lunsmann et al. |
| 2008/0089950 | A1 | 4/2008 | Chen et al. |
| 2008/0118562 | A1 | 5/2008 | Koya |
| 2008/0119440 | A1 | 5/2008 | Koya |
| 2008/0146842 | A1 | 6/2008 | Koya et al. |
| 2008/0176828 | A1 | 7/2008 | Koya et al. |
| 2008/0214655 | A1 | 9/2008 | Koya et al. |
| 2008/0226588 | A1 | 9/2008 | McLeod |
| 2008/0242702 | A1 | 10/2008 | Koya et al. |
| 2008/0269340 | A1 | 10/2008 | Koya et al. |
| 2009/0005594 | A1 | 1/2009 | Chen et al. |
| 2009/0042991 | A1 | 2/2009 | Barsoum et al. |

FOREIGN PATENT DOCUMENTS

| | | |
|---|---|---|
| DE | 2037257 | 2/1972 |
| EP | 1454628 A | 9/2004 |
| EP | 1493445 A | 1/2005 |
| EP | 1406869 B1 | 9/2006 |
| EP | 1 731 148 A | 12/2006 |
| FR | 2097737 | 4/1972 |
| GB | 1272920 | 5/1972 |
| JP | 50-91056 | 7/1975 |
| WO | WO 94/10995 | 5/1994 |
| WO | WO 99/34796 | 7/1999 |
| WO | WO 03/006428 A | 1/2003 |
| WO | WO 03/006429 A1 | 1/2003 |
| WO | WO 03/006430 A | 1/2003 |
| WO | WO 03/047524 A2 | 6/2003 |
| WO | WO 2004/072051 | 8/2004 |
| WO | WO 2005/028475 A2 | 3/2005 |
| WO | WO 2005/097758 A1 | 10/2005 |
| WO | WO 2006/009940 | 1/2006 |
| WO | WO 2006/033913 | 3/2006 |
| WO | WO 2006/055747 A2 | 5/2006 |
| WO | WO 2006/062732 A2 | 6/2006 |
| WO | WO 2006/089177 A2 | 8/2006 |
| WO | WO 2006/113493 | 10/2006 |
| WO | WO 2006/113572 | 10/2006 |
| WO | WO 2006/113695 | 10/2006 |
| WO | WO 2006/124736 | 11/2006 |
| WO | WO 2007/021881 A2 | 2/2007 |
| WO | WO 2007/139955 A2 | 12/2007 |
| WO | WO 2008/024298 A1 | 2/2008 |
| WO | WO 2008/024299 | 2/2008 |
| WO | WO 2008/024301 A2 | 2/2008 |
| WO | WO 2008/024302 A2 | 2/2008 |
| WO | WO 2008/024303 A2 | 2/2008 |
| WO | WO 2008/024305 A2 | 2/2008 |
| WO | WO 2008/027445 A2 | 3/2008 |
| WO | WO 2008/033300 A2 | 3/2008 |
| WO | WO 2008/033449 A2 | 3/2008 |
| WO | WO 2008/033494 A2 | 3/2008 |
| WO | WO 2008/082579 A1 | 7/2008 |
| WO | WO 2009/020631 A2 | 2/2009 |

OTHER PUBLICATIONS

Gura et al. Systems for identifying new drugs are often faulty. Science, 1997, 278:1041-1042.*

Johnson et al. Relationships between drug activity in NCI preclinical in vitro and in vivo models and early clinical trials. British J. of Cancer, 2001, 84(10):1424-1431.*

Sausville et al. Contributions of human tumor xenografts to anticancer drug development. Cancer Research, 2006, vol. 66, pp. 3351-3354.*

Chuyguk, V. A. and Nemazanyj A.G., "Mesoionic Methine Dyes from Biquaternary Salts of Dihetarylmethanes—1,3,4-Oxa(thia)diazoles and 1,2,4-Triazoles Derivatives," *Ukr. Khim. Zhurn.* 48:520 (1984). Translation submitted in U.S. Appl. No. 10/193,075, filed Jul. 10, 2002.

"Remarks" paper as submitted by applicant's attorney.

Stalteri, M.A., et al., "Site-specific conjugation and labelling of prostate antibody 7E11C5.3 (CYT-351) with technetium-99m," *European Journal of Nuclear Medicine* 24(6):651-654, (1997).

Twomey, D., "Anticancer Agents-IX. Derivatives of Pyridine, Pyridazine and Phthalazine," *Proceedings of the Royal Irish Academy*, vol. 74, Sect. B:37-52,(1974).

Barry, V. C. , et al., "Anticancer Agents-III. Synthesis and Anticancer Activity of Some Bis-Thiosemicarbazones and Thoiosemicarbazides," *Proc. R.I.A.* 65:309-324 1967).

O'Callaghan, C. N., "Anticancer Agents-X. Cyclisation of 1-Acyl-4-Alkylthiosemicarbazide Derivatives to 1,2,4-Triazoline-3-Thiones in the Presence of Hydrazine," *Proc. R.I.A.* 74:455-461 (1974).

Molina, P., et al., XP-01118868 "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles containing 1,3,4-Thiadiazole Subunits, X-Ray Crystal Structure of 2,2'-Bis[4,5-dihydro-5-(2-hydroxyethylimino)-4-methyl-1,3,4-thiadiazole]," *J. Chem. Soc. Perkin Trans. 1 s* 5:1159-1166 (1991).

Molina, P., et al., XP-001118802 "Preparation of a Novel Type of Ligands Incorporating Two or Three 1,3,4-Thiadiazole Units," *Heterocycles* 36(6):1263-1278 (1993).

H. Bräuniger, "Hydrazide und Hydrazidderivate von Dicarbonsäuren," Pharmaceutical-Chemical Institute of University of Rostock, Supplied by the "British Library" 25(5-6) 279-283 (1970).

Al-Talib, M. et al., "Diacyl Acid Dihydrazides," Magnetic Resonance in Chemistry 28:1072-1078 (1990).

Chuiguk, V.A., and Nemazanyi, A.G., "Mesoionic Methine Dyes Of Biquaternary Salts Of Diheteroaryl Methanes—Derivatives of 1, 3, 4—oxa (thia) diazoles and 1, 2, 4—Triazoles," Kiev. Gos. Univ., Kiev, USSR, Ukrainskii Khimicheskii Zhurnal, Russian Edition, 50(5):519-524 (1984). Abstract, Accession No. 1984:630420, HCAPLUS Database.

Barrett, William G. and McKay, Donald, "Decomposition and Cycloaddition Reactions of Some Bis(azodicarbonyl) Compounds," Journal of Chem. Soc. (4):1046-1052 (1975).

Mitsui Toatsu Chem. Inc., Abstract of Japanese Patent No. 308024, published Dec. 25, 1986. from Derwent Publications Ltd.

Honshu Paper Mfg. Co. Ltd, Abstract of Japanese Patent No. 182050, published Feb. 13, 1996.

Merlin, J.L., et al., In Vitro Comparative Evaluation of Trastuzumab (Herceptin®) Combined with Paclitaxel (Taxol®) or Docetaxel (Taxotere®) in HER2-Expressing Human Breast Cancer Cell Lines, *Annals of Oncology* 13: 1743-1748 (2002).

Asahi Chemical Ind. KK. Abstract of Japanese Patent No. 50-91056, Accession No. 47521Y/27 (1975).

"The Merck Manual," Chapter 14: Principles of Cancer Therapy, 1999 Merck Research Laboratories, pp. 987-995 (1999), XP002477370.

Abuchowski, A., et al., "Alteration of Immunological Properties of Bovine Serum Albumin by Covalent Attachment of Polyethylene Glycol," The *Journal of Biological Chemistry* 252(11):3578-3581 (1977).

Ashburner, M. and Bonner, J.J., "The Induction of Gene Activity in *Drosophila* by Heat Shock," *Cell*, 17: 241-254 (1979).

Auluck, P.K., et al., "Chaperone Suppression of α-Synuclein Toxicity in a *Drosophila* Model for Parkinson's Disease," *Science*, 295: 865-868 (2002).

Bahceci, et al., "Reactions of amidines with some carboxylic acid hydrazides," Indian Journal of Chemistry Section B, vol. 44B, 2005, pp. 568-572, XP009083365, p. 569, Scheme 1.

Balkwill, F. et al., "Inflammation and Cancer: Back to Virchow?" *The Lancet*, 357: 539-545 (Feb. 2001).

Barclay, J.W. and Roberson,R.M., "Role for Calcium in Heat Shock-Mediated Synaptic Thermoprotection in *Drosophila* Larvae," *J. Neurobiol.*, 56(4): 360-371 (2003).

Beck, F.-X., et al., "Molecular Chaperones in the Kidney: Distribution, Putative Roles, and Regulation," *Am. J. Physiol. Renal. Physiol..* 279: F203-F215 (2000).

Beillerot, et al., "Synthesis and protective effects of coumarin derivatives against oxidative stress induced by doxorubicin," Bioorganic & Medicinal Chemistry Letters, Oxford, GB, vol. 18, No. 3, Dec. 27, 2007, pp. 1102-1105, XP022475694, ISSN: 0960-894X.

Bellmann, K., et al., "Heat Shock Induces Resistance in Rat Pancreatic Islet Cells against Nitric Oxide, Oxygen Radicals and Streptozotocin Toxicity In Vitro," *J. Clin. Invest.*, 95(6): 2840-2845 (1995).

Berge, et al., "Pharmaceutical Salts," J. Pharm. Sci., 66 (1): 1-19, 1977.

Biagi, G. et al., "1,5-Diarylsubstituted 1,2,3-triazoles as Potassium Channel Activators. VI," *Il Farmaco*, 59(5): 397-404 (2004), esp. p. 398.

Blondeau, N., et al., "Polyunsaturated Fatty Acids Induce Ischemic and Epileptic Tolerance," *Neuroscience*, 109(2): 231-241 (2002).

Brittain et al., in *Polymorphism in Pharmaceutical Solids*, (NY: M. Dekker), vol. 95, pp. 348-361 (1999).

Cancer, Wikipedia, http://en.wikipedia.org/wiki/Cancer (1 of 40) Aug. 2, 2008 (all pages).

Carmel, J.B., et al., "Mediators of Ischemic Preconditioning Identified by Microarray Analysis of Rat Spinal Cord," *Exp. Neurol.*, 185: 81-96 (2004).

Carter, R. J., et al., "Characterization of Progressive Motor Deficits in Mice Transgenic for the Human Huntington's Disease Mutation," *J. Neuroscience*, 19(8): 3248-3257 (1999).

Chen, H-C., et al., Induction of Heat Shock Protein 70 Protects Mesangial Cells Against Oxidative Injury, *Kidney Int.*, 56: 1270-1273 (1999).

Clathrate: Lewis, Hawley's Condensed Chemical Dictionary, 14th Edition, 1997, Van Nostrand Reinhold.

Craig, E. A., "The Heat Shock," *Crit. Rev. Biochem.*, 18(3): 239-280 (1985).

Doi, Y., et al., "Effect of HSP70 Induced by Warm Ischemia to the Liver on Liver Function after Partial Hepatectomy," *Hepato-Gastroenterology*, 48: 533-540 (2001).

Dunn, S.E., et al., "Polystyrene-Poly (Ethylene Glycol) (PS-PEG2000) Particles as Model Systems for Site Specific Drug Delivery. 2. The Effect of PEG Surface Density on the in Vitro Cell Initeraction and in Vivo Biodistribution," *Pharmaceutical Research* 11(7):1016-1022 (1994).

Dvorak, H.F., et al., "Identification and Characterization of the Blood Vessels of Solid Tumors That Are Leaky to Circulating Macromolecules," *American Journal of Pathology* 133(1):95-109 (1988).

Gabizon, A.A., "Selective Tumor Localization and Improved Therapeutic Index of Anthracyclines Encapsulated in Long-Circulating Liposomes," *Cancer Research* 52:891-896 (1992).

Gao, Y., et al., "Protein Kinase C-dependent Activation of P44/42 Mitogen-activated Protein Kinase and Heat Shock Protein 70 in Signal Transduction During Hepatocyte Ischemic Preconditioning," *World J. Gastroenterol.*, 10(7): 1019-1027 (2004).

Garlock, K., "Experimental Treatment Gives a Cancer Patient Hope," *The Charlotte Observer* [online], Apr. 25, 2005 [retrieved on May 23, 2008]. Retrieved from the Internet URL: http://www.ericandfran.com/charlotte_observer_april_25.htm.

Gavezzotti, "Are crystal structures predictable?," Accounts of Chemical Research, 27:309-314, 1994.

Gawande, N.G., et al., "Synthesis of some thiosemicarbazides and related compounds," CAPLUS, 1989, XP002391517.

Gehrmann, M., "Drug Evaluation: STA-4783—Enhancing Taxane Efficacy by Induction of Hsp70," *Current Opinion in Investigational Drugs*, 7(6): 574-580 (Jun. 2006), XP008087326.

Georgopoulos, C. and Welch, W. J., "Role of the Major Heat Shock Proteins as Molecular Chaperones," *Annu. Rev. Cell Biol.*, 9: 601-634 (1993).

Golub et al., Science, vol. 286, 1999, pp. 531-537.

Gref, R., et al., "Biodegradable Long-Circulating Polymeric Nanospheres," *Science* 263:1600-1603 (1994).

Gurney, M. E., et al., "Motor Neuron Degeneration in Mice That Express a Human Cu,Zn Superoxide Dismutase Mutation," *Science*, 264: 1772-1775 (1994).

Hiratsuka, M., et al., "Heat Shock Pretreatment Protects Pulmonary Isografts from Subsequent Ischemia-reperfusion Injury," *J. Heart Lung Transplant*, 17(12): 1238-1246 (1998).

Holcomb, L., et al., "Accelerated Alzheimer-Type phenotype in transgenic mice carrying both mutant *amyloid precursor protein* and *presenilin 1* transgenes," *Nature Medicine*, 4(1): 97-100 (1998).

Howland, D. S., et al., "Focal Loss of the Glutamate Transporter Eaat2 in a Transgenetic Rat Model of Sod1 Mutant-mediated Amyotrophic Lateral Sclerosis (ALS)," *Proc. Nat. Acad. Sci. USA*, 99(3): 1604-1609 (2002).

Ichihara, et al., "Roles of oxidative stress and Akt signaling in doxorubicin cardiotoxicity," Biochemical and Biophysical Research Communications, Academic Press Inc., Orlando, FL, US, vol. 359, No. 1, Jun. 2, 2007, pp. 27-33, XP022103137, ISSN: 0006-291X.

Inclusion complex: Lewis, Hawley's Condensed Chemical Dictionary, 14th Edition, 1997, Van Nostrand Reinhold.

Ishii, Y., et al., "Retinal Ganglion Cell Protection with Geranylgeranylacetone, a Heat Shock Protein Inducer, in a Rat Glaucoma Model," *Invest. Opthalmol. Vis. Sci.*, 44(5): 1982-1992 (2003).

Jacquier-Sarlin, M.R. et al., "Protective Effects of hsp70 in Inflammation," *Experientia*, 50(11-12): 1031-1038 (Nov. 1994).

Johnson, A.D., el al., "Differential Distribution of 70-kD Heat Shock Protein Atherosclerosis," *Arterio Thromb Vasc Biol*, 15(1): 27-36 (1995).

Kandror, O. and Goldberg, A.L., "Trigger Factor is Induced Upon Cold Shock and Enhances Viability of *Escherichia coli* at Low Temperatures," *Proc Natl Acad Sci USA*, 94(10): 4978-4981 (1997).

Kelly, S. and Yenari, M.A., "Neuroprotection: Heat Shock Proteins," *Curr Res Med Opin*, 18(Suppl. 2): s55-s60 (2002).

Keswani, et al., "FK506 Is Neuroprotective in a Model of Antiretroviral Toxic Neuropathy," *Annals Neurology*, 53(1): 57-64 (2003).

Kiang, J.G. and Tsokos, G.C., "Heat Shock Protein 70 kDA: Molecular Biology, Biochemistry, and Physiology," *Pharmacol Ther*, 80(2): 183-201 (1998).

Klettner, A. and Herdegen, T., "The Immunophilin-Ligands FK506 and V-10,367 Mediate Neuroprotection by the Heat Shock Response," *Br J Pharmacol*, 138(5): 1004-1012 (2003).

Klettner, A., "The Induction of Heat Shock Proteins as a Potential Strategy to Treat Neurodegenerative Disorders," *Drug News Perspect*, 17(5): 299-306 (2004).

Klibanov, A., et al., "Amphipathic Polyethyleneglycols Effectively Prolong the Circulation Time of Liposomes," *FEBS* 268(1):235-237 (1990).

Langston, J.W., et al., "Selective Nigral Toxicity After Systemic Administration of 1-Methyl-4Phenyl-1,2,5,6-Tetrahydropyrine (MPTP) in the Squirrel Monkey," *Brain Res*, 292: 390-394 (1984).

Lee, J.E., et al., " Differential Neuroprotection From Human Heat Shock Protein 70 Overexpression in in Vitro and in Vivo Models of Ischemia and Ischemia-Like Conditions,"*Exp Neural*, 170(1): 129-139 (2001).

Lepore, D.A., et al., "Role of Priming Stresses and Hsp70 in Protection From Ischemia-Reperfusion Injury in Cardiac and Skeletal Muscle," *Cell Stress & Chaperones*, 6(2): 93-96 (2001).

Lindquist, S., "The Heat-Shock Response," *Ann Rev Biochem*, 55: 1151-1191 (1986).

Longa, E.Z., et al., "Reversible Middle Cerebral Artery Occlusion Without Craniectomy in Rats," *Stroke*, 20(1): 84-91 (1989).

Malberg, J.E. and Seiden, L.S., Poster "MDMA Administration Induces Expression of HSP70 in the Rat Brain." Society for Neuroscience Annual Meeting, New Orleans, LA, Oct. 25-30, 1997.

Mangiarini, L., et al. , "Exon 1 of the *HD* Gene With an Expanded CAG Repeat is Sufficient to Cause a Progressive Neurological Phenotype in Transgenic Mice," *Cell*, 87: 493-506 (1996).

Marber, M.S., et al., "Overexpression of the Rat Iducible 70-kD Heat Stree Protein in a Transgenic Mouse Increases the Resistance of the Heart to Ischemic Injury," *J Clin Invest*, 95: 1446-1456 (1995).

Milas, et al., "Chemoradiotherapy: emerging treatment improvement strategies," published online Dec. 6, 2003 in Wiley InterScience (www.interscience.wiley.com).

Minowada, G. and Welch, W.J., "Clinical Implications of the Stress Response," *J Clin Invest*, 95: 3-12 (1995).

Morimoto, et al., In: The Biology of Heat Shock Proteins and Molecular Chaperone. (NY: Cold Spring Harbor Laboratory Press) pp. 417-455 (1994).

Mosser, D.D., et al., "The Chaperone Function of hsp70 Is Required for Protecti Induced Apoptosis," *Mol Cell Biol*, 20(19): 7146-7159 (2000).

Papahadjopoulos, D., et al., "Sterically Stabilized Liposomes: Improvements in Pharmacokinetics and Antitumor Therapeutic Efficacy," *Proc. Natl. Acad. Sci. USA* 88:11460-11464 (1991).

Patani, et al., "Bioisosterism: A Rational Approach in Drug Design," Chem. Rev., 96: 3147-3176 (1996), esp. p. 3152.

Plumier, J.-C. L., et al., "Transgenic Mice Expressing the Human Heat Shock Protein 70 Have I proved Post-Ischemic Myocardial Recovery," *J Clin Invest*, 95: 1854-1860 (1995).

Radford, N.B., et al., "Cardioprotective Effects of 70-kDa Heat Shock Proteiin in Transgenic Mice," *Proc Natl Acad Sci USA*, 93(6): 2339-2342 (1996).

Rao et al., "Combination of Paclitaxel and Carboplatin as Second-Line Therapy for Patients with Metastatic Melanoma," *Cancer*, vol. 106, No. 2: 375-382 (2006).

Renshaw, G.M.C., et al., "Oxygen Sensors and Energy Sensors Act Synergistically to Achieve a Graded Alteration in Gene Expression: Consequences for Assessing the Level of Neuroprotection in Response to Stressors," *Front Biosci*, 9: 110-116 (2004).

Sanchez, et al., "New naphthylcombretastatins. Modifications on the ethylene bridge," Bioorganic and Medicinal Chemistry, vol. 13, No. 6, Mar. 2005, pp. 2097-2107, XP002470852, ISSN: 0968-0896.

Sato, K., et al., "HSP70 is Essential to the Neuroprotective Effect of Heat-Shock," *Brain Res*, 740(1-2): 117-123 (1996).

Sauer, H. and Oertel, W.H., "Progressive Degeneration of Nigrostriatal Dopamine Neurons Following Instrastriatal Terminal Lesions with 6-Hydroxydopamine: A Combined Retrograde Tracing and Immunocytochemical Study in the Rat," *Neuroscience*, 59(2): 401-415 (1994).

Savage, E., et al., Living with Melanoma, [online], [retrieved on Aug. 9, 2006]. Retrieved from the Internet URL: http://ericandfran.com/melanona.htm.

Shin, K.D., et al., "Blocking tumor cell migration and invasion with biphenyl isoxazole derivative KRIBB3, a synthetic molecule that inhibits Hsp27 phosphorylation" Journal of Biological Chemistry, American Society of Bioloechemical Biologists, Birmingham, US, vol. 280 No. 50, Oct. 18, 2005, pp. 41439-41448, XP002391924, ISSN: 0021-9258.

Simon, M.M., et al., "Heat Shock Protein 70 Overexpression Affects the Response to Ultraviolet Light in Murine Fibroblasts," *J Clin Res*, 95(3): 926-933 (1995).

Sobue, G., Molecular Pathogenesis of Motor Neuron Diseases (In Japanese) English abstract, *Nihon Shinkei Seishin Yakurigaku Zasshi*, 21(1): 21-25 (2001).

Tavaria, M. et al., "A Hitchhiker's Guide to the Human Hsp70 Family," *Cell Stress Chaperones*, 1(1): 23-28 (1996).

Todryk, S.M., et al. "Facets of Heat Shock Protein 70 Show Immunotherapeutic Potential,", *Immunology*, 110(1): 1-9 (2003).

Tsuchiya, D., et al., "Overexpression of Rat Heat Shock Protein 70 Reduces Neuronal injury After Transient Focal Ischemia, Transient Global Ischemia, or Kainic Acid-Induced Seizures," *Neurosurgery*, 53(5): 1179-1187 (2003).

Valeriote, F., et al. "Synergistic interaction of Anticancer Agents: A Cellular Perspective," *Cancer Chemotherapy Reports.*,59(5): 895-900 (1975).

Vippagunta, et al., "Crystalline solids," Advanced Drug Delivery Reviews, 48: 3-26, 2001.

Vleminckx, V., et al., "Upregulation of HSP27 in a Transgenic Model of ALS," *J Neuropathol Exp Neural*, 61(11): 968-974 (2002).

Voss, R.M., et al., "Gender Differences in the Expression of Heat Shock Proteins: The Effect of Estrogen," *Am J Physiol Heart Circ Physiol*, 285: H687-H692 (2003).

Wust, P. et al., "Hyperthermia in Combined Treatment of Cancer," *The Lancet Oncology*, 3(8): 487-497 (Aug. 2002), XP004813895.

Yenari, M.A., "Heat Shock Proteins and Neuroprotection," *Adv Exp Med Biol*, 513: 281-299 (2002).

Yu, Q., et al., "Retinal Uptake of Intravitreally Injected Hsc/Hsp70 and its Effect on Susceptibility to Light Damage," *Molecular Vision*, 7: 48-56 (2001).

Zhang, Y., et al., "Estrogen and Androgen Protection of Human Neurons Against Intracellular Amyloid $\beta_{1-42}$ Toxicity Through Heat Shock Protein 70," *J Neuroscience*, 24(23): 5315-5321 (2004).

Rupp, Walter, "5-Amino-1,3,4-Thiadiazole Compounds,"CA76:126992, 1972.

Schwarz et al., "Virustatic Thiosemicarbazides," CA77:48081, 1972.

\* cited by examiner

Compound (2)

Compound (3)

Compound (4)

Compound (5)

Compound (6) R = -OCH₃
Compound (7) R = -CN

Compound (8) R = -H
Compound (9) R = -CH₃

Compound (10)

Compound (11) R = -H
Compound (12) R = -CH₃

Compound (13)

Compound (14)

Compound (15)

Compound (16)

Compound (17)

Compound (18)

TREATMENT FOR CANCERS

RELATED APPLICATION

This application claims the benefit of U.S. Provisional Application No. 60/440,406 filed Jan. 15, 2003. The entire teachings of the above application are incorporated herein by reference.

BACKGROUND OF THE INVENTION

Many drugs are now available to be used in the treatment of cancer. However, in many cases the cancer either fails to respond to the anti-cancer therapy or its growth and spread is only slowed. Thus, there is still a need for new anti-cancer agents.

Even when a tumor initially responds to an anti-cancer therapy by decreasing in size or even going into remission, the tumor often develops resistance to the drug. Drug resistant tumors are characterized by a resumption of their growth and/or reappearance after having seemingly gone into remission, despite the administration of increased dosages of the anti-cancer drug.

For this reason, oncologists often administer combinations of anti-cancer drugs to a patient. Cancerous tumors are less likely to develop resistance when confronted with a multitude of different drugs, each having a different mode of action. Unfortunately, however, many tumors develop resistance, even when treated simultaneously with a number of different anti-cancer drugs. Cancers which reach this stage are referred to as "multi-drug resistant cancers", or simply "MDR cancers". There is little that can be done to halt or retard further progression of the disease, once a patient's cancer has become multi-drug resistant. Thus, there is an urgent need for new drugs which can be used to treat multi-drug resistant cancers.

SUMMARY OF THE INVENTION

It has now been found that certain bis[thio-hydrazide amide] compounds are significantly cytotoxic to cancer cells, including cancer cells that have become multi-drug resistant. For example, Compound (1) had an $IC_{50}$ of 0.005, 0.05 and 0.01 µM against the multi-drug resistant cell lines MES-SA/DX5, HL-60/TX1000 and Bowes/OV2, respectively (see Example 15). The $IC_{50}$ for the anticancer drugs Paclitaxel and vincristine was two to three orders of magnitude larger for the same cell lines (see Example 15). The structure of Compound (1) is shown below:

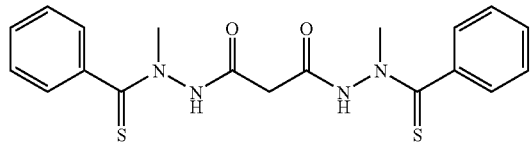

Compound (1)

In addition, the $IC_{50}$ for bis[thio-hydrazide amide] Compounds (2)-(18) ranged from 0.05 to 0.005 µM against MES-SA/DX5 (see Example 16). The structures of Compounds (2)-(18) are provided in FIG. 1. Moreover, the size of multi-drug resistant MES-SA/DX5 tumors in nude mice treated with bis[thio-hydrazide amide] Compound (16) was significantly reduced compared with tumors in mice treated only with vehicle (see Example 17). The structure of Compound (16) is shown below:

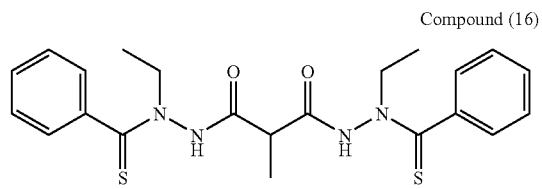

Compound (16)

It has also been found that the disclosed compounds enhance the anti-cancer activity of other anti-cancer agents, such as Epothilone D (Example 18). Based on these results, methods of treating a subject with a cancer, including cancers that have become multi-drug resistant are disclosed herein.

One embodiment of the present invention is a method of treating a subject with a multi-drug resistant cancer. The method comprises administering to the subject an effective amount of a compound represented by Structural Formula (I):

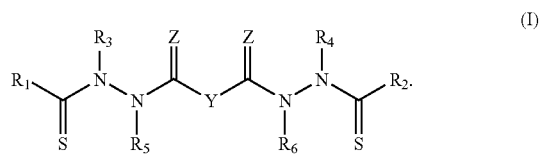

(I)

Y is a covalent bond or a substituted or unsubstituted straight chained hydrocarbyl group, or, Y, taken together with both >C=Z groups to which it is bonded, is a substituted or unsubstituted aromatic group. Preferably, Y is a covalent bond or —C($R_7R_8$)—.

$R_1$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring. Preferably $R_1$ and $R_2$ are the same and $R_3$ and $R_4$ are the same.

$R_5$-$R_6$ are independently —H, an aliphatic group, a substituted aliphatic group, an aryl group or a substituted aryl group. Preferably, $R_5$ and $R_6$ are the same.

$R_7$ and $R_8$ are each independently —H, an aliphatic or substituted aliphatic group, or $R_7$ is —H and $R_8$ is a substituted or unsubstituted aryl group, or, $R_7$ and $R_8$, taken together, are a C2-C6 substituted or unsubstituted alkylene group.

Z is =O or =S.

Another embodiment of the present invention is a method of treating a subject with cancer. The method comprising administering to the subject an effective amount of a compound represented by Structural Formula (I). The compound represented by Structural Formula (I) is administered as a monotherapy (i.e., as the only anti-cancer drug administered to the subject). Optionally a second anti-cancer agent is co-administered to the subject, provided that the second anti-cancer agent is other than Paclitaxel or an analog of Paclitaxel. When the subject is a mouse, then the compound is other than:

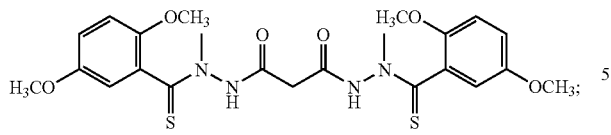

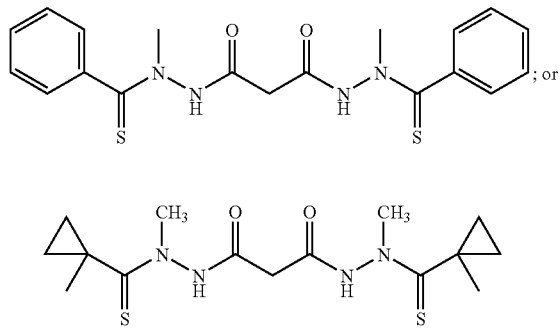

Therefore, the method is commonly used with subjects other than mice. Preferably, the subject is a human subject.

The disclosed method can often be used to treat cancers, including cancers that have become multi-drug resistant. Thus, the disclosed methods can often be used to treat cancers where other drug regimens have either failed or become ineffective. Because the compounds used in the method are relatively non-toxic, they cause minimal side effects and can used at relatively high doses.

DETAILED DESCRIPTION OF THE INVENTION

Figure 1A:
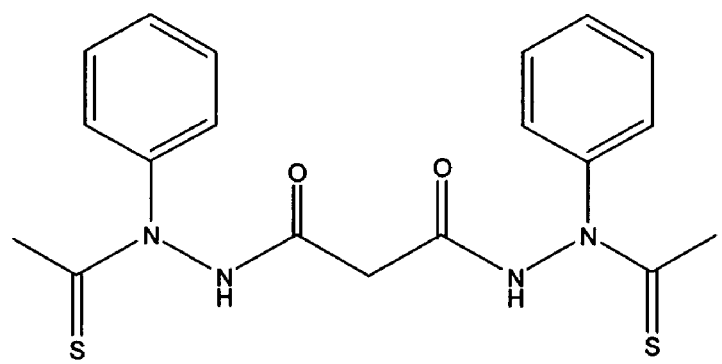
FIGS. 1A-1D are a list of structures of Compounds (2)-(18) that are exemplified with the disclosed method.
Figure 1A:
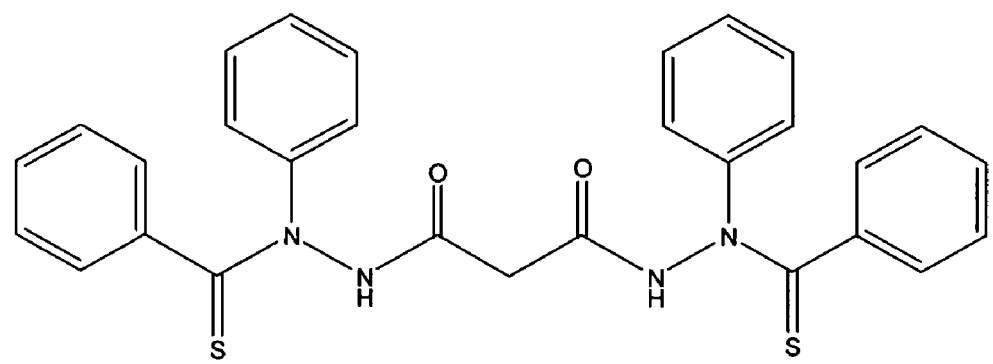
Figure 1A:
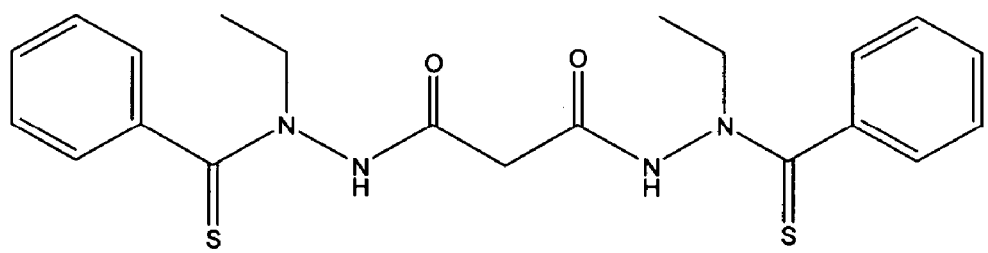
Figure 1A:
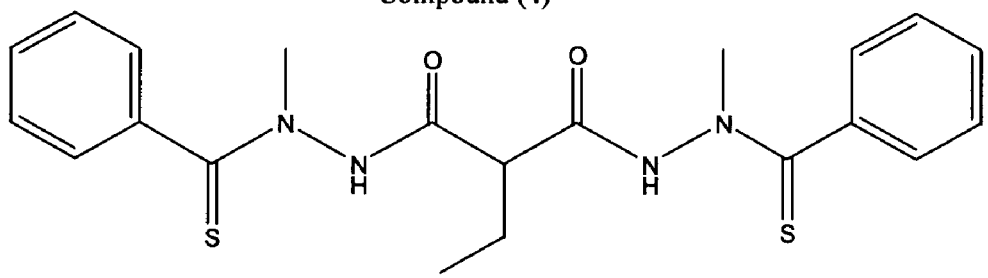
Figure 1B:
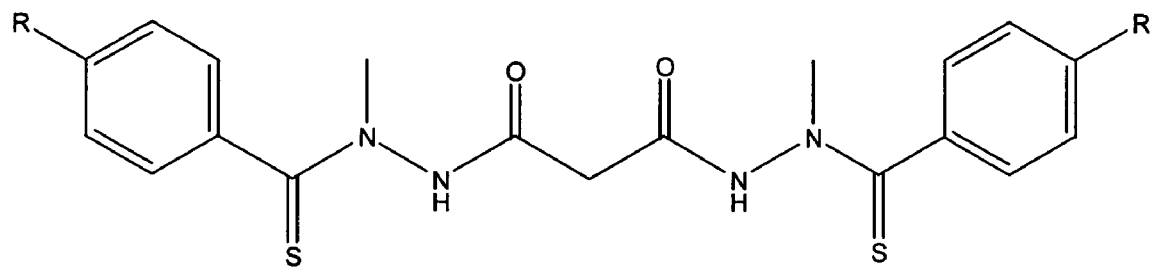
Figure 1B:
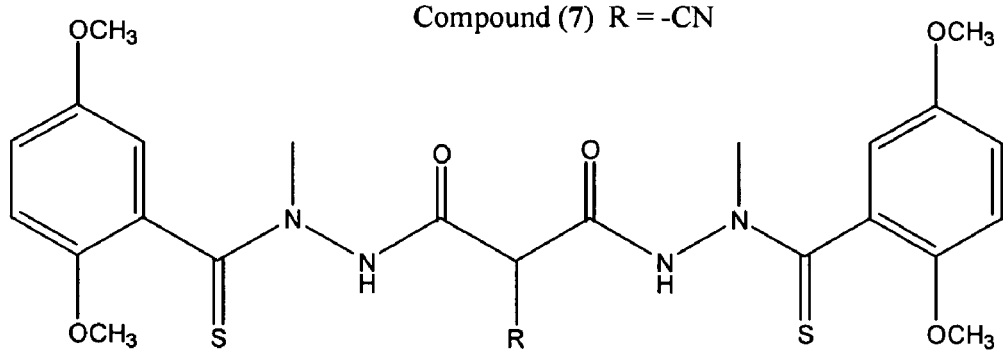
Figure 1B:
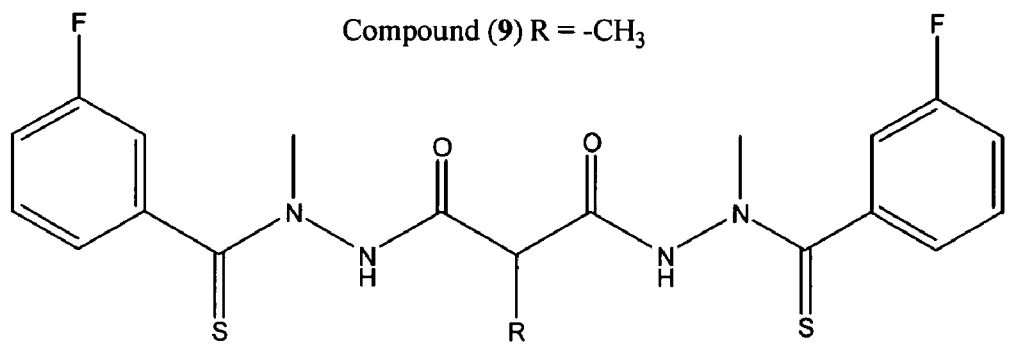
Figure 1C:
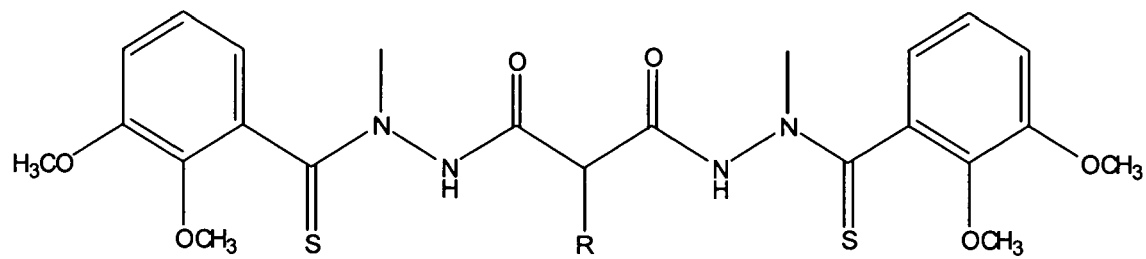
Figure 1C:
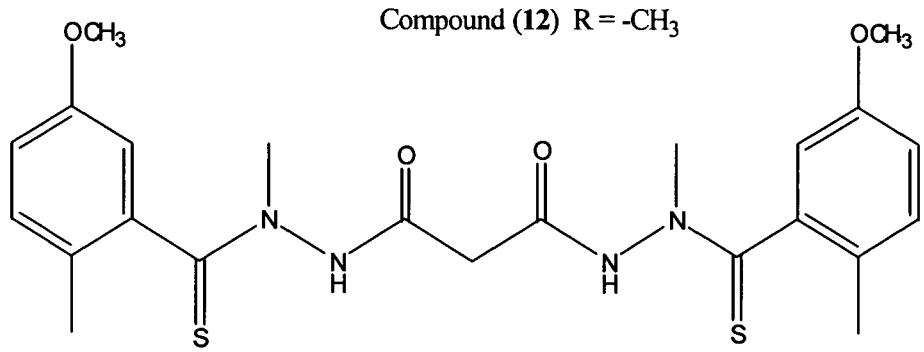
Figure 1C:
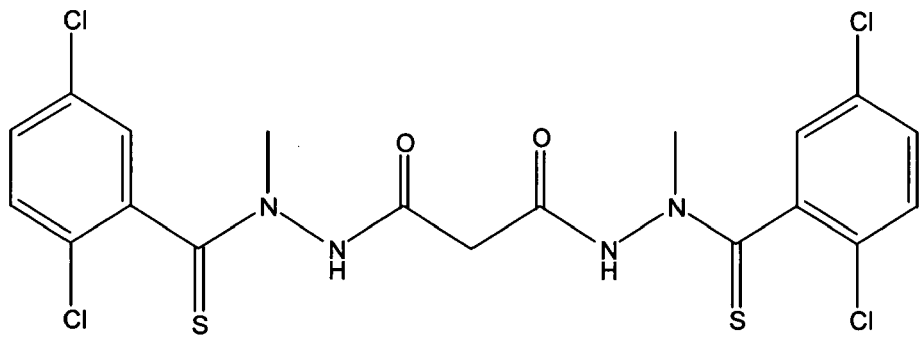
Figure 1D:
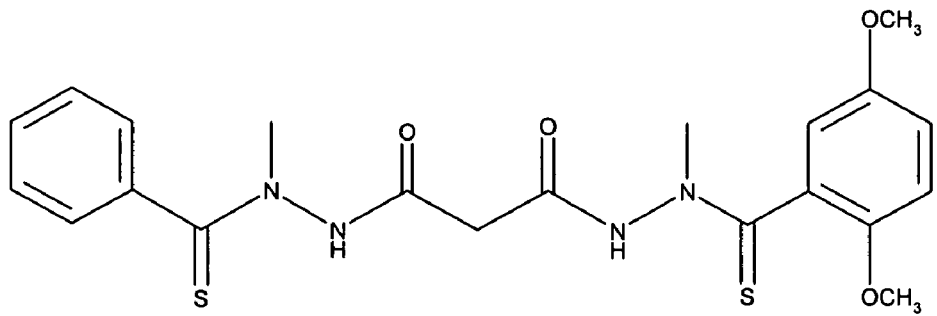
Figure 1D:
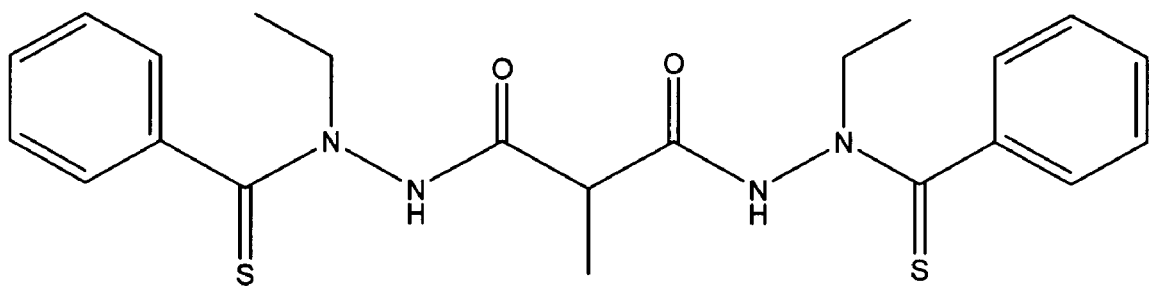
Figure 1D:
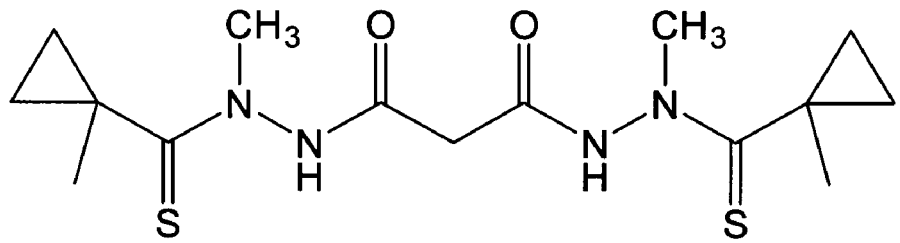
Figure 1D:
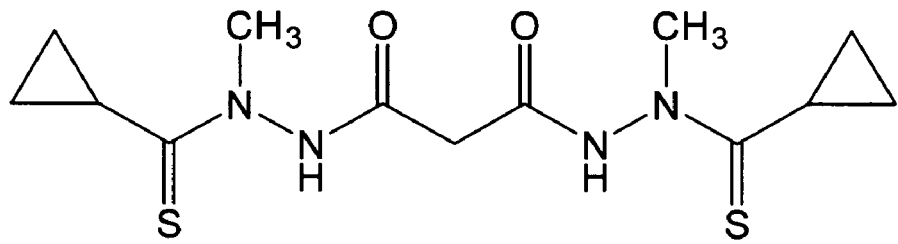

In a first preferred embodiment, Y in Structural Formula (I), taken together with both >C=Z groups to which it is bonded, is a substituted or unsubstituted arylene group and the compound is represented by Structural Formula (II):

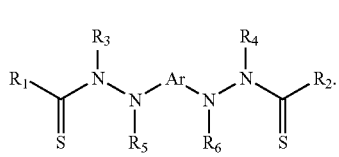

$R_1$-$R_6$ in Structural Formula (II) are as described in Structural Formula (I). Ar is a substituted or unsubstituted arylene group. Preferably, Ar is a nitrogen-containing heteroarylene group. Examples are shown below:

Ring A is substituted or unsubstituted.

In a second preferred embodiment, Y in Structural Formula (I) is a covalent bond, a substituted or unsubstituted straight chained hydrocarbyl group or a phenylene group. Preferably, Y is a covalent bond, —C($R_7R_8$)—, —(CH$_2$CH$_2$)—, trans-(CH=CH)—, cis-(CH=CH)—, —(CC)— or a 1,4-phenylene group. $R_7$ and $R_8$ are as described for Structural Formula (I). Even more preferably, Y is a covalent bond or —C($R_7R_8$)—.

In a more preferred embodiment, Y in Structural Formula (I) is a covalent bond or —C($R_7R_8$)— and the compound used in the method of the present invention is represented by Structural Formula (III):

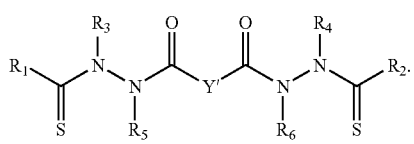

$R_1$-$R_6$ are as described for Structural Formula (I). Y' is a covalent bond or —C($R_7R_8$)—; and $R_7$ and $R_8$ can be the same or different and are: i) each independently —H, an aliphatic or substituted aliphatic group (preferably alkyl, more preferably methyl); ii) $R_7$ is —H and $R_8$ is a substituted or unsubstituted aliphatic group (preferably alkyl, more preferably methyl) or a substituted or unsubstituted aryl group (preferably thienyl, substituted thienyl, phenyl substituted phenyl, benzyl or substituted benzyl); or iii) $R_7$ and $R_8$, taken together, are a C2-C6 substituted or unsubstituted alkylene group (preferably propylene or butylene).

In an even more preferred embodiment, the compound used in the method of the present invention is represented by Structural Formula (IV):

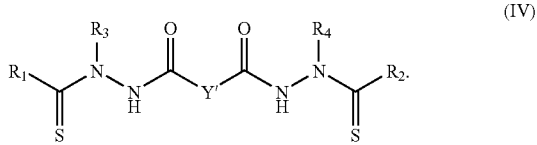

In the compound represented by Structural Formula (IV), Y' is a covalent bond or —C($R_7R_8$)— and $R_1$-$R_4$ and $R_7$-$R_8$ are as described for Structural Formula (I).

In a first example of a compound represented by Structural Formula (IV), $R_1$ and $R_2$ are each a substituted or unsubstituted aryl group; $R_3$ and $R_4$ are each a substituted or unsubstituted aliphatic group; $R_7$ is —H; and $R_8$ is —H, an aliphatic or substituted aliphatic group. Preferably in the compound represented by Structural Formula (IV), $R_1$ and $R_2$ are each a substituted or unsubstituted aryl group; $R_3$ and $R_4$ are each an alkyl group; and $R_7$ is —H and $R_8$ is —H or methyl. Even more preferably, in the compound represented by Structural Formula (IV), $R_1$ and $R_2$ are each a substituted or unsubstituted phenyl group; $R_3$ and $R_4$ are each methyl or ethyl; and $R_7$ is —H and $R_8$ is —H or methyl. Suitable substituents for an aryl group represented by $R_1$ and $R_2$ and an aliphatic group represented by $R_3$, $R_4$ and $R_8$ are as described below for aryl and aliphatic groups.

In a second example of a compound represented by Structural Formula (IV), $R_1$ and $R_2$ are both phenyl or substituted phenyl, $R_3$ and $R_4$ are both methyl, ethyl, phenyl, or thienyl, and $R_7$ and $R_8$ are as described in the first example of a compound represented by Structural Formula (IV). When $R_1$ and $R_2$ are both phenyl or substituted phenyl and $R_3$ and $R_4$ are both methyl, ethyl, phenyl, or thienyl, then preferably $R_7$ and $R_8$, taken together, are propylene or butylene.

In a third example of a compound represented by Structural Formula (IV), $R_1$ and $R_2$ are both an aliphatic group or a substituted aliphatic group (preferably substituted or unsubstituted alkyl group, including a substituted or unsubstituted cycloalkyl group such as a substituted or unsubstituted cyclopropyl group); $R_3$ and $R_4$ are both an aryl group or a substituted aryl group, and $R_7$ and $R_8$ are as described the first example of a compound represented by Structural Formula (IV).

In another example of a compound represented by Structural Formula (IV), $R_1$ and $R_2$ are both substituted or unsubstituted aliphatic groups, $R_3$ and $R_4$ are both a lower alkyl group or a substituted lower alkyl group, and $R_7$ and $R_8$ are as described in the first example of a compound represented by Structural Formula (IV); preferably, $R_1$ and $R_2$ are both substituted or unsubstituted alkyl groups (more preferably substituted or unsubstituted cycloalkyl groups), $R_3$ and $R_4$ are both —H, methyl or ethyl, $R_7$ is —H and $R_8$ is —H or methyl.

In yet another example of a compound represented by Structural Formula (IV), $R_1$ and $R_2$ are both C3-C8 cycloalkyl or substituted C3-C8 cycloalkyl and $R_3$ and $R_4$ are both methyl, ethyl, phenyl, or thienyl, and $R_7$ and $R_8$ are as described the first example of a compound represented by Structural Formula (IV) (preferably, $R_7$ and $R_8$ are: 1) both methyl; 2) taken together, are propylene or butylene; or 3) $R_7$ is —H and $R_8$ is lower alkyl, thienyl, phenyl or benzyl).

In yet another example of a compound represented by Structural Formula (IV), $R_1$ and $R_2$ are both a lower alkyl group or a substituted lower alkyl group, $R_3$ and $R_4$ are both methyl, ethyl or phenyl, and $R_7$ and $R_8$ are as described the first example of a compound represented by Structural Formula (IV).

The following are specific examples of compounds represented by Structural Formula (IV): $R_1$ and $R_2$ are both phenyl; $R_3$ and $R_4$ are both methyl; $R_7$ is —H, and $R_8$ is ethyl; $R_1$ and $R_2$ are both phenyl; $R_3$ and $R_4$ are both phenyl, and $R_7$ and $R_8$ are both methyl; $R_1$ and $R_2$ are both 2-thienyl; $R_3$ and $R_4$ are both phenyl, and $R_7$ and $R_8$ are both methyl; $R_1$ and $R_2$ are both 4-cyanophenyl; $R_3$ and $R_4$ are both methyl; $R_7$ is —H, and $R_8$ is methyl; $R_1$ and $R_2$ are both phenyl; $R_3$ and $R_4$ are both methyl; $R_7$ is —H, and $R_8$ is methyl; $R_1$ and $R_2$ are both phenyl; $R_3$ and $R_4$ are both methyl; $R_7$ is —H, and $R_8$ is benzyl; $R_1$ and $R_2$ are both phenyl; $R_3$ and $R_4$ are both methyl; $R_7$ is —H, and $R_8$ is ethyl; $R_1$ and $R_2$ are both phenyl; $R_3$ and $R_4$ are both ethyl; $R_7$ is —H, and $R_8$ is n-butyl; $R_1$ and $R_2$ are both 2,5-dimethoxyphenyl; $R_3$ and $R_4$ are both methyl; $R_7$ is —H, and $R_8$ is methyl; $R_1$ and $R_2$ are both phenyl; $R_3$ and $R_4$ are both methyl; $R_7$ is —H, and $R_8$ is iso-propyl; $R_1$ and $R_2$ are both 3-nitrophenyl; $R_3$ and $R_4$ are both methyl; $R_7$ is —H, and $R_8$ is methyl; $R_1$ and $R_2$ are both 4-chlorophenyl; $R_3$ and $R_4$ are both methyl; $R_7$ is —H, and $R_8$ is methyl; $R_1$ and $R_2$ are both phenyl; $R_3$ and $R_4$ are both methyl; $R_7$ is —H, and $R_8$ is 3-thienyl; $R_1$ and $R_2$ are both phenyl; $R_3$ and $R_4$ are both methyl, and $R_7$ and $R_8$, taken together, are propylene; $R_1$ and $R_2$ are both 2,3-dimethoxyphenyl; $R_3$ and $R_4$ are both methyl; $R_7$ is —H, and $R_8$ is methyl; $R_1$ and $R_2$ are both 2-chloro-5-methoxy phenyl; $R_3$ and $R_4$ are both methyl; $R_7$ is —H, and $R_8$ is methyl; $R_1$ and $R_2$ are both 2,5-difluorophenyl; $R_3$ and $R_4$ are both methyl; $R_7$ is —H, and $R_8$ is methyl; $R_1$ and $R_2$ are both 2,5-dichlorophenyl; $R_3$ and $R_4$ are both methyl; $R_7$ is —H, and $R_8$ is methyl; $R_1$ and $R_2$ are both 2,6-dimethoxyphenyl; $R_3$ and $R_4$ are both methyl; $R_7$ is —H, and $R_8$ is methyl; $R_1$ and $R_2$ are both 2,5-dimethylphenyl; $R_3$ and $R_4$ are both methyl; $R_7$ is —H, and $R_8$ is methyl; $R_1$ and $R_2$ are both 2,5-dimethoxyphenyl; $R_3$ and $R_4$ are both ethyl; $R_7$ is —H, and $R_8$ is methyl, and $R_1$ and $R_2$ are both 2,5-diethoxyphenyl; $R_3$ and $R_4$ are both methyl; $R_7$ is —H, and $R_8$ is methyl; $R_1$ and $R_2$ are both cyclopropyl; $R_3$ and $R_4$ are both methyl; $R_7$ and $R_8$ are both —H; $R_1$ and $R_2$ are both cyclopropyl; $R_3$ and $R_4$ are both ethyl; $R_7$ and $R_8$ are both —H; $R_1$ and $R_2$ are both cyclopropyl; $R_3$ and $R_4$ are both methyl; $R_7$ is methyl; $R_8$ is —H; $R_1$ and $R_2$ are both 1-methylcyclopropyl; $R_3$ and $R_4$ are both methyl; Y' is bond; $R_1$ and $R_2$ are both 1-methylcyclopropyl; $R_3$ and $R_4$ are both methyl; $R_7$ and $R_8$ are both —H; $R_1$ and $R_2$ are both 1-methylcyclopropyl; $R_3$ and $R_4$ are both methyl; $R_7$ is methyl and $R_8$ is —H; $R_1$ and $R_2$ are both 1-methylcyclopropyl; $R_3$ and $R_4$ are both methyl; $R_7$ is ethyl and $R_8$ is —H; $R_1$ and $R_2$ are both 1-methylcyclopropyl; $R_3$ and $R_4$ are both methyl; $R_7$ is n-propyl and $R_8$ is —H; $R_1$ and $R_2$ are both 1-methylcyclopropyl; $R_3$ and $R_4$ are both methyl; $R_7$ and $R_8$ are both methyl; $R_1$ and $R_2$ are both 1-methylcyclopropyl; $R_3$ and $R_4$ are both ethyl; $R_7$ and $R_8$ are both —H; $R_1$ and $R_2$ are both 1-methylcyclopropyl; $R_3$ is methyl, and $R_4$ is ethyl; $R_7$ and $R_8$ are both —H; $R_1$ and $R_2$ are both 2-methylcyclopropyl; $R_3$ and $R_4$ are both methyl; $R_7$ and $R_8$ are both —H; $R_1$ and $R_2$ are both 2-phenylcyclopropyl; $R_3$ and $R_4$ are both methyl; $R_7$ and $R_8$ are both —H; $R_1$ and $R_2$ are both 1-phenylcyclopropyl; $R_3$ and $R_4$ are both methyl; $R_7$ and $R_8$ are both —H; $R_1$ and $R_2$ are both cyclobutyl; $R_3$ and $R_4$ are both methyl; $R_7$ and $R_8$ are both —H; $R_1$ and $R_2$ are both cyclopentyl; $R_3$ and $R_4$ are both methyl; $R_7$ and $R_8$ are both —H; $R_1$ and $R_2$ are both cyclohexyl; $R_3$ and $R_4$ are both methyl; $R_7$ and $R_8$ are both —H; $R_1$ and $R_2$ are both cyclohexyl; $R_3$ and $R_4$ are both phenyl; $R_7$ and $R_8$ are both —H; $R_1$ and $R_2$ are both methyl; $R_3$ and $R_4$ are both methyl; $R_7$ and $R_8$ are both —H; $R_1$ and $R_2$ are both methyl; $R_3$ and $R_4$ are both phenyl; $R_7$ and $R_8$ are both —H; $R_1$ and $R_2$ are both t-butyl; $R_3$ and $R_4$ are both methyl; $R_7$ and $R_8$ are both —H; $R_1$ and $R_2$ are both t-butyl; $R_3$ and $R_4$ are both phenyl; $R_7$ and $R_8$ are both —H; $R_1$ and $R_2$ are both t-butyl; $R_3$ and $R_4$ are both methyl; $R_7$ and $R_8$ are both —H; $R_1$ and $R_2$ are ethyl; $R_3$ and $R_4$ are both methyl; $R_7$ and $R_8$ are both —H; $R_1$ and $R_2$ are both n-propyl; $R_3$ and $R_4$ are both methyl; $R_7$ and $R_8$ are both —H. Y in these examples is preferably —C($R_7R_8$)—.

In another preferred embodiment, the compound used in the method of the present invention is represented by Structural Formula (V):

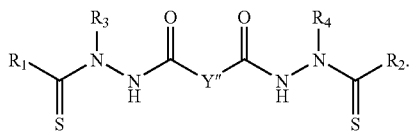

$R_1$-$R_4$ in Structural Formula (V) are as described in Structural Formula (I). Y" is a covalent bond or —CH$_2$—.

In a first example of a compound represented by Structural Formula (V), $R_3$ and $R_4$ are both a substituted or unsubstituted aliphatic group, preferably both a substituted or unsubstituted alkyl group and more preferably both a methyl or ethyl group. When $R_3$ and $R_4$ in Structural Formula (V) are both a substituted or unsubstituted aliphatic group, then: 1) $R_1$ and $R_2$ are preferably both a substituted or unsubstituted aliphatic group (e.g., a substituted or unsubstituted alkyl group and preferably a C3-C8 substituted or unsubstituted cycloalkyl group such as a substituted or unsubstituted cyclopropyl group); or 2) $R_1$ and $R_2$ are preferably both a substituted or unsubstituted aryl group (e.g., a substituted or unsubstituted heteroaryl group or a substituted or unsubstituted phenyl group; or 3) $R_1$ is preferably a substituted or unsubstituted aliphatic group (preferably a substituted or unsubstituted cycloalkyl group such as a substituted or unsubstituted cyclopropyl group); and $R_2$ is preferably a substituted or unsubstituted aryl group (e.g., a substituted or unsubstituted heteroaryl group or a substituted or unsubstituted phenyl group.

In a second example of a compound represented by Structural Formula (V), $R_3$ and $R_4$ are both a substituted or unsubstituted heteroaryl group. When $R_3$ and $R_4$ in Structural Formula (V) are both a substituted or unsubstituted heteroaryl group, then: 1) $R_1$ and $R_2$ are preferably both a substituted or unsubstituted phenyl group; 2) $R_1$ and $R_2$ are preferably both a substituted or unsubstituted heteroaryl group; 3) $R_1$ and $R_2$ are preferably both a substituted or unsubstituted aliphatic group (preferably a substituted or unsubstituted alkyl group and more preferably a substituted or unsubstituted cycloalkyl group such as a substituted or unsubstituted cyclopropyl group); or 4) $R_1$ is preferably a substituted or unsubstituted aliphatic group (preferably a substituted or unsubstituted C3-C8 cycloalkyl group); and $R_2$ is preferably a substituted or unsubstituted aryl group (e.g., a substituted or unsubstituted heteroaryl group or a substituted or unsubstituted phenyl group).

In a third example of a compound represented by Structural Formula (V), $R_3$ and $R_4$ are both a substituted or unsubstituted phenyl group. When $R_3$ and $R_4$ in Structural Formula (V) are both a substituted or unsubstituted phenyl group, then: 1) $R_1$ and $R_2$ are preferably both a substituted or unsubstituted phenyl group; 2) $R_1$ and $R_2$ are preferably both a substituted or unsubstituted heteroaryl group; 3) $R_1$ and $R_2$ are both a substituted or unsubstituted aliphatic group (preferably a substituted or unsubstituted alkyl group and more preferably a C3-C8 substituted or unsubstituted cyclic aliphatic group such as a substituted or unsubstituted cyclopropyl group); or 4) $R_1$ is a substituted or unsubstituted aliphatic group (preferably a substituted or unsubstituted cycloalkyl group such as a cyclopropyl group); and $R_2$ is a substituted or unsubstituted aryl group (e.g., a substituted or unsubstituted heteroaryl group or a substituted or unsubstituted phenyl group.

In a fourth example of a compound represented by Structural Formula (V), $R_1$ and $R_2$ are both a substituted or unsubstituted aryl group (e.g., a substituted or unsubstituted heteroaryl group or a substituted or unsubstituted phenyl group). More preferably, $R_3$ and $R_4$ are both methyl.

In a fifth example of a compound represented by Structural Formula (V), $R_1$ and $R_2$ are both a substituted or unsubstituted aliphatic group, preferably both a substituted or unsubstituted alkyl group, including a C3-C8 cycloalkyl group optionally substituted with at least one alkyl group (e.g., methyl, ethyl, n-propyl, n-butyl, n-pentyl, cyclopropyl, 1-methylcyclopropyl, 2-methylcyclopropyl, cyclobutyl, cyclopentyl, or cyclohexyl). When $R_1$ and $R_2$ in Structural Formula (V) are both an aliphatic group or a substituted aliphatic group, then $R_3$ and $R_4$ are preferably both: 1) a substituted or unsubstituted aryl group (e.g., a substituted or unsubstituted heteroaryl group or a substituted or unsubstituted phenyl group); or 2) a substituted or unsubstituted aliphatic group (preferably a substituted or unsubstituted alkyl group).

In a sixth example of a compound represented by Structural Formula (V), $R_1$ and $R_2$ are both a substituted or unsubstituted cycloalkyl group, preferably both a substituted or unsubstituted cyclopropyl alkyl group and $R_3$ and $R_4$ are as described for Structural Formula (I).

In a seventh example of a compound represented by Structural Formula (V), $R_1$ is a substituted or unsubstituted aliphatic group and $R_2$ is a substituted or insubstituted aryl group and $R_3$ and $R_4$ are as described for Structural Formula (I).

The following are specific examples of compounds represented by Structural Formula (V): $R_1$ and $R_2$ are both phenyl, and $R_3$ and $R_4$ are both o-CH$_3$-phenyl; $R_1$ and $R_2$ are both o-CH$_3$C(O)O-phenyl, and $R_3$ and $R_4$ are phenyl; $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both phenyl, and $R_3$ and $R_4$ are both n-propyl; $R_1$ and $R_2$ are both p-cyanophenyl, and $R_3$ and $R_4$ are both methyl; $R_1$ and $R_2$ are both p-nitro phenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both n-butyl; $R_1$ and $R_2$ are both p-chlorophenyl, and $R_3$ and $R_4$ are both methyl; $R_1$ and $R_2$ are both 3-nitrophenyl, and $R_3$ and $R_4$ are both methyl; $R_1$ and $R_2$ are both 3-cyanophenyl, and $R_3$ and $R_4$ are both methyl; $R_1$ and $R_2$ are both 3-fluorophenyl, and $R_3$ and $R_4$ are both methyl; $R_1$ and $R_2$ are both 2-furanyl, and $R_3$ and $R_4$ are both phenyl; $R_1$ and $R_2$ are both 2-methoxyphenyl, and $R_3$ and $R_4$ are both methyl; $R_1$ and $R_2$ are both 3-methoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2-methoxy-5-chlorophenyl, and $R_3$ and $R_4$ are both ethyl; $R_1$ and $R_2$ are both 2,5-difluorophenyl, and $R_3$ and $R_4$ are both methyl; $R_1$ and $R_2$ are both 2,5-dichlorophenyl, and $R_3$ and $R_4$ are both methyl; $R_1$ and $R_2$ are both 2,5-dimethylphenyl, and $R_3$ and $R_4$ are both methyl; $R_1$ and $R_2$ are both 2-methoxy-5-chlorophenyl, and $R_3$ and $R_4$ are both methyl; $R_1$ and $R_2$ are both 3,6-dimethoxyphenyl, and $R_3$ and $R_4$ are both methyl; $R_1$ and $R_2$ are both phenyl, and $R_3$ and $R_4$ are both 2-ethylphenyl; $R_1$ and $R_2$ are both 2-methyl-5-pyridyl, and $R_3$ and $R_4$ are both methyl; or $R_1$ is phenyl; $R_2$ is 2,5-dimethoxyphenyl, and $R_3$ and $R_4$ are both methyl; $R_1$ and $R_2$ are both methyl, and $R_3$ and $R_4$ are both p-CF$_3$-phenyl; $R_1$ and $R_2$ are both methyl, and $R_3$ and $R_4$ are both o-CH$_3$-phenyl; R$_1$ and R$_2$ are both —(CH$_2$)$_3$COOH; and R$_3$ and R$_4$ are both phenyl; R$_1$ and R$_2$ are both represented by the following structural formula:

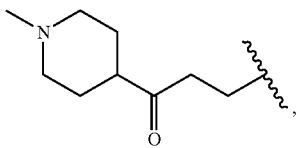

and R$_3$ and R$_4$ are both phenyl; R$_1$ and R$_2$ are both n-butyl, and R$_3$ and R$_4$ are both phenyl; R$_1$ and R$_2$ are both n-pentyl, R$_3$ and R$_4$ are both phenyl; R$_1$ and R$_2$ are both methyl, and R$_3$ and R$_4$ are both 2-pyridyl; R$_1$ and R$_2$ are both cyclohexyl, and R$_3$ and R$_4$ are both phenyl; R$_1$ and R$_2$ are both methyl, and R$_3$ and R$_4$ are both 2-ethylphenyl; R$_1$ and R$_2$ are both methyl, and R$_3$ and R$_4$ are both 2,6-dichlorophenyl; R$_1$-R$_4$ are all methyl; R$_1$ and R$_2$ are both methyl, and R$_3$ and R$_4$ are both t-butyl; R$_1$ and R$_2$ are both ethyl, and R$_3$ and R$_4$ are both methyl; R$_1$ and R$_2$ are both t-butyl, and R$_3$ and R$_4$ are both methyl; R$_1$ and R$_2$ are both cyclopropyl, and R$_3$ and R$_4$ are both methyl; R$_1$ and R$_2$ are both cyclopropyl, and R$_3$ and R$_4$ are both ethyl; R$_1$ and R$_2$ are both 1-methylcyclopropyl, and R$_3$ and R$_4$ are both methyl; R$_1$ and R$_2$ are both 2-methylcyclopropyl, and R$_3$ and R$_4$ are both methyl; R$_1$ and R$_2$ are both 1-phenylcyclopropyl, and R$_3$ and R$_4$ are both methyl; R$_1$ and R$_2$ are both 2-phenylcyclopropyl, and R$_3$ and R$_4$ are both methyl; R$_1$ and R$_2$ are both cyclobutyl, and R$_3$ and R$_4$ are both methyl; R$_1$ and R$_2$ are both cyclopentyl, and R$_3$ and R$_4$ are both methyl; R$_1$ is cyclopropyl, R$_2$ is phenyl, and R$_3$ and R$_4$ are both methyl. In these examples, Y" is preferably —CH$_2$—.

In another preferred embodiment, Y the compound used in the method of the present invention is represented by Structural Formula (VI):

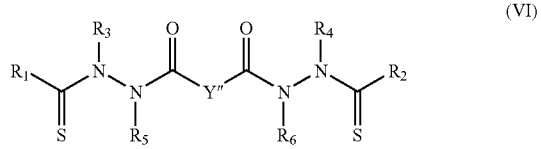

(VI)

R$_1$-R$_6$ in Structural Formula (VI) are as described for Structural Formula (I). Y" is a covalent bond or —CH$_2$—.

In one example of a compound represented by Structural Formula (VI), R$_5$ and R$_6$ are both an alkyl group (preferably methyl) or a phenyl group. When R$_5$ and R$_6$ are both an alkyl group or a phenyl group, then R$_1$ and R$_2$ are preferably both phenyl or substituted phenyl and R$_3$ and R$_4$ are preferably both an alkyl group.

In a second example of a compound represented by Structural Formula (V), R$_5$ and R$_6$ are both an alkyl group (preferably methyl) or a phenyl group. When R$_5$ and R$_6$ are both an alkyl group or a phenyl group, then R$_1$ and R$_2$ are preferably both alkyl or substituted alkyl and R$_3$ and R$_4$ are preferably both phenyl or substituted phenyl. Alternatively, when R$_5$ and R$_6$ are both an alkyl group or a phenyl group, R$_1$ and R$_2$ are both an alkyl group or a substituted alkyl group and R$_3$ and R$_4$ are both alkyl or substituted alkyl.

The following are more specific examples of compounds of the present invention: R$_1$ and R$_2$ are both phenyl, R$_3$ and R$_4$ are both phenyl, R$_5$ and R$_6$ are both methyl, and R$_7$ and R$_8$ are both —H; R$_1$ and R$_2$ are both phenyl, R$_3$ and R$_4$ are both phenyl, R$_5$ and R$_6$ are both n-hexyl, and R$_7$ and R$_8$ are both —H; R$_1$ and R$_2$ are both phenyl, R$_3$ and R$_4$ are both methyl, R$_5$ and R$_6$ are both methyl, and R$_7$ and R$_8$ are both —H; R$_1$ and R$_2$ are both phenyl, R$_3$ and R$_4$ are both methyl, R$_5$ and R$_6$ are both methyl, and R$_7$ is —H and R$_8$ is methyl; R$_1$ and R$_2$ are both phenyl, R$_3$ and R$_4$ are both —H, R$_5$ and R$_6$ are both phenyl, R$_7$ is —H, and R$_8$ is methyl; R$_1$ and R$_2$ are both 4-chlorophenyl, R$_3$ and R$_4$ are both methyl, R$_5$ and R$_6$ are both methyl, and R$_7$ and R$_8$ are both —H; R$_1$ and R$_2$ are both phenyl, R$_3$ and R$_4$ are both phenyl, R$_5$ and R$_6$ are both methyl, and R$_7$ and R$_8$ are both —H; R$_1$ and R$_2$ are both phenyl, R$_3$ and R$_4$ are both phenyl, R$_5$ and R$_6$ are both n-hexyl, and R$_7$ and R$_8$ are both —H; R$_1$ and R$_2$ are both phenyl, R$_3$ and R$_4$ are both methyl, R$_5$ and R$_6$ are both methyl, and R$_7$ and R$_8$ are both —H; R$_1$ and R$_2$ are both phenyl, R$_3$ and R$_4$ are both methyl, R$_5$ and R$_6$ are both methyl, and R$_7$ is —H and R$_8$ is methyl; R$_1$ and R$_2$ are both phenyl, R$_3$ and R$_4$ are both —H, R$_5$ and R$_6$ are both phenyl, R$_7$ is —H, and R$_8$ is methyl; R$_1$ and R$_2$ are both 4-chlorophenyl, R$_3$ and R$_4$ are both methyl, R$_5$ and R$_6$ are both methyl, and R$_7$ and R$_8$ are both —H.

In Structural Formulas (I)-(VI), R$_1$ and R$_2$ are the same or different; and/or R$_3$ and R$_4$ are the same or different; and/or R$_5$ and R$_6$ are the same or different. Preferably, R$_1$ and R$_2$ are the same, R$_3$ and R$_4$ are the same and R$_5$ and R$_6$ are the same.

A "straight chained hydrocarbyl group" is an alkylene group, i.e., —(CH$_2$)$_n$—, with one or more (preferably one) internal methylene groups optionally replaced with a linkage group. x is a positive integer (e.g., between 1 and about 10), preferably between 1 and about 6 and more preferably 1 or 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine [—N(R$^a$)]—, wherein R$^a$ is defined below. A preferred linkage group is —C(R$_7$R$_8$)—, wherein R$_7$ and R$_8$ are defined above. Suitable substitutents for an alkylene group and a hydrocarbaryl group are those which do not substantially interfere with the anti-cancer activity of the disclosed compounds. R$_7$ and R$_8$ are preferred substituents for an alkylene or hydrocarbyl group represented by Y or Y'.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g, methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1-C20 straight chained or branched alkyl group or a C3-C8 cyclic alkyl group is also referred to as a "lower alkyl" group.

Aromatic groups include carbocyclic aromatic groups such as phenyl, naphthyl, and anthracyl, and heteroaryl groups such as imidazolyl, thienyl, furanyl, pyridyl, pyrimidyl, pyranyl, pyrazolyl, pyrroyl, pyrazinyl, thiazole, oxazolyl, and tetrazole.

Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

The term "arylene" refers to an aryl group which is connected to the remainder of the molecule by two other bonds. By way of example, the structure of a 1,4-phenylene group is shown below:

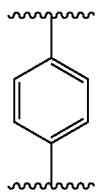

Substituents for an arylene group are as described below for an aryl group.

Non-aromatic heterocyclic rings are non-aromatic carbocyclic rings which include one or more heteroatoms such as nitrogen, oxygen or sulfur in the ring. The ring can be five, six, seven or eight-membered. Examples include tetrahydrofuranyl, tetrahyrothiophenyl, morpholino, thiomorpholino, pyrrolidinyl, piperazinyl, piperidinyl, and thiazolidinyl.

Suitable substituents on an aliphatic group (including an alkylene group), non-aromatic heterocyclic group, benzylic or aryl group (carbocyclic and heteroaryl) are those which do not substantially interfere with the anti-cancer activity of the disclosed compounds. A substituent substantially interferes with anti-cancer activity when the anti-cancer activity is reduced by more than about 50% in a compound with the substituent compared with a compound without the substituent. Examples of suitable substituents include —OH, halogen (—Br, —Cl, —I and —F), —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHNR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SO$_k$R$^a$ (k is 0, 1 or 2) and —NH—C(=NH)—NH$_2$.R$^a$—R$^d$ are each independently an aliphatic, substituted aliphatic, benzyl, substituted benzyl, aryl or substituted aryl group, preferably an alkyl, benzylic or aryl group. In addition, —N(R$^a$R$^b$), taken together, can also form a substituted or unsubstituted non-aromatic heterocyclic group. A non-aromatic heterocyclic group, benzylic group or aryl group can also have an aliphatic or substituted aliphatic group as a substituent. A substituted aliphatic group can also have a non-aromatic heterocyclic ring, a substituted a non-aromatic heterocyclic ring, benzyl, substituted benzyl, aryl or substituted aryl group as a substituent. A substituted aliphatic, non-aromatic heterocyclic group, substituted aryl, or substituted benzyl group can have more than one substituent. Examples of preferred substituents for the groups represented by R$^a$—R$^d$ and —N(R$^a$R$^b$) taken together include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Preferred substituents for a cycloalkyl group, including cycloalkyl groups represented by R$_1$ and R$_2$, are alkyl groups, such as a methyl or ethyl group.

Also included in the present invention are pharmaceutically acceptable salts of the compounds described herein. Compounds disclosed herein which possess a sufficiently acidic, a sufficiently basic, or both functional groups, and accordingly can react with any of a number of organic or inorganic bases, and inorganic and organic acids, to form a salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

An noted above, the present invention is directed to treating subjects with cancer. "Treating a subject with cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as tissue or serum components).

Cancers that can be treated or prevented by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1 (murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic) cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 of *Holland Frie Cancer Medicine* 5th Ed., Bast et al. Eds., B. C. Decker Inc. (2000). The entire teachings of the preceding references are incorporated herein by reference.

In one embodiment, the disclosed method is believed to be particularly effective in treating subject with non-solid tumors such as multiple myeloma. In another embodiment, the disclosed method is believed to be particularly effective against T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1 (acute) cell line); and lymphoma (e.g., as exemplified by the U937 cell line); most preferably, this embodiment of the method employs Compound (1).

The disclosed method is particularly effective at treating subjects whose cancer has become "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

An "effective amount" is the quantity of compound in which a beneficial clinical outcome is achieved when the compound is administered to a subject with a cancer. A "beneficial clinical outcome" includes a reduction in tumor mass, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of cancer. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 5 grams/mm$^2$.

The disclosed compounds are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compounds can also be administered orally (e.g., dietary), topically, by inhalation (e.g., intrabronchial, intranasal, oral inhalation or intranasal drops), or rectally, depending on the type of cancer to be treated. Oral or parenteral administration are preferred modes of administration.

The disclosed compounds can be administered to the subject in conjunction with an acceptable pharmaceutical carrier as part of a pharmaceutical composition for treatment of cancer. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrasn) are known in the art (Baker, et al., "Controlled Release of Biological Active Agents", John Wiley and Sons, 1986).

Optionally, the disclosed compounds can be co-administered with other anti-cancer agents such as Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1 interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide;

rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used include but are not limited to HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-$\beta_2$ antibody (Cambridge Ab Tech).

Chemotherapeutic agents that can be used in the methods and compositions of the invention include but are not limited to alkylating agents, antimetabolites, natural products, or hormones. Examples of alkylating agents useful for the treatment or prevention of T-cell malignancies in the methods and compositions of the invention include but are not limited to, nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites useful for the treatment or prevention of T-cell malignancies in the methods and compositions of the invention include but are not limited to folic acid analog (e.g., methotrexate), or pyrimidine analogs (e.g., Cytarabine), purine analogs (e.g., mercaptopurine, thioguanine, pentostatin). Examples of natural products useful for the treatment or prevention of T-cell malignancies in the methods and compositions of the invention include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents useful for the treatment or prevention of cancer in the methods and compositions of the invention include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful for the treatment or prevention of cancer in the methods and compositions of the invention include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of natural products useful for the treatment or prevention of cancer in the methods and compositions of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., L-asparaginase), or biological response modifiers (e.g., interferon alpha). Examples of hormones and antagonists useful for the treatment or prevention of cancer in the methods and compositions of the invention include but are not limited to adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

The compounds disclosed herein are believed to be particularly effective when co-administered with anti-cancer agents which act by arresting cells in the G2-M phases due to stabilized microtubules. Thus, the disclosed method preferably includes co-administered anti-cancer drugs which act by this mechanism. However, Paclitaxel and analogs of Paclitaxel are excluded from the present invention unless a multi-drug resistant cancer is being treated. Examples of anti-cancer agents which act by arresting cells in the G2-M phases due to stabilized microtubules include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser-.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-0Y-007 (National Health Research Institutes), and SSR-250411 (Sanofi).

Paclitaxel, also referred to as "TAXOL", is a well-known anti-cancer drug which acts by inhibiting microtubule formation. Many analogs of paclitaxel are known, including docetaxol, which is also referred to as "TAXOTERE". Other paclitaxel analogs are disclosed in the co-pending U.S. Ser. Nos. 10/193,075 and 10/193,639, both entitled TAXOL ENHANCER COMPOUNDS and both filed Jul. 10, 2002, the entire teachings of which are incorporated herein by reference. A "paclitaxel analog" is defined herein to mean a compound which has the basic taxane skeleton and the ability to arrest cells in the G2-M phases due to stabilized microtubules. The basic taxane skeleton is shown below in Structural Formula (VII):

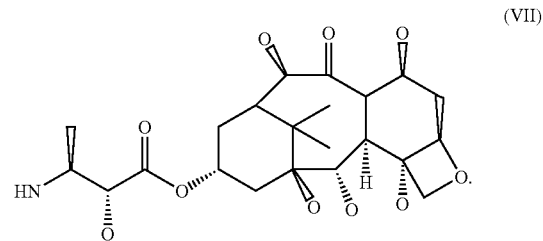

Double bonds have been omitted from the cyclohexane rings in the taxane skeleton represented by Structural Formula (VII). It is to be understood that the basic taxane skeleton can include zero or one double bond in one or both cyclohexane rings. In addition, a wide variety of substituents can decorate the taxane skeleton without adversely affecting biological activity. A number of atoms have also omitted from Structural Formula (VII) to indicate sites in which structural variation commonly occurs among paclitaxel analogs. For example, substitution on the taxane skeleton with simply an oxygen atom indicates that hydroxyl, acyl, alkoxy or other oxygen-bearing substituent is commonly found at the site. It is to be understood that these and other substitutions on the taxane skeleton can also be made without losing the ability to enhance and stabilize microtubule formation.

The disclosed compounds can be prepared according to methods described in Examples 1-14 and also according to methods described in the co-pending U.S. Ser. No. 10/193,076, entitled SYNTHESIS OF TAXOL ENHANCERS, filed Jul. 10, 2002. The entire teachings of this application are incorporated herein by reference.

Data showing the efficacy of the disclosed compounds are provided in Examples 15-18. Other anti-cancer data for the disclosed compounds are provided in the co-pending U.S. Ser. Nos. 10/193,075 and 10/193,639, both entitled TAXOL ENHANCER COMPOUNDS and both filed Jul. 10, 2002, the entire teachings of which are incorporated herein by reference.

The present invention is illustrated by the following examples, which are not intended to be limiting in any way.

EXEMPLIFICATION

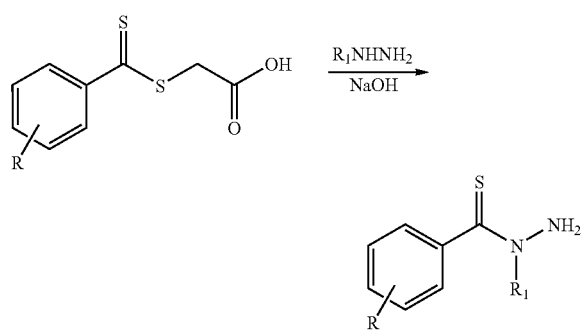

Thiobenzoic acid N-methylhydrazide were prepared in 88% yield by slight modification of the prior art (Acta Chem. Scand. 1961, 1087-1096); $^1$H NMR (CDCl$_3$) δ 3.3 (s, 3H), 6.0 (s, 2H), 7.3-7.4 (m, 5H); ESMS calcd (C$_8$H$_{10}$N$_2$S): 166.1; found: 167.1 (M+H)$^+$.

Example 2

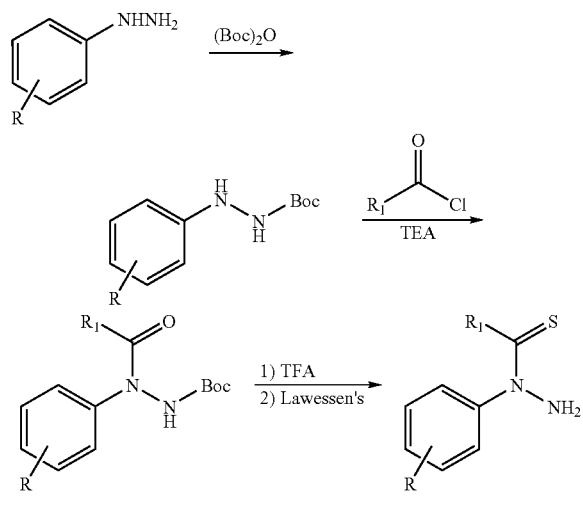

Preparation of Thiocyclohexanoic acid N-phenylhydrazide

Phenyl hydrazine (5.4 g, 50 mmol) was dissolved in dry dichloromethane (50 mL) in a 250 mL round bottom flask. Di-tert-butyl dicarbonate (10.9 g, 50 mmol) was then added with stirring at 0° C. The resultant solution was then stirred under reflux for 3 h. Removal of the volatile components under reduced pressure afforded a colorless solid, which was washed with hexane and dried in vacuo. 10 g (yield 96%) of the product was obtained as a colorless solid, which can be used in the next step without further purification. 2.5 g (12 mmol) of this material was dissolved in dry pyridine (5 mL). Cyclohexanecarbonyl chloride (2.0 mL, 15 mmol) was then added slowly at 0° C. The red solution was stirred at 0° C. for half an hour and the resultant yellow suspension was stirred at rt for 3 h before pouring into ice-H$_2$O (100 mL). The precipitate product was collected by filtration and washed thoroughly with H$_2$O. After one recrystallization from EtOH/H$_2$O, 3.63 g (95%) of N-phenyl-N-cyclohexyl-N'-tert-butoxycarbonylhydrazide was obtained as a white powder; mp 141-143° C.; $^1$H NMR (CDCl$_3$) δ 0.9-2.3 (m, 11H), 1.4 (s, 9H), 6.9 (br, 1H), 7.4 (m, 5H) ppm.

To a solution of N-phenyl-N-cyclohexyl-N'-tert-butoxycarbonylhydrazide (1.1 g, 3.46 mmol) in dichloromethane (6 mL) was added trifluoroacetic acid (6 mL) at 0° C. The resultant solution was stirred at 0° C. for half an hour. Volatile components were then removed under reduced pressure to afford a syrup, which was turned into a solid upon standing; this material was briefly mixed with cold 2 N NaOH (5 mL) for a few minutes at 0° C. Solid product was then collected by filtration and recrystallized from hexane to afford cyclohexanoic acid N-phenylhydrazide (0.6 g, 80% yield) as a white powder; $^1$H NMR (DMSO-d$_6$) δ 0.8-3.2 (m, 1H), 5.3 (s, 2H), 7.0-7.7 (m, 5H); ESMS calcd (C$_{13}$H$_{18}$N$_2$O): 218.3; found: 241.1 (M+Na)$^+$.

A mixture of cyclohexanoic acid N-phenylhydrazide (0.25 g, 1.15 mmol) and Lawesson's Reagent (0.46 g, 1.15 mmol) in dry toluene (20 mL) was stirred under reflux for 1 h. After being cooled to room temperature, the mixture was filtered through a short column of silica gel (5 g) which was pre-washed with benzene. Removal of benzene afforded the crude product as a solid which was purified by column chromatography on silica gel using hexane/EtOAc (4:1 v/v) as eluant. 0.15 g (60%) of thiocyclohexanoic acid N-phenylhydrazide was obtained as an off white solid. $^1$H NMR (CDCl$_3$) δ 0.8-2.4 (m, 11H), 5.65 (br, 1H), 7.1-7.6 (m, 5H); ESMS calcd (C$_{13}$H$_{18}$N$_2$S): 234.1; found: 235.1 (M+H)$^+$.

Example 3

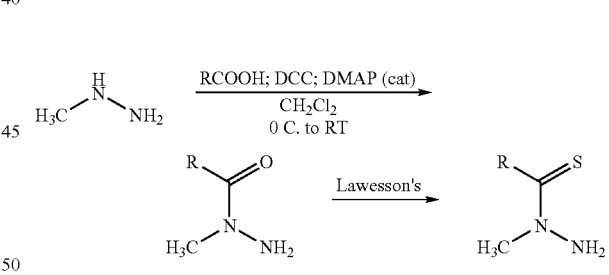

Preparation of 2,5-Dimethoxythiobenzoic acid N-methylhydrazine: DCC (4.5 g, 21.8 mmol) was added in one portion to a solution of 2,5-dimethoxybenzoic acid (3.6 g, 20 mol), methylhydrazine (1.2 ml, 23 mmol) and DMAP (30 mg, cat.) in CH$_2$Cl$_2$ (60 ml) cooled in an ice bath. The reaction mixture was stirred overnight at room temperature. The slurry was cooled at −20° C. for 1 h and filtered. The CH$_2$Cl$_2$ solution was evaporated and the residue was dried in vacuum. The resulting crude product was dissolved in toluene (50 ml). To this solution was added Lawesson's reagent (5.8 g, 14 mmol). The mixture was refluxed for 40 min, cooled to room temperature, and directly subjected to silica gel column chromatography (eluent: 25% to 35% ethyl acetate in hexanes) to give the 2,5-dimethoxythiobenzoic acid N-methylhydrazide (3.7 g, yield: 82%) as off-white solid. $^1$H NMR (300 MHz, CDCl$_3$): δ 6.88-6.80 (m, 3H), 5.46 (s, 2H), 3.84 (s, 3H), 3.82 (s, 3H), 3.28 (s, 3H).

Example 4

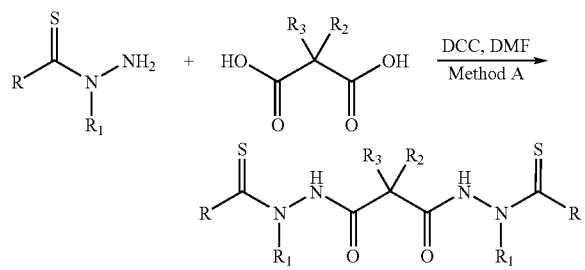

Preparation of N-Malonyl-bis[N'-methyl-N'-(thiobenzoyl) hydrazide]: To a stirred solution of thiobenzoic acid N-methylhydrazide (0.166 g, 10 mmol), HOBtH$_2$O (0.15 g, 11 mmol) and malonic acid (0.052 g, 5 mmol) in DMF (2 mL) was added DCC (0.22 g, 10.7 mmol) at 0° C. The resultant suspension was stirred at 0° C. for 1 h and at room temperature for 3 h. Precipitated material was filtered off and washed with EtOAc (3×15 mL). Combined filtrate and washings was washed successively with H$_2$O (2×20 mL), 5% citric acid (20 mL), H$_2$O (20 mL), Saturated NaHCO$_3$ (20 mL) and brine (20 mL). After being dried over Na$_2$SO$_4$, the solvent was removed under reduced pressure to afford the crude product as a yellow solid, which was washed with warm EtOAc. 0.16 g (yield 80%) of pure product was obtained as a yellow powder. R$_f$ 0.3 (Hexane/EtOAc 1:1 v/v); $^1$H NMR (CDCl$_3$) δ 3.1-3.8 (m, 6H), 3.4 (s, 2H), 7.1-7.45 (m, 10H), 9.5-10.5 (m, 1H) ppm; ESMS calcd (C$_{19}$H$_{20}$N$_4$O$_2$S$_2$): 400.1; found: 399.1 (M−H)$^+$.

Preparation of N-(2-Methylmalonyl-bis {N'-methyl-N'-[(2,5-dimethoxy)thiobenzoyl]hydrazide]

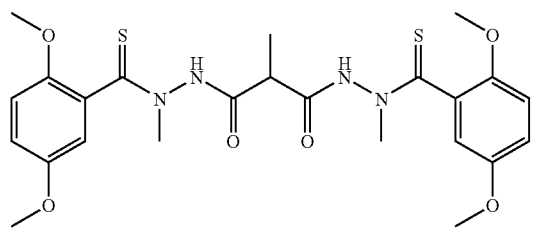

DCC (4 g, 19 mmol) was added to a solution of 2,5-dimethoxythiobenzoic acid N-methylhydrazide (3.7 g, 16.4 mmol) and 2-methylmalonic acid (2 g, 17 mmol) in DMF (20 ml) with stirring at 0° C. The reaction mixture was stirred for 1 h at room temperature. The slurry was cooled at −20° C. for 1 h and filtered. The filtrate was diluted with EtOAc (300 ml), washed with water (50 ml×3), dried with Na$_2$SO$_4$. The EtOAc solution was concentrated to minimum volume, and subjected to silica gel column chromatography (eluent: 1:4 to 2:1, ethyl acetate:hexanes) to give the title compound (3.5 g, 80%) as yellow powder. $^1$H NMR (CDCl$_3$) δ 10.12-9.14 (2H), 7.12-6.81 (m, 6H), 4.01-3.78 (m, 6H), 3.75-3.22 (m, 6H), 2.82-2.62 (m, 1H), 1.12-0.11 (m, 3H); ESMS cacld (C$_{24}$H$_{30}$N$_4$O$_6$S$_2$):534.16; found: 535.1 (M+H).

Preparation of 2-Methylmalonyl-bis(2-Amino-2,3-dihydro-isoindole-1-thione)

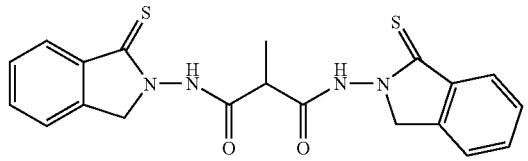

2-carboxybenzaldehyde (150 mg, 1 mmol) and carbazic acid (132 mg, 1 mmol) in 40 ml methanol was stirred at room temperature for 4 h. To this solution was added Pd/C (60 mg, containing 50% H$_2$O), the reaction was under H$_2$ atmosphere for 3 h. The reaction mixture was filtered, and the solvent was evaporated. The resulting residue was subjected to silica gel column chromatography. (eluent: 20% to 50%, EtOAc in hexanes) to obtain 50 mg of product. $^1$H NMR (300 MHz, CDCl$_3$): 8.71-7.45 (m, 4H), 4.78 (s, 2H), 1.61 (s, 9H). The resulting product was dissolved in CF$_3$COOH (5 ml), stirred for 30 min. The CF$_3$COOH was evaporated, and the residue was subjected to silica gel column chromatography (eluent: 50% to 0%, hexanes in EtOAc) to give 2-amino-2,3-dihydro-isoindol-1-one (26 mg) as a white solid. $^1$H NMR (300 MHz, CDCl$_3$): 7.85-7.39 (m, 4H), 4.54 (s, 2H). MS: 149 (M+H). Subsequent Lawesson's thiolation and DCC coupling with 2-methylmaloic acid under conditions described above afforded 2-methylmalonyl-bis(2-amino-2,3-dihydro-isoindole-1-thione) as a yellow powder. $^1$H NMR (CDCl$_3$) δ 10.35 (s, 2H), 8.21-7.51 (m, 8H), 5.15 (s, 4H), 1.62 (s, 3H); ESMS cacld (C$_{20}$H$_{18}$N$_4$O$_2$S$_2$): 410.09; found: 411.1 (M+H).

Example 5

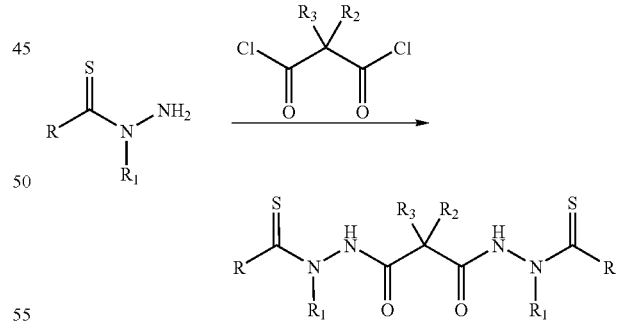

Preparation of N-Malonyl-bis[N'-methyl-N'-(thiobenzoyl) hydrazide]: To a solution of thiobenzoic acid N-methylhydrazine (10 g) stirred at 0 C were added subsequently triethylamine (8.5 mL) and malonyl dichloride (3.05 mL). The reaction mixture was stirred for 10 min, washed with water (3×50 mL), dried over sodium sulfate and concentrated. Purification by recrystallization from methylene dichloride (35 mL) gave the product as light yellow crystals (9.0 g, 75%) which was identical to the product obtained in Example 6.

Example 6

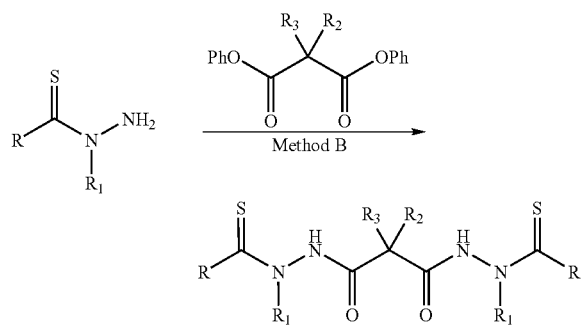

Preparation of N-Malonyl-bis[N'-methyl-N'-(thiobenzoyl) hydrazide]: A stirred solution of thiobenzoic acid N-methyl-hydrazide (1.66 g, 10 mmol) and diphenyl malonate (1.30 g, 5.08 mmol) in dry THF (100 mL) was heated to reflux for 72 h. Volatile components were then removed under reduced pressure. The crude product was purified by column chromatography on silica gel using a mixture of hexane and EtOAc as eluant (gradient from 4:1 v/v to 1:1 v/v). 1.07 g (51% yield) of pure product N-malonyl-bis[N'-methyl-N'-(thiobenzoyl)hydrazide] was obtained as a yellow powder. Physical property was identical to that obtained in Example 5.

Example 7

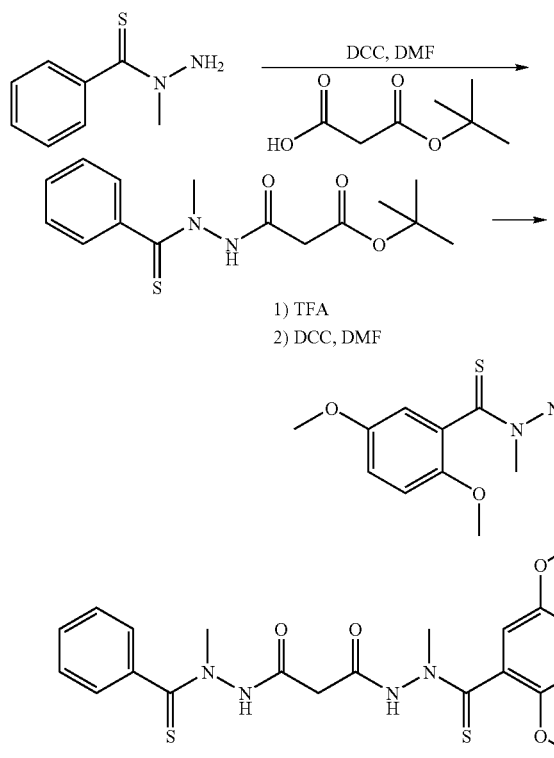

A slurry of thiobenzoic acid N-methylhydrazide (1.0 g, 6 mmol), mono-tert-butyl malonate (1.0 mL, 6 mmol), HOBt.H$_2$O (0.98 g, 7.2 mmol), and DCC (1.34 g, 6.5 mmol) in DMF (5 mL) was stirred at 0° C. for 3 h and then at room temperature for 3 h. Precipitated material was filtered off and washed with EtOAc (3×20 mL). Combined filtrate and washings was washed successively with H$_2$O (2×20 mL), 5% citric acid (20 mL), H$_2$O (20 mL), Saturated NaHCO$_3$ (20 mL) and brine (20 mL). After being dried over Na$_2$SO$_4$, the solvent was removed under reduced pressure to afford the crude product as a solid, which was washed with Et$_2$O. 0.94 g (yield 51%) of pure product N'-Methyl-N'-thiobenzoyl-hydrazinocarbonyl)-acetic acid tert-butyl ester was obtained as a yellow powder. $^1$H NMR (CDCl$_3$) δ 1.6-1.7 (ds, 9H), 3.1-4.1 (m, 5H), 7.3-7.7 (m, 5H), 9.7-10.3 (ds, 1H) ppm; ESMS calcd (C$_{15}$H$_{20}$N$_2$O$_3$S): 308; found: 307 (M−H)$^+$.

A solution of N'-methyl-N'-thiobenzoyl-hydrazinocarbonyl)-acetic acid tert-butyl ester (0.19 g, 0.6 mmol) and TFA (0.12 mL, 1.6 mmol) in dry DCM (10 mL) was stirred at 10° C.-15° C. for 12 h (reaction was monitored by TLC). Volatile components were removed under reduced pressure (bath temperature below 5° C.). After being dried in vacuo, DMF (3 mL) was added followed by the addition of DCC (0.13 g, 0.6 mmol), HOBtH$_2$O (93 mg, 0.7 mmol) and thio-2,5-dimethoxybenzoic acid N-methylhydrazide (0.13 g, 0.57 mmol). The resultant solution was stirred at 0° C. for half an hour and then at room temperature for 3 h. Precipitated material was filtered off and washed with EtOAc (3×10 mL). Combined filtrate and washings was washed successively with H$_2$O (2×10 mL), 5% citric acid (10 mL), H$_2$O (10 mL), Saturated NaHCO$_3$ (20 mL) and brine (20 mL). After being dried over Na$_2$SO$_4$, the solvent was removed under reduced pressure to afford the crude product as an oil, which was purified by SGC (4:1 hexane/EA to 2:1 EtOAc/Hexane). 0.14 g (yield 53%) of pure product was obtained as a yellow powder. $^1$H NMR (CDCl$_3$) δ 3.1-3.9 (m, 18H), 6.7-7.4 (m, 9H) ppm; ESMS calcd (C$_{21}$H$_{24}$N$_4$O$_4$S$_2$): 460.1; found: 461.1 (M+H)$^+$.

Example 8

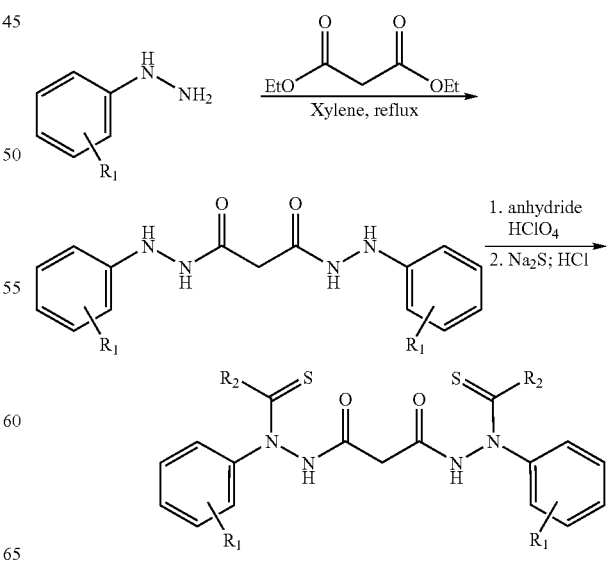

Preparation of N-Malonyl-bis[N'-phenyl-N'-(thioacetyl)hydrazide]

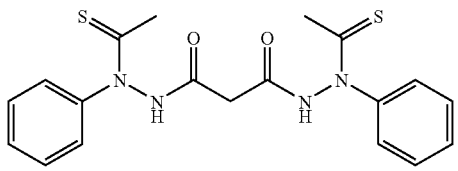

A mixture of phenylhydrazine (30 mL) and ethyl malonate (in xylene (150 mL) was heated to reflux overnight. The reaction was cooled to room temperature. The precipitates were collected via filtration and washed with ethanol to give N-malonyl-bis(N'-phenylhydrazide) as a white solid (14 g). The hydrazide (3.4 g) was suspended in acetic anhydride (30 mL) and cooled in an ice bath. To it was added dropwise perchloric acid (57% in water, 3 mL). The reaction mixture turned to clear solution initially and then quickly solidified. After standing at room temperature for 1 h, ether (50 mL) was added. The resulting slurry was filtered and washed with ether (2×00 mL) to give the perchlorate salts as a white solid (5.7 g). The salts were taken into acetone and added as a slurry over 5 min to Na$_2$S (0.6 M in water, 90 mL) stirred at room temperature. After 30 min, the reaction was acidified with HCl(c) to afford a yellow slurry. The solid was collected via filtration and washed with water (20 Ml) and ether (2×25 mL) to give N-malonyl-bis[N'-phenyl-N'-(thioacetyl)hydrazide] as an off-white solid (3.6 g). $^1$H NMR (DMSO-d$_6$): δ 11.5 (m, 2H); 7.5 (m, 10H); 3.2 (m, 2H); 2.6 (s, 3H); 2.5 (s, 3H). MS calcd (400.1); Found: 423.1 (M+Na).

Example 9

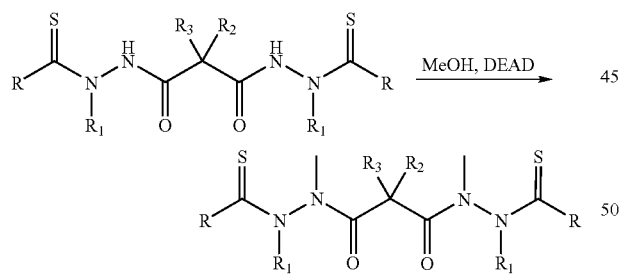

Preparation of N-Malonyl-bis[N-methyl-N'-phenyl-N'-(thiobenzoyl)hydrazide]

To a stirred solution of N-malonyl-bis[N'-phenyl-N'-(thiobenzoyl)hydrazide] (180 mg, 0.34 mmol), MeOH (22 uL) and triphenylphosphine (200 mg, 0.64 mmol) in dry THF (10 mL) was added a solution of DEAD (0.12 mL) in THF (3 mL) dropwise. The resultant orange solution was stirred at room temperature for 12 h. After removal of the volatile components, the crude product was purified by SGC (3:1 Hexane/EtOAc) to afford 98 mg (52% yield) of the title compound as syrup. $^1$H NMR (CDCl$_3$) δ 3.3-4.5 (m, 8H), 7.1-7.8 (m, 20H) ppm; ESMS calcd (C$_{31}$H$_{28}$N$_4$O$_2$S$_2$): 552; found: 551 (M–H)$^+$.

Example 10

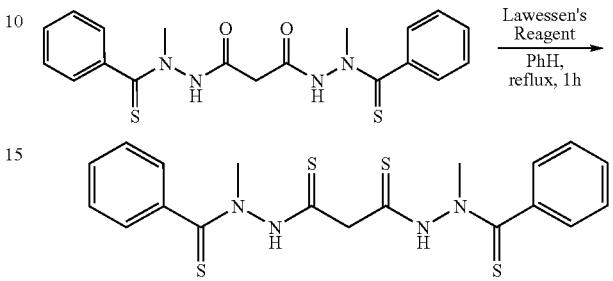

A stirred mixture of N-malonyl-bis[N'-phenyl-N'-(thioacetyl)hydrazide) starting material (0.1 g, 0.25 mmol) and Lawesson's reagent (0.15 g, 0.37 mmol) in dry benzene (20 mL) was heated to reflux for 1 h. After being cooled to room temperature, the mixture was filtered through a layer of silica gel, washed with THF (2×15 mL). The filtrate and washings were combined and concentrated under reduced pressure. Flush column chromatography on silica gel (hexane to 4:1 hexane/EtOAc to 2:1 hexane/EtOAc) afforded N-bisthiomalonyl-bis[N'-phenyl-N'-(thioacetyl)hydrazide as a clear syrup (16 mg, 15%). $^1$H NMR (CDCl$_3$) δ 3.80-3.95 (m, 8H), 7.02-7.30 (m, 10H). ESMS calcd (C$_{19}$H$_{20}$N$_4$S$_4$): 432.06; found: 433.0 (M+H)$^+$.

Example 11

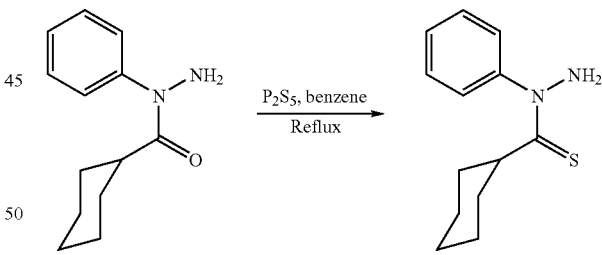

To a stirred solution of cyclohexanoic acid N-phenylhydrazide (0.1 g, 0.45 mmol) in dry benzene (5 mL) was added P$_2$S$_5$ (0.2 g, 0.45 mol). The resultant suspension was heated to reflux for 3 h. After being cooled to room temperature, the mixture was diluted with benzene (5 mL) and was filtered through a short column of silica gel (2 g), washed with benzene and 2:1 hexane/EtOAc (15 mL each). The filtrate and washings were combined and concentrated to afford a solid. Crystallized from hexane to provide the intermediate thiocyclohexanoic acid N-phenylhydrazide as an off white solid; $^1$H NMR (CDCl$_3$) δ 0.8-2.4 (m, 11H), 5.65 (br, 1H), 7.1-7.6 (m, 5H); ESMS calcd (C$_{13}$H$_{18}$N$_2$S): 234.1; found: 235.1 (M+H)$^+$.

Example 12

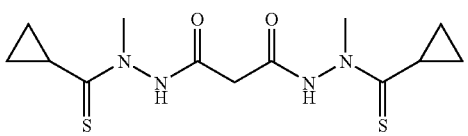

Cyclopropyl bromide (4.8 g, 40 mmol) was added into 50 ml anhydrous THF solution containing magnesium powder (1.1 g, 45 mmol), stirred for 30 min, and refluxed for another 30 min. After it was cooled, the clear reaction solution was added into carbon disulfide (4 ml, 67 mmol) at 0° C., and stirred for 30 min at rt. The resulting mixture was then added into methylhydrazine (8 ml, 150 mmol) at 0° C., and stirred for another 2 hours. To this solution was added water (40 ml) and extracted with EtOAc (60 ml×3). The organic solution was concentrated to minimum volume, and subjected to silica gel column chromatography (1:1 ethyl acetate:hexanes; ethyl acetate) to give thiocyclopropyl carboxylic acid N'-methyl hydrazide (2.8 g, 55%). $^1$H NMR (300 MHz, CDCl$_3$): δ 5.21 (br., 2H), 3.62 (s, 3H), 1.91 (m, 1H), 1.25 (m, 2H), 0.98 (m, 2H). ESMS cacld ($C_5H_{10}N_2S$): 130.1; found: 131.1 (M+H)$^+$. To the hydrazide EtOAc solution (2.8 g, 22 mmol, 40 ml) containing TEA (2.2 g, 22 mmol) was added malonyl chloride EtOAc solution (1.6 g, 11 mmol, 4 ml) at 0° C., and the reaction mixture was stirred at rt for 20 min. 20 ml water was added to quench the reaction, and the EtOAc layer was continuously washed twice with water (20 ml×2). The EtOAc solution was concentrated to minimum volume, and subjected to silica gel column chromatography (eluant: 1:1-1:2 hexanes:ethyl acetate) to give SBR-11-5685 (2.1 g, yield: 60%). (2.1 g, yield: 60%). $^1$H NMR (300 MHz, CDCl$_3$): δ 10.01-8.95 (m, 2H), 3.78-3.41 (m, 6H), 2.34-0.82 (m, 10H). ESMS cacld ($C_{13}H_{20}N_4O_2S_2$): 328.1; found: 327 (M–H)$^+$.

Example 13

Preparation of 2-Methylmalonyl-bis(2-Amino-2,3-dihydro-isoindole-1-thione)

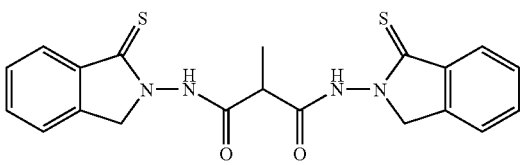

2-carboxybenzaldehyde (150 mg, 1 mmol) and carbazic acid (132 mg, 1 mmol) in 40 ml methanol was stirred at room temperature for 4 h. To this solution was added Pd/C (60 mg, containing 50% H$_2$O), the reaction was under H$_2$ atmosphere for 3 h. The reaction mixture was filtered, and the solvent was evaporated. The resulting residue was subjected to silica gel column chromatography. (eluent: 20% to 50%, EtOAc in hexanes) to obtain 50 mg of product. $^1$H NMR (300 MHz, CDCl$_3$): δ 8.71-7.45 (m, 4H), 4.78 (s, 2H), 1.61 (s, 9H). The resulting product was dissolved in CF$_3$COOH (5 ml), stirred for 30 min. The CF$_3$COOH was evaporated, and the residue was subjected to silica gel column chromatography (eluent: 50% to 0%, hexanes in EtOAc) to give 2-amino-2,3-dihydro-isoindol-1-one (26 mg) as a white solid. $^1$H NMR (300 MHz, CDCl$_3$): δ 7.85-7.39 (m, 4H), 4.54 (s, 2H). MS: 149 (M+H). Subsequent Lawesson's thiolation and DCC coupling with 2-methylmaloic acid under conditions described above afforded 2-methylmalonyl-bis(2-amino-2,3-dihydro-isoindole-1-thione) as a yellow powder. $^1$H NMR (CDCl$_3$) δ 10.35 (s, 2H), 8.21-7.51 (m, 8H), 5.15 (s, 4H), 1.62 (s, 3H); ESMS cacld ($C_{20}H_{18}N_4O_2S_2$): 410.09; found: 411.1 (M+H).

Example 14

The compounds shown below were prepared by the procedures described above. Analytical data is provided for these compounds.

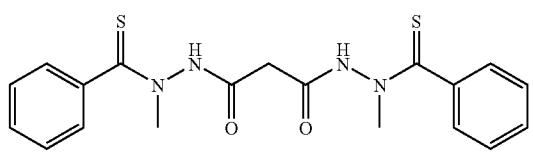

$^1$H NMR (CDCl$_3$) δ 3.1-3.8 (m, 6H), 3.4 (s, 2H), 7.1-7.45 (m, 10H), 9.5-10.5 (m, 1H) ppm; ESMS calcd ($C_{19}H_{20}N_4O_2S_2$): 400.1; found: 399.1 (M–H)$^+$.

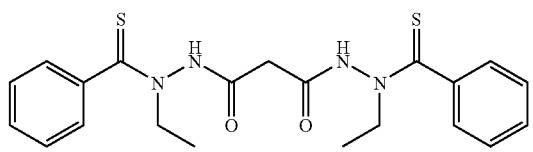

$^1$H NMR (CDCl$_3$) δ 1.0-1.35 (m, 6H), 3.0-4.3 (m, 6H), 7.05-7.40 (m, 10H), 9.1-10.1 (m, 2H); ESMS cacld ($C_{21}H_{24}N_4O_2S_2$): 428.8; found: 427 (M–H)$^+$. Anal Calc For $C_{21}H_{24}N_4O_2S_2$ (428.13) C, 58.85; H, 5.64; N, 13.07; S, 14.96. Found: C, 58.73; H, 5.62; N, 12.97; S, 14.96.

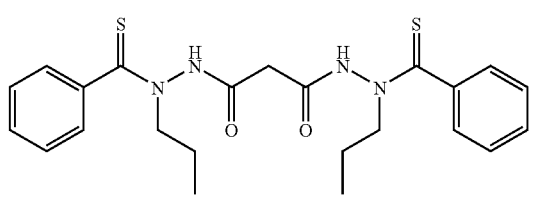

$^1$H NMR (CDCl$_3$) δ 0.7-1.0 (m, 6H), 1.4-1.9 (m, 4H), 3.1-4.2 (m, 6H), 7.1-7.4 (m, 10H), 8.9-10.2 (m, 2H) ppm; ESMS ($C_{23}H_{28}N_4O_2S_2$): 456.1; found: 455.1 (M–H)$^+$.

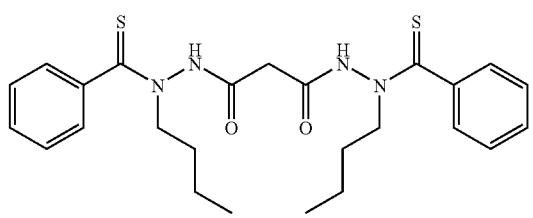

mp 141-143° C.; $^1$H NMR (CDCl$_3$) δ0.6-1.05 (m, 6H), 1.1-1.9 (m, 8H), 3.0-4.2 (m, 6H), 7.0-7.35 (m, 10H), 8.9-11 (ms, 2H). ESMS ($C_{25}H_{32}N_4O_2S_2$): 484.2; found: 483.1

(M−H)⁺. Anal Calc For C₂₅H₃₂N₄O₂S₂ (484.2) C, 61.95; H, 6.65; N, 11.56; S, 13.23. Found: C, 61.98; H, 6.52; N, 11.26; S, 13.16.

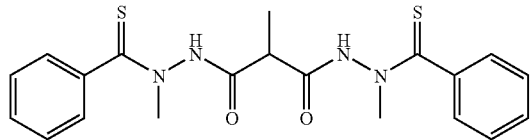

¹H NMR (DMSO-d₆) δ 0.4-0.9 (dd, 3H, J=7), 2.7 (q, 1H), 3.1-3.6 (m, 6H), 7.1-7.5 (m, 10H), 10.9 (br, 2H) ppm; ESMS (C₂₀H₂₂N₄O₂S₂): 414; found: 413 (M−H)⁺.

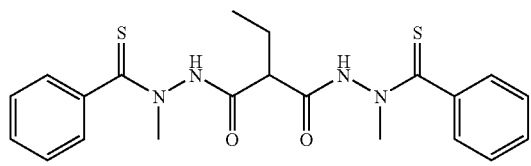

¹H NMR (CDCl₃) δ 0.5 (t, 3H, J=7), 1.1-1.6 (m, 2H), 2.7 (t, 1H, J=7), 3.1-3.3 (m, 6H), 7.0-7.3 (m, 10H), 10.25 (s, 2H) ppm; MS (C₂₁H₂₄N₄O₂S₂): 428.1; found: 427.1 (M−H)⁺.

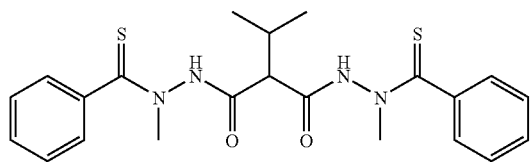

¹H NMR (CDCl₃) δ 0.5 (d, 6H, J=7), 0.9-1.2 (m, 1H), 3.0-41 (m, 7H), 7.1-7.4 (m, 10H), 10.3 (s, 2H) ppm; ESMS (C₂₂H₂₆N₄O₂S₂): 442.1; found: 441.1 (M−H)⁺.

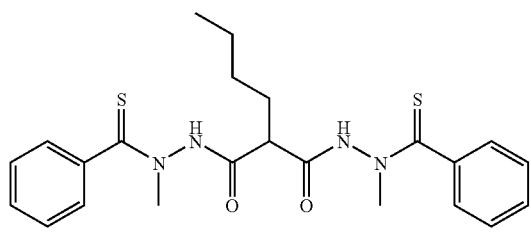

¹H NMR (CDCl₃) δ0.4-1.3 (m, 5H), 1.5-1.8 (m, 2H), 3.0-3.7 (m, 6H), 7.1-7.5 (m, 10H), 11 (s, 2H) ppm; MS (C₂₃H₂₈N₄O₂S₂): 456.1; found: 455.1 (M−H)⁺.

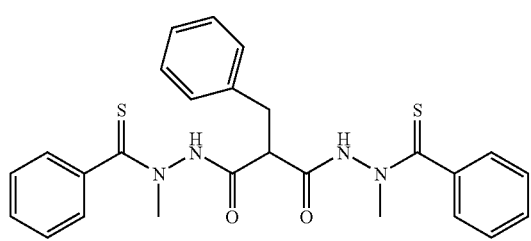

¹H NMR (CDCl₃) δ 2.1 (d, 2H, J=7), 2.9 (t, 1H, J=7), 3.1-3.5 (m, 6H), 6.8-7.4 (m, 15H), 11 (s, 2H) ppm; MS (C₂₆H₂₆N₄O₂S₂): 490.1; found: 489.1 (M−H)⁺.

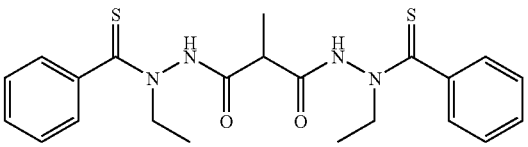

¹H NMR (CDCl₃) δ 0.4 (d, 3H, J=7), 1.0-1.4 (m, 6H), 2.75 (q, 1H), 3.0-4.3 (m, 4H), 7.1-7.4 (m, 10H), 10.6 (s, 2H); ESMS Calc For (C₂₂H₂₆N₄O₂S₂): 442.1; found: 441.1 (M−H)⁺; Anal Calc For C₂₂H₂₆N₄O₂S₂ (442.15) C, 59.70; H, 5.92; N, 12.66; S, 14.49. Found: C, 59.64; H, 5.92; N, 12.59; S, 14.47.

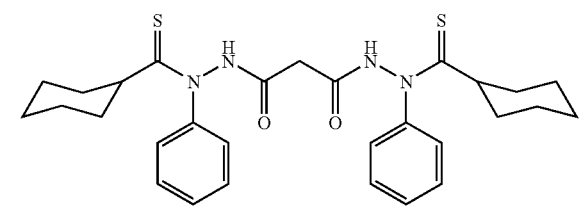

¹H NMR (DMSO-d₆) δ 0.9-1.8 m, 22H), 3.1-3.5 (m, 2H), 7.2-7.6 (m, 10H), 11.1-11.7 (ms, 2H) ppm; ESMS calcd (C₂₉H₃₆N₄O₂S₂): 536.3; found: 537.3 (M−H)⁺.

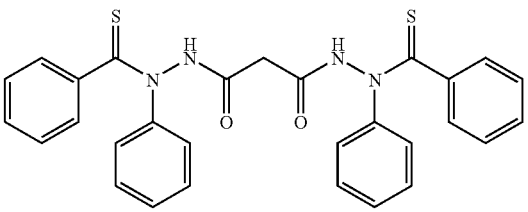

¹H NMR (DMSO-d₆) δ 3.20 (br, 2H), 7.1-7.6 (m, 20H), 11.5 (s, 2H) ppm; ESMS calcd (C₂₉H₂₄N₄O₂S₂): 524.1; found: 523.1 (M−H)⁺.

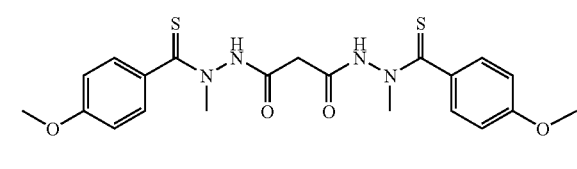

¹H NMR (CDCl₃) δ 3.0-4.3 (m, 14H), 6.6-7.5 (m, 8H), 10.4 (s, 2H) ppm; ESMS calcd (C₂₁H₂₄N₄O₂S₂): 460.2; found: 461.2 (M+H)⁺.

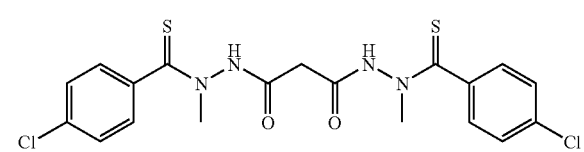

¹H NMR (CDCl₃) δ 2.65-3.60 (m, 8H), 7.2-7.4 (m, 8H), 11.1 (br, 2H); ESMS calcd (C₁₉H₁₈Cl₂N₄O₂S₂): 468.0; found: 467.9 (M−H)⁺.

¹H NMR (acetone-d₆) δ 3.5 (s, 2H), 6.45 (d, 2H, J=5), 6.9 (d, 2H, J=5), 7.2-7.6 (m, 12H), 10.6 (s, 2H) ppm; ESMS calcd (C₂₅H₂₀N₄O₄S₂): 504.1; found: 503.1 (M−H)⁺.

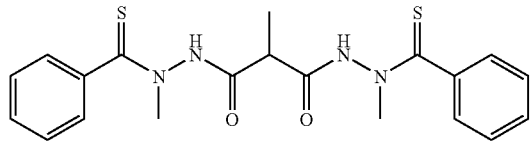

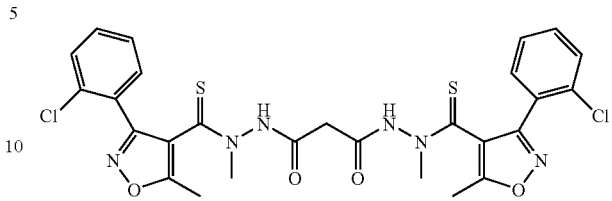

¹H NMR (CDCl₃) δ 0.4 (d, 3H, J=7), 2.7 (q, 1H, J=7), 3.0-3.8 (m, 6H), 7.2-8.2 (m, 8H), 10.5-10.7 (ms, 2H) ppm; ESMS calcd (C₂₀H₂₀Cl₂N₄O₂S₂): 482.0; found: 481.0 (M−H)⁺.

¹H NMR (DMSO-d₆) δ 2.60 (s, 6H), 3.05 (s, 6H), 3.40 (s, 2H), 7.15-7.50 (m, 8H) ppm; ESMS calcd (C₂₇H₂₄Cl₂N₆O₄S₂): 630.1; found: 629.1 (M−H)⁺.

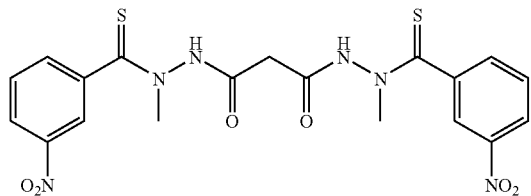

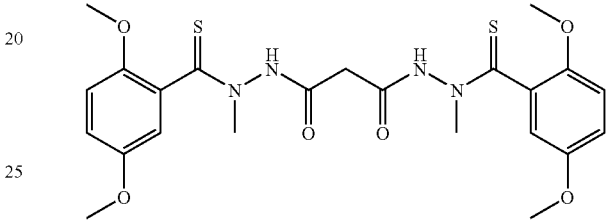

¹H NMR (CDCl₃) δ 2.9-3.8 (m, 6H), 7.3-7.7 (m, 4H), 8.0-8.3 (m, 4H), 10.9 (s, 2H); ESMS calcd (C₁₉H₁₈N₆O₆S₂): 490.0; found: 489.0 (M−H)⁺.

¹H NMR (CDCl₃) δ 10.06-8.82 (2H), 7.16-6.81 (m, 6H), 4.01-3.81 (m, 6H), 3.78-3.11 (m, 6H), 2.81-2.58 (m, 2H): ESMS cacld (C₂₃H₂₈N₄O₆S₂): 520.15; found: 521 (M+H).

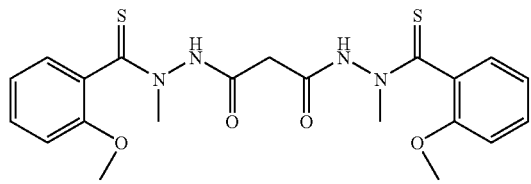

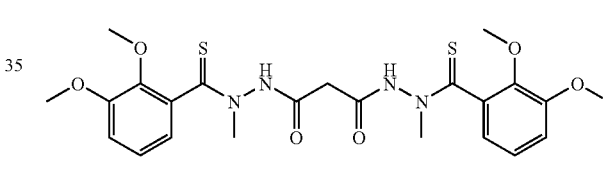

¹H NMR (CDCl₃) δ 3.1-3.9 (m, 14H), 6.7-7.8 (m, 8H), 9.0-10 (m, 2H) ppm; ESMS calcd (C₂₁H₂₄N₄O₄S₂): 460.1; found: 459.1 (M−H)⁺.

¹H NMR (CDCl₃) δ 10.38-9.01 (2H), 7.12-6.82 (m, 6H), 3.92-3.78 (m, 12H), 3.75-3.06 (m, 6H), 2.61-2.51 (m, 2H); ESMS cacld (C₂₃H₂₈N₄O₆S₂): 520.15; found: 521 (M+H).

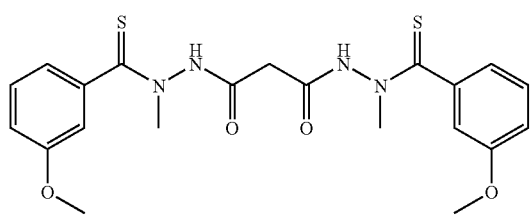

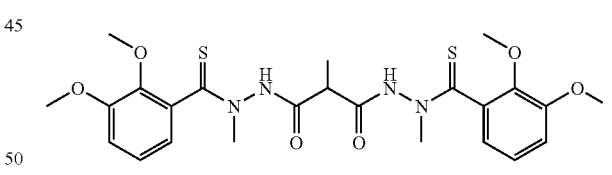

(SBR-11-5032): ¹H NMR (CDCl₃) δ 3.0-3.9 (m, 14H), 6.7-7.3 (m, 8H), 9.0-10 (m, 2H) ppm; ESMS calcd (C₂₁H₂₄N₄O₄S₂): 460.1; found: 459.1 (M−H)⁺.

¹H NMR (CDCl₃) δ 9.45-8.63 (2H), 7.18-6.81 (m, 6H), 4.01-3.80 (m, 6H), 3.78-3.24 (m, 6H), 2.62-2.50 (m, 1H), 1.74-0.11 (m, 3H); ESMS cacld (C₂₄H₃₀N₄O₆S₂): 534.16; found: 535 (M+H).

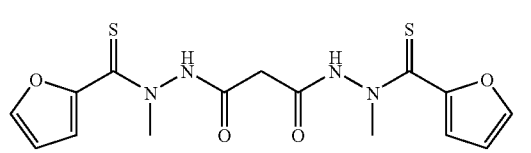

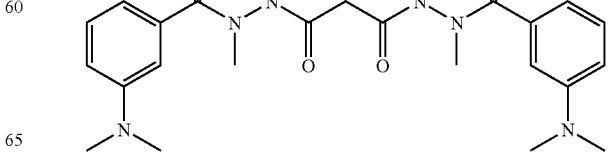

$^1$H NMR (CDCl$_3$) δ 10.19-8.61 (2H), 7.26-6.52 (m, 6H), 3.81-3.08 (m, 8H), 3.01-2.88 (m, 12H). ESMS cacld (C$_{23}$H$_{30}$N$_6$O$_2$S$_2$): 486.19; found: 487 (M+H).

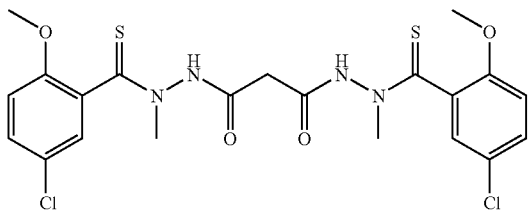

$^1$H NMR (CDCl$_3$) δ 9.92-8.80 (2H), 7.41-6.72 (m, 6H), 4.01-3.81 (m, 6H), 3.80-3.15 (m, 6H), 2.76-2.42 (m, 2H); ESMS cacld (C$_{21}$H$_{22}$Cl$_2$N$_4$O$_4$S$_2$): 528.05; found: 529 (M+H).

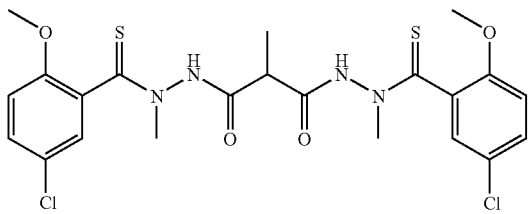

$^1$H NMR (CDCl$_3$) δ 10.21-9.02 (2H), 7.60-6.81 (m, 6H), 4.14-3.88 (m, 6H), 3.87-3.18 (m, 6H), 2.84-2.65 (m, 1H), 1.10-0.16 (m, 3H); ESMS cacld (C$_{22}$H$_{24}$Cl$_2$N$_4$O$_4$S$_2$): 542.06; found: 543 (M+H).

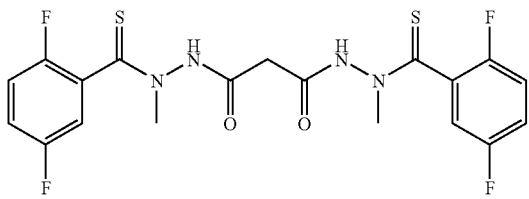

$^1$H NMR (CDCl$_3$) δ 10.02-9.20 (2H), 7.63-7.01 (m, 6H), 4.21-3.22 (m, 6H), 1.88-1.36 (m, 2H); ESMS cacld (C$_{19}$H$_{16}$F$_4$N$_4$O$_2$S$_2$): 472.07; found: 473 (M+H).

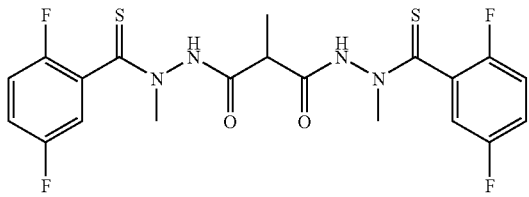

$^1$H NMR (CDCl$_3$) δ 7.93-7.61 (2H), 7.40-6.92 (m, 6H), 3.98-3.41 (m, 6H), 2.19-0.93 (m, 4H); ESMS cacld (C$_{20}$H$_{18}$F$_4$N$_4$O$_2$S$_2$): 486.08; found: 487 (M+H).

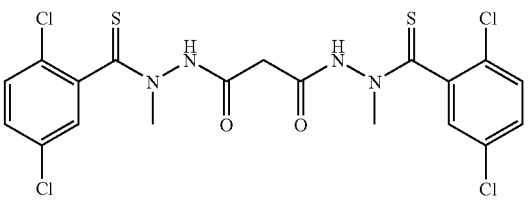

$^1$H NMR (CDCl$_3$) δ 10.12-9.21 (2H), 7.67-7.23 (m, 6H), 3.94-3.22 (m, 6H), 2.01-1.21 (m, 2H); ESMS cacld (C$_{19}$H$_{16}$Cl$_4$N$_4$O$_2$S$_2$): 535.95; found: 537 (M+H).

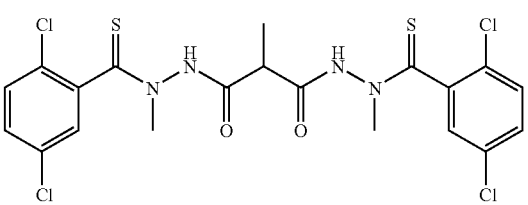

$^1$H NMR (CDCl$_3$) δ 7.78-7.23 (2H), 4.56-3.10 (m, 6H), 2.34-1.12 (m, 4H); ESMS cacld (C$_{20}$H$_{18}$Cl$_4$N$_4$O$_2$S$_2$): 549.96; found: 551 (M+H).

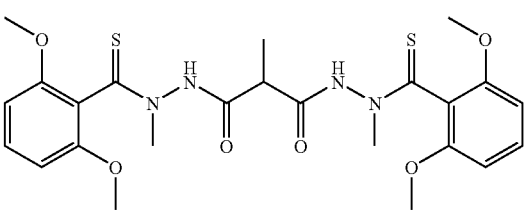

$^1$H NMR (CDCl$_3$) δ 9.92-9.01 (2H), 7.38-7.15 (m, 3H), 6.66-6.51 (m, 3H), 3.98-3.75 (m, 12H), 3.72-3.21 (m, 6H), 2.01-0.42 (m, 4H); ESMS cacld (C$_{24}$H$_{30}$N$_4$O$_6$S$_2$): 534.16; found: 535 (M+H).

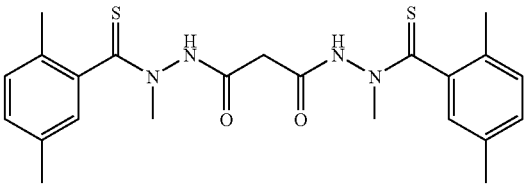

$^1$H NMR (CDCl$_3$) δ 10.51-9.82 (2H), 7.42-6.80 (m, 6H), 3.92-3.04 (m, 6H), 2.60-1.21 (m, 14H); ESMS cacld (C$_{23}$H$_{28}$N$_4$O$_2$S$_2$): 456.17; found: 457 (M+H).

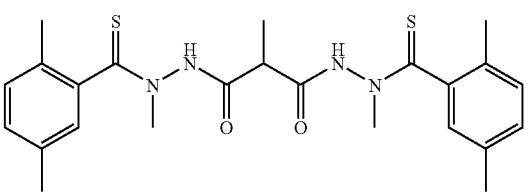

¹H NMR (CDCl₃) δ 10.51-8.82 (2H), 7.11-6.89 (m, 6H), 3.81-3.02 (m, 6H), 2.40-1.02 (m, 16H); ESMS cacld (C₂₄H₃₀N₄O₂S₂): 470.18; found: 471 (M+H).

¹H NMR (CDCl₃) δ 9.81-8.79 (2H), 7.01-6.64 (m, 6H), 4.21-3.81 (m, 8H), 3.80-3.22 (m, 6H), 1.54-1.20 (m, 13H), 1.01-0.16 (m, 3H); ESMS cacld (C₂₈H₃₈N₄O₆S₂): 590.22; found: 591 (M+H).

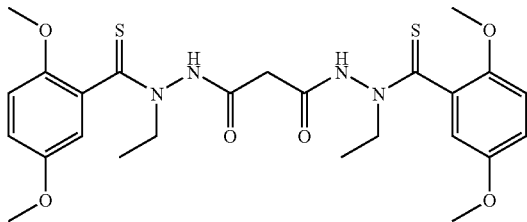

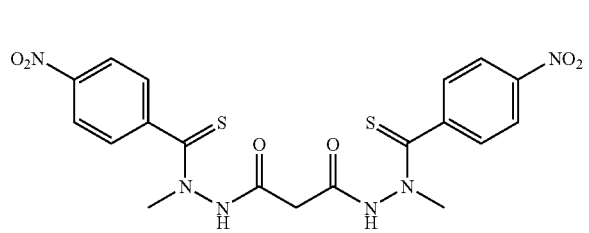

¹H NMR (CDCl₃) δ 9.86-8.42 (2H), 7.01-6.6 (m, 6H), 4.18-3.51 (m, 16H), 3.22-2.26 (2H), 1.40-1.04 (m, 6H); ESMS cacld (C₂₅H₃₂N₄O₆S₂): 548.18; found: 547 (M-H).

¹H NMR (DMSO-d₆): δ 8.25 (d, J=8.1 Hz, 4H), 7.50 (d, J=8.1 Hz, 4H), 3.7-3.3 (m, 8H); ESMS cacld for C₁₉H₁₈N₆O₆S₂: 490.1; Found: 489.0 (M-H).

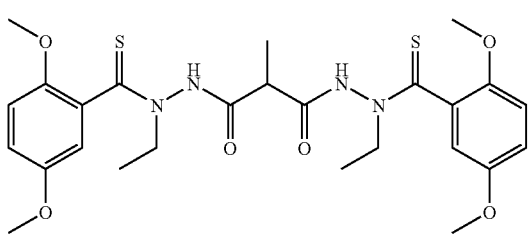

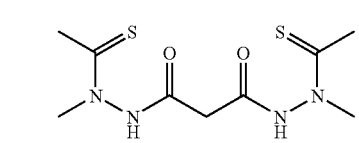

¹H NMR (CDCl₃): δ 3.6-3.4 (m, 8H), 2.7-2.5 (m, 6H); ESMS cacld for C₉H₁₆N₄O₂S₂: 276.1; Found: 274.9 (M-H).

¹H NMR (CDCl₃) δ 9.99-8.41 (2H), 7.01-6.68 (m, 6H), 4.18-3.56 (m, 16H), 1.40-0.02 (m, 10H); ESMS cacld (C₂₆H₃₄N₄O₆S₂): 562.19; found: 561 (M-H).

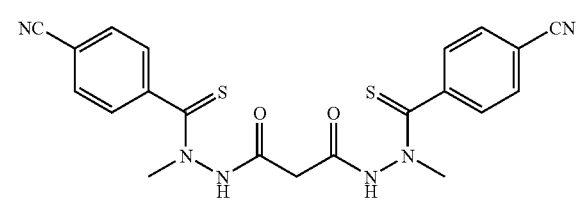

¹H NMR (CDCl₃): δ 10.25 (m, 2H), 7.7-7.4 (m, 8H), 3.7 (m, 2H), 3.35 (m, 6H); ESMS cacld for C₂₁H₁₈N₆O₂S₂: 450.1; Found: 449.0 (M-H).

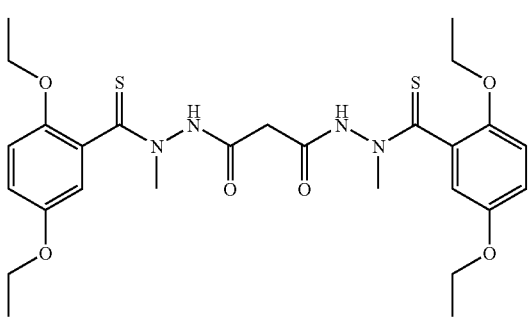

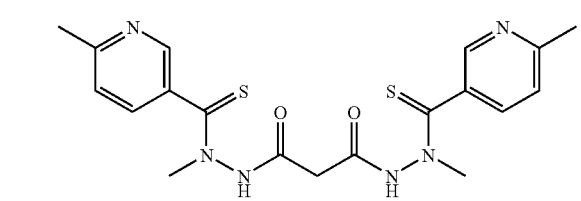

¹H NMR (CDCl₃) δ 10.12-8.82 (2H), 7.03-6.62 (m, 6H), 4.21-3.87 (m, 8H), 3.84-3.01 (m, 6H), 2.71-2.42 (m, 2H), 1.56-1.21 (m, 12H); ESMS cacld (C₂₇H₃₆N₄O₆S₂): 576.21; found: 577 (M+H).

¹H NMR (CDCl₃): δ 8.2 (s, 2H), 7.7-7.5 (m, 4H), 3.7-3.4 (m, 8H), 2.9-2.8 (m, 6H); ESMS cacld for C₁₉H₂₂N₆O₂S₂: 430.1; Found: 431.1 (M+H).

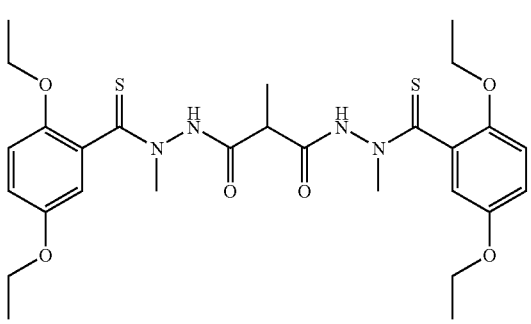

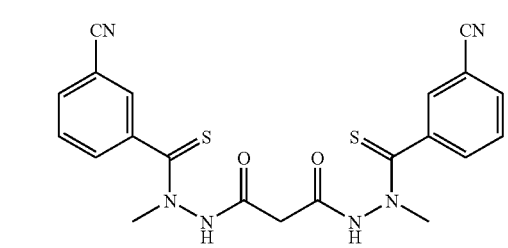

¹H NMR (CDCl₃): δ 10.0-9.2 (m, 2H), 7.9-7.45 (m, 8H), 4.0-3.4 (m, 8H); ESMS cacld for C₂₁H₁₈N₆O₂S₂: 450.1; Found: 451.0 (M+H).

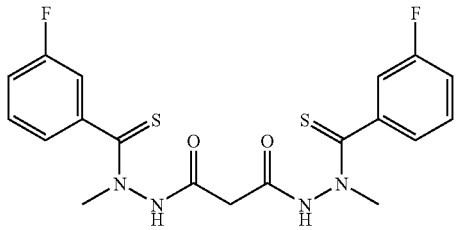

¹H NMR (CDCl₃): δ 10.1-9.4 (2H), 7.5-7.2 (m, 8H), 3.9-3.3 (m, 8H); ESMS cacld for C₁₉H₁₈F₂N₄O₂S₂: 436.1; Found: 437.1 (M+H).

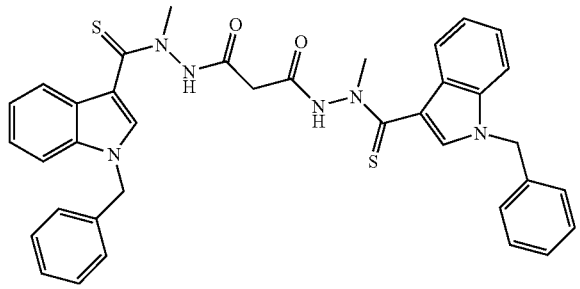

¹H NMR (CDCl₃): δ 3.3 (s, 2H), 3.6 (s, 6H), 5.25 (s, 4H), 7.05-7.3 (m, 16H), 7.6 (s, 2H), 7.9 (d, 2H, J=6), 10.56 (s, 2H) ppm; ESMS calcd (C₃₇H₃₄N₆O₂S₂): 658.2; found: 659.2 (M+H)⁺.

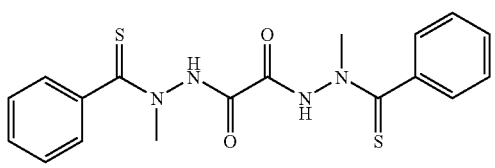

¹H NMR (DMSO) δ 11.98 (2H), 7.44-7.12 (m, 10H), 3.69-3.14 (s, 6H). ESMS cacld (C₂₈H₁₈N₄O₂S₂): 386.09: found: 387.1 (M+H).

¹H NMR (CHCl₃) δ 9.48-8.55 (2H), 7.56-7.20 (m, 10H), 3.80-3.31 (m, 6H), 2.88-2.22 (m, 4H). ESMS cacld (C₂₀H₂₂N₄O₂S₂): 414.12; found: 415.1 (M+H).

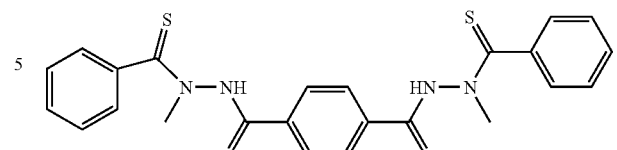

¹H NMR (300 MHz, CDCl₃) δ 10.21-9.91 (m, 2H), 8.06-7.32 (m, 14H), 3.91-3.56 (m, 6H). ESMS cacld (C₂₄H₂₂N₄O₂S₂): 462.12; found: 463 (M+H).

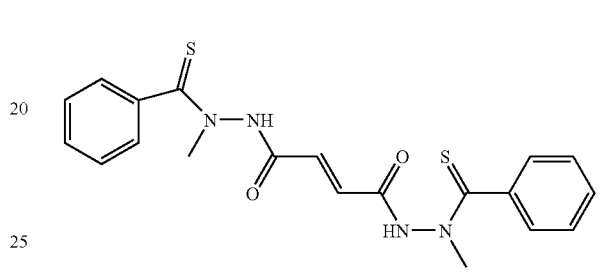

¹H NMR (300 MHz, DMSO-d₆) δ 11.60-11.40 (m, 2H), 7.48-6.46 (m, 12H), 3.64-3.3.30 (m, 6H). ESMS cacld (C₂₀H₂₀N₄O₂S₂): 412.10; found: 413 (M+H).

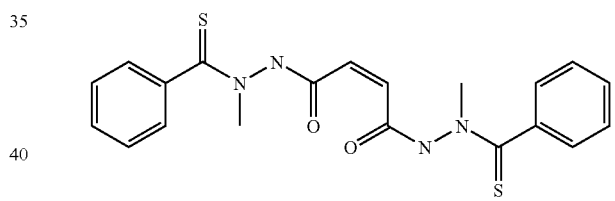

¹H NMR (300 MHz, CDCl₃) δ 7.58-7.20 (m, 12H), 3.68-3.20 (m, 6H). ESMS cacld (C₂₀H₂₀N₄O₂S₂): 412.10; found: 413 (M+H).

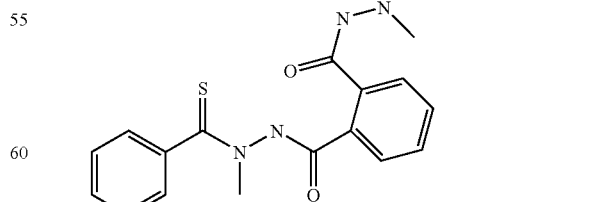

¹H NMR (300 MHz, CDCl₃) δ 9.65-8.70 (2H), 8.01-7.21 (m, 14H), 3.84-3.40 (m, 6H). ESMS cacld (C₂₄H₂₂N₄O₂S₂): 462.12: found: 463 (M+H).

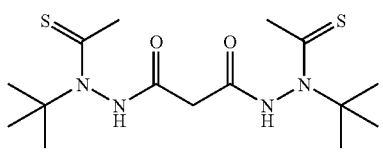

¹H NMR (CDCl₃): δ 2.63 (s, 2H); 2.18 (s, 6H); 1.25 (s, 18H). MS calcd for $C_{15}H_{28}N_4O_2S_2$: 360.2; Found: 383.1 (M+Na).

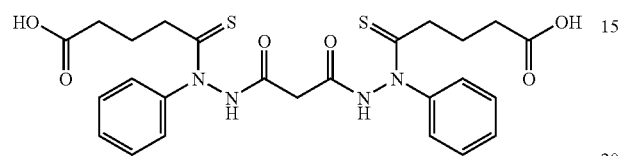

¹H NMR (CDCl₃): δ 7.3 (m, 10H); 3.2 (m, 2H); 2.45 (t, J=7.4 Hz, 4H); 2.21 (t, J=7.4 Hz, 4H); 1.90 (m, 8H). MS calcd for $C_{25}H_{28}N_4O_6S_2$: 544.15; Found: 567.2 (M+Na).

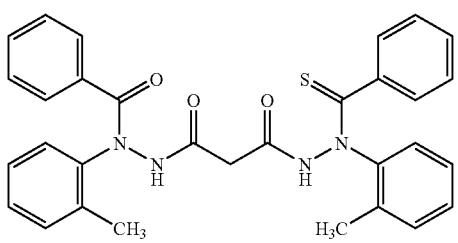

¹H NMR (CDCl₃): δ 7.4-1 (m, 18H); 3.3 (br s, 2H); 2.5 (br s, 6H). MS calcd for $C_{31}H_{28}N_4O_3S$: 536.2: Found: 537.2 (M+H).

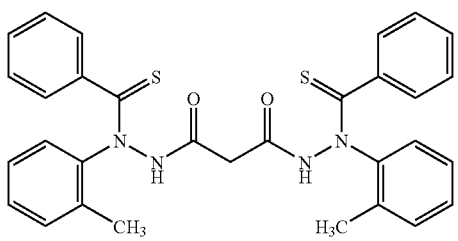

¹H NMR (CDCl₃): δ 7.2 (m, 18H); 3.5 (br s, 2H); 2.4 (br s, 6H). MS calcd for $C_{31}H_{28}N_4O_2S_2$: 552.2: Found: 553.2 (M+H).

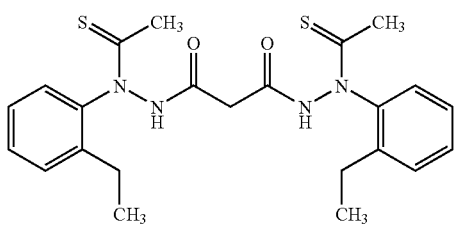

¹H NMR (CDCl₃): δ 7.8-7.4 (br s, 8H), 3.75-3.5 (m, 2H), 3.95-3.8 (m, 4H), 2.58 (s, 6H), 1.4 (m, 6H). ESMS cacld for $C_{23}H_{28}N_4O_2S_2$: 456.2; Found: 479.2 (M+Na).

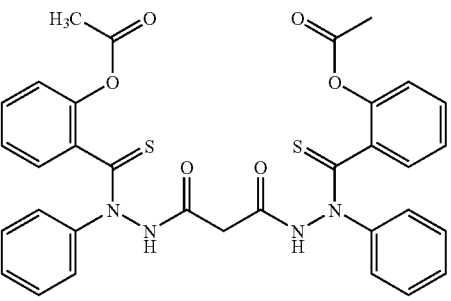

¹H NMR (CDCl₃): δ 7.5 (br s, 18H), 3.4 (br s, 2H), 2.45 (s, 6H). ESMS cacld for $C_{33}H_{28}N_4O_6S_2$: 640.1; Found 641.1 (M+H).

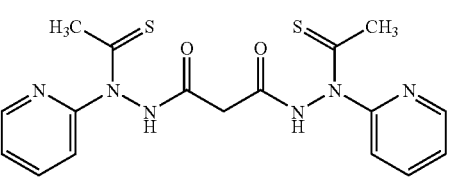

¹H NMR (CDCl₃): δ 8.3-8.05 (m, 4H), 7.75 (t, J=8.0 Hz, 2H), 7.1 (br s, 2H), 3.74 (s, 2H), 2.38 (s, 6H). ESMS cacld for $C_{17}H_{18}N_6O_2S_2$: 402.1. Found: 403.1 (M+H).

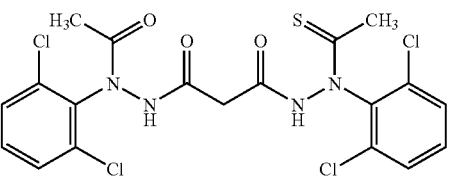

¹H NMR (CDCl₃): δ 7.7-7.2 (m, 6H), 3.2 (s, 2H), 2.58 (s, 3H), 2.15 (s, 3H). ESMS cacld for $C_{19}H_{16}Cl_4N_4O_3S$: 519.9; Found: 520.9 (M+H).

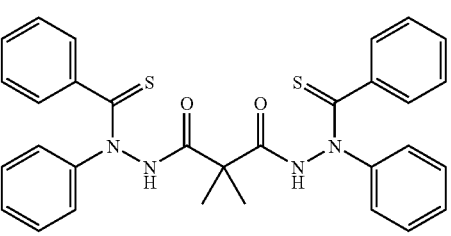

¹H NMR (CDCl₃-D₂O): δ 7.45-7.15 (m, 20H), 1.6 (br s, 6H). ESMS cacld for $C_{31}H_{28}N_4O_2S_2$: 552.2; Found: 553.2 (M+H).

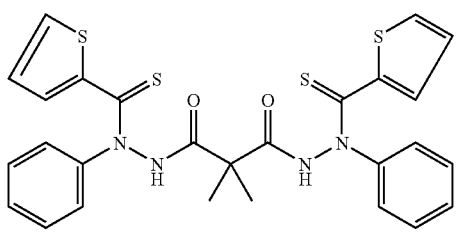

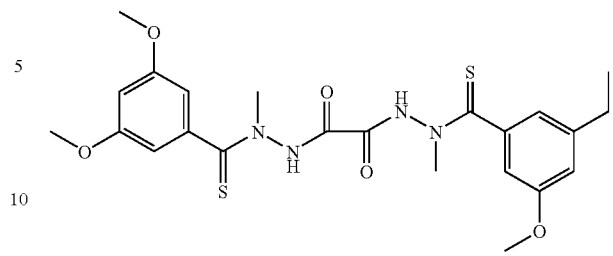

¹H NMR (DMSO-d₆): δ 11.3 (s, 2H), 7.75 (d, J=6.0 Hz, 2H), 7.5-7.4 (m, 12H); 6.9 (m, 2H); ESMS cacld for $C_{27}H_{24}N_4O_2S_4$: 564.1; Found: 565.2 (M+H).

¹H NMR (300 MHz, CDCl₃): δ 10.60-9.41 (m, 2H), 7.15-6.23 (m, 6H), 3.89-3.28 (m, 6H), 3.76 (S, 12H). ESMS cacld ($C_{22}H_{28}N_4O_6S_2$): 506.13; found: 507 (M+H).

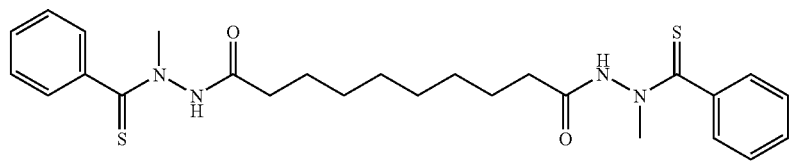

¹H NMR (300 MHz, DMSO): δ 7.40-7.12 (m, 10H), 3.70-2.80 (m, 6H), 1.84-0.72 (m, 16H). ESMS cacld ($C_{26}H_{34}N_4O_2S_2$): 498.21; found: 499 (M+H).

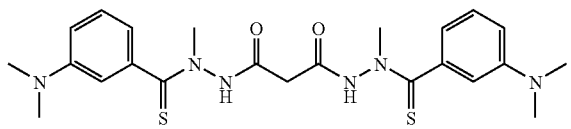

¹H NMR (300 MHz, CDCl₃): δ 10.18-8.60 (m, 2H), 7.26-6.46 (m, 8H), 3.80-3.02 (m, 6H), 3.00-2.80 (m, 12H). 1.78-1.56 (m, 2H). ESMS cacld ($C_{23}H_{30}N_4O_2S_2$): 486.19; found: 487 (M+H).

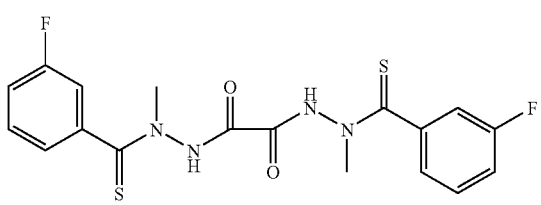

¹H NMR (300 MHz, CDCl₃): δ 10.42-9.53 (m, 2H), 7.55-6.87 (m, 8H), 3.99-3.28 (m, 6H), ESMS cacld ($C_{18}H_{10}N_4F_2O_2S_2$): 422.07; found: 423 (M+H).

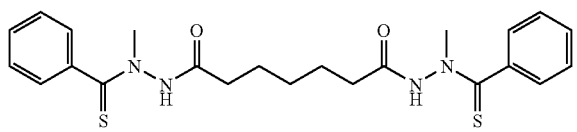

¹H NMR (300 MHz, DMSO): δ 10.90-10.81 (m, 2H), 7.50-7.21 (m, 10H), 3.78-3.36 (m, 6H), 2.64-0.50 (m, 10H). ESMS cacld ($C_{20}H_{28}N_4O_2S_2$): 456.17; found: 457 (M+H).

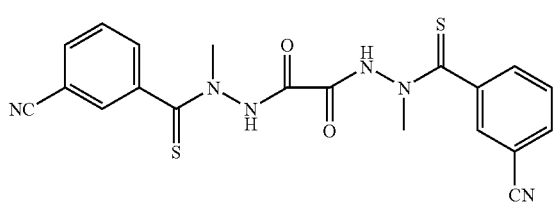

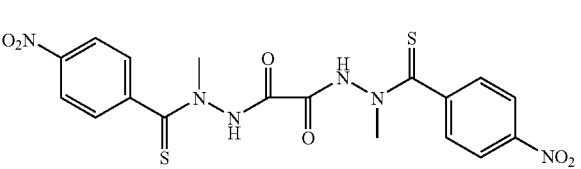

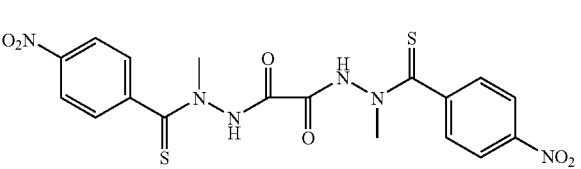

¹H NMR (300 MHz, CDCl₃): δ 10.00-9.71 (m, 2H), 7.72-7.21 (m, 8H), 3.80-3.26 (m, 6H). ESMS cacld ($C_{20}H_{16}N_6O_2S_2$): 436.08; found: 437 (M+H).

¹H NMR (300 MHz, DMSO): δ 12.08 (br. 2H), 8.27-7.24 (m, 8H), 3.70-3.15 (m, 6H). ESMS cacld ($C_{18}H_{16}N_6O_6S_2$): 476.06; found: 477 (M+H).

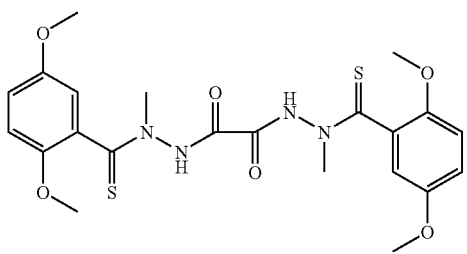

¹H NMR (300 MHz, CDCl₃): δ 10.12-9.83 (m, 2H), 7.15-6.63 (m, 6H), 3.99-2.91 (m, 6H), ESMS cacld (C$_{22}$H$_{26}$N$_4$O$_6$S$_2$): 506.13; found: 507 (M+H).

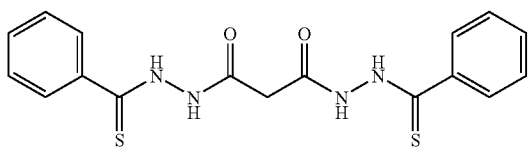

¹H NMR (300 MHz, DMSO): δ 11.12-10.54 (m, 2H), 8.27-7.18 (m, 10H), 4.26-3.72 (m, 2H), 3.37-3.18 (m, 2H). ESMS cacld (C$_{17}$H$_{16}$N$_4$O$_2$S$_2$): 372.07; found: 371 (M−H).

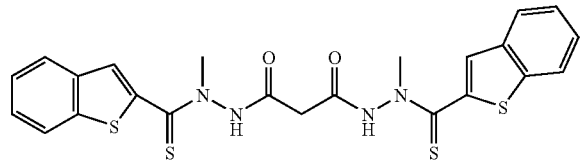

¹H NMR (300 MHz, DMSO): δ 11.52 (br, 2H), 7.95-7.33 (m, 10H), 3.42-3.22 (m, 6H), 2.48 (m, 2H). ESMS cacld (C$_{23}$H$_{20}$N$_4$O$_2$S$_4$): 512.05; found: 513 (M+H).

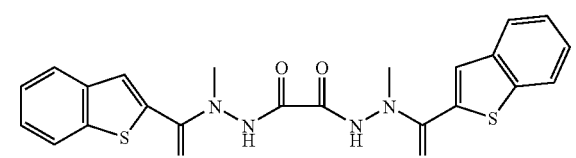

¹H NMR (300 MHz, CDCl₃): δ 7.81-7.28 (m, 8H), 3.82 (s, 6H). ESMS cacld (C$_{22}$H$_{18}$N$_4$O$_2$S$_4$): 498.03; found: 499 (M+H).

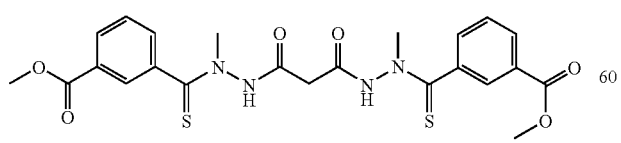

¹H NMR (300 MHz, CDCl₃): δ 10.02-9.11 (m, 2H), 8.16-7.28 (m, 8H), 3.99-3.08 (m, 6H), 2.90-1.20 (m, 2H). ESMS cacld (C$_{23}$H$_{24}$N$_4$O$_6$S$_2$): 516.11; found: 517 (M+H).

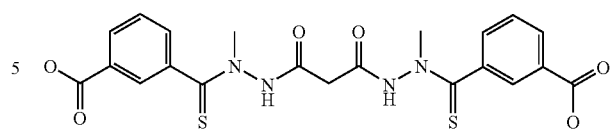

¹H NMR (300 MHz, DMSO): δ 7.99 (m, 8H), 8.16-7.28 (m, 8H), 3.80-3.14 (m, 6H), 1.80-1.21 (m, 2H). ESMS cacld (C$_{21}$H$_{20}$N$_4$O$_6$S$_2$): 488.08; found: 487 (M−H).

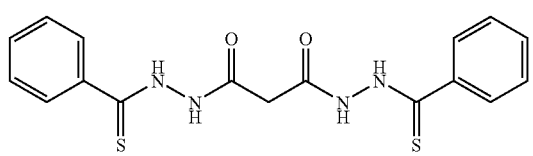

¹H NMR (300 MHz, CDCl₃): δ 10.82-10.55 (m, 2H), 7.91-7.29 (m, 10H), 3.64-3.11 (m, 6H), 1.90-1.40 (m, 2H). ESMS cacld (C$_{19}$H$_{20}$N$_4$O$_2$S$_2$): 400.19; found: 399 (M−H).

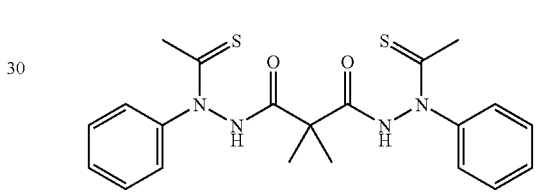

¹H NMR (CDCl₃): δ 7.38 (m, 10H), 2.40 (s, 6H), 1.5-1.6 (6H); ESMS cacld for C$_{21}$H$_{24}$N$_4$O$_2$S$_2$: 564.1; Found: 565.2 (M+H).

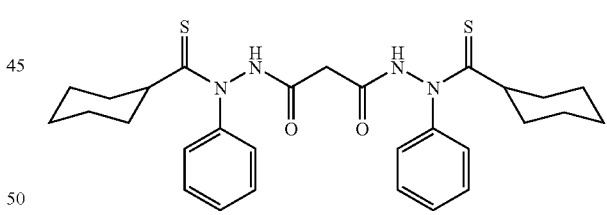

¹H NMR (DMSO-d₆) δ 0.9-1.8 m, 22H), 3.1-3.5 (m, 2H), 7.2-7.6 (m, 10H), 11.1-11.7 (ms, 2H) ppm; ESMS calcd (C$_{29}$H$_{36}$N$_4$O$_2$S$_2$): 536.3; found: 537.3 (M−H)⁺.

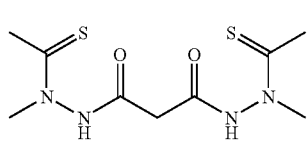

¹H NMR (CDCl₃): δ 3.6-3.4 (m, 8H), 2.7-2.5 (m, 6H); ESMS cacld for C$_9$H$_{16}$N$_4$O$_2$S$_2$: 276.1; Found: 274.9 (M−H)⁺.

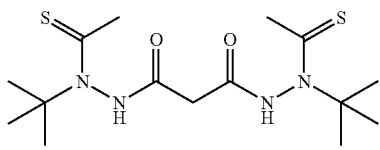

¹H NMR (CDCl₃): δ 2.63 (s, 2H); 2.18 (s, 6H); 1.25 (s, 18H). MS calcd for C₁₅H₂₈N₄O₂S₂: 360.2; Found: 383.1 (M+Na)⁺.

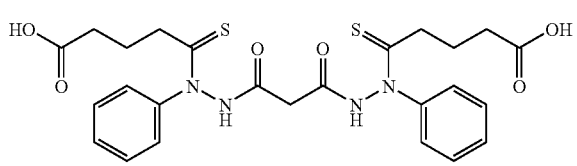

¹H NMR (CDCl₃): δ 7.3 (m, 10H); 3.2 (m, 2H); 2.45 (t, J=7.4 Hz, 4H); 2.21 (t, J=7.4 Hz, 4H); 1.90 (m, 8H). MS calcd for C₂₅H₂₈N₄O₆S₂: 544.15; Found: 567.2 (M+Na)⁺.

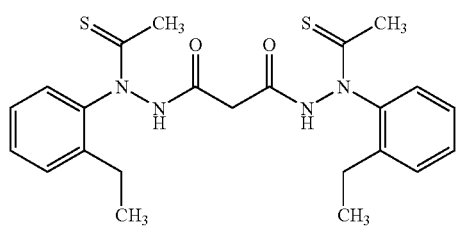

¹H NMR (CDCl₃): δ 7.8-7.4 (br s, 8H), 3.75-3.5 (m, 2H), 3.95-3.8 (m, 4H), 2.58 (s, 6H), 1.4 (m, 6H). ESMS cacld for C₂₃H₂₈N₄O₂S₂: 456.2; Found: 479.2 (M+Na).

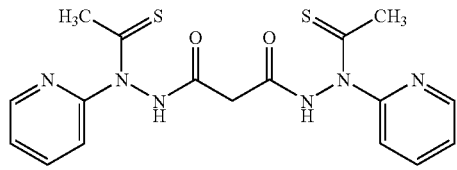

¹H NMR (CDCl₃): δ 8.3-8.05 (m, 4H), 7.75 (t, J=8.0 Hz, 2H), 7.1 (br s, 2H), 3.74 (s, 2H), 2.38 (s, 6H). ESMS cacld for C₁₇H₁₈N₆O₂S₂: 402.1. Found: 403.1 (M+H)⁺.

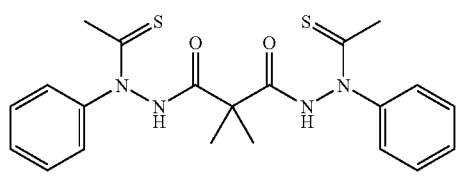

¹H NMR (CDCl₃): δ 7.38 (m, 10H), 2.40 (s, 6H), 1.5-1.6 (6H); ESMS cacld for C₂₁H₂₄N₄O₂S₂: 564.1; Found: 565.2 (M+H)⁺.

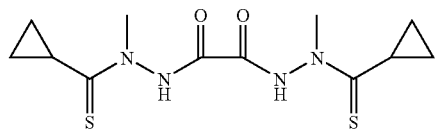

¹H NMR (300 MHz, DMSO): δ 11.95 (s, 2H), 7.48-7.07 (m, 10H), 3.52 (s, 6H). ESMS cacld (C₁₈H₁₈N₄O₂S₂): 386.09; found: 387 (M+H)⁺.

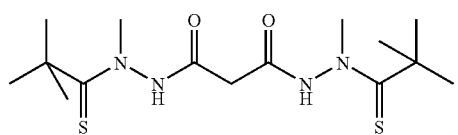

¹H NMR (300 MHz, CDCl₃): δ 9.66-8.83 (m, 2H), 3.73-3.23 (m, 6H), 2.10-1.20 (m, 20H). ESMS cacld (C₁₅H₂₈N₄O₂S₂): 360.17; found: 359 (M−H)⁺.

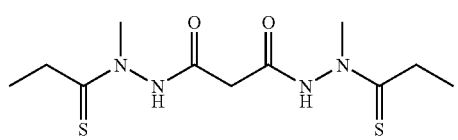

¹H NMR (300 MHz, CDCl₃): δ 3.66-3.42 (m, 6H), 2.84-2.58 (m, 4H), 1.40-1.19 (m, 6H). ESMS cacld (C₁₁H₂₀N₄O₂S₂): 304.10; found: 303 (M−H)⁺.

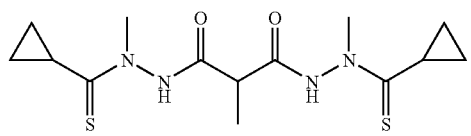

¹H NMR (300 MHz, CDCl₃): δ 4.15-3.40 (m, 6H), 2.00-1.01 (m, 14H). ESMS cacld (C₁₄H₂₂N₄O₂S₂): 342.12; found: 341 (M−H)⁺.

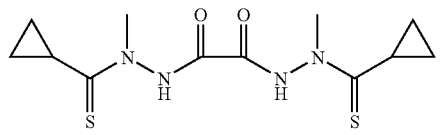

¹H NMR (300 MHz, CDCl₃): δ 3.90-3.18 (m, 6H), 2.11-0.91 (m, 10H). ESMS cacld (C₁₂H₁₈N₄O₂S₂): 314.09; found: 313 (M−H)⁺.

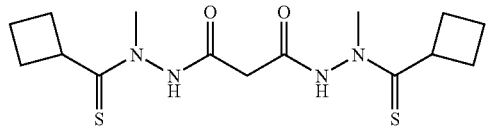

$^1$H NMR (300 MHz, CDCl$_3$): δ 10.08-9.01 (m, 2H), 3.68-3.20 (m, 6H), 2.59-1.12 (m, 16H). ESMS cacld (C$_{15}$H$_{24}$N$_4$O$_2$S$_2$): 356.13; found: 355 (M–H)$^+$.

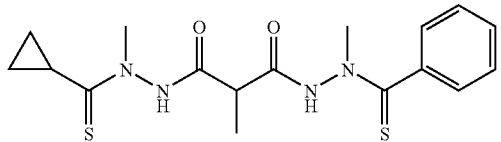

$^1$H NMR (300 MHz, CDCl$_3$): δ 10.22-9.41 (m, 2H), 7.48-7.20 (m, 5H), 3.82-3.02 (m, 6H), 2.38-0.82 (m, 7H). ESMS cacld (C$_{16}$H$_{20}$N$_4$O$_2$S$_2$): 364.10; found: 363 (M–H)$^+$.

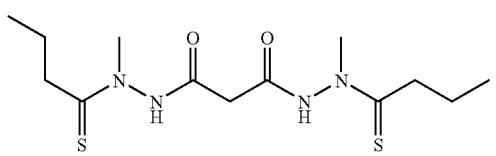

$^1$H NMR (300 MHz, CDCl$_3$): δ 10.03-9.02 (m, 2H), 3.71-3.42 (m, 6H), 2.80-0.81 (m, 16H). ESMS cacld (C$_{13}$H$_{24}$N$_4$O$_2$S$_2$): 332.13; found: 331 (M–H)$^+$.

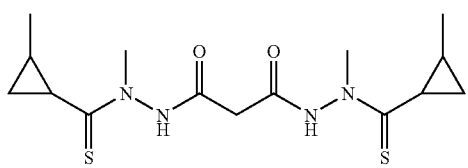

$^1$H NMR (300 MHz, CDCl$_3$): δ 3.78-3.08 (m, 6H), 1.90-0.81 (m, 18H). ESMS cacld (C$_{15}$H$_{24}$N$_4$O$_2$S$_2$): 356.13; found: 355 (M–H)$^+$.

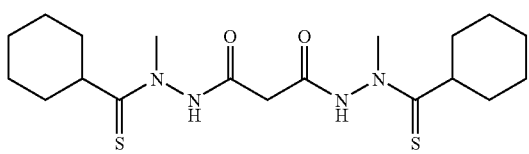

$^1$H NMR (300 MHz, CDCl$_3$): δ 10.00-8.79 (m, 2H), 3.65-3.07 (m, 6H), 2.79-1.08 (m, 24H). ESMS cacld (C$_{19}$H$_{32}$N$_4$O$_2$S$_2$): 412.20; found: 411 (M–H)$^+$.

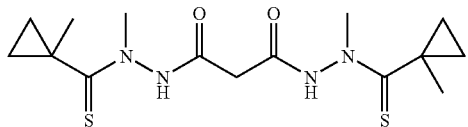

$^1$H NMR (300 MHz, CDCl$_3$): δ 9.79 (br, 2H), 3.79-3.41 (m, 6H), 1.60-0.75 (m, 18H). ESMS cacld (C$_{15}$H$_{24}$N$_4$O$_2$S$_2$): 356.13; found: 355 (M–H)$^+$.

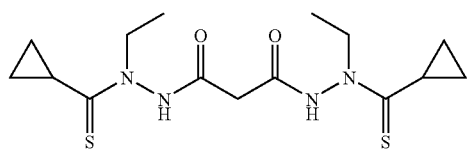

$^1$H NMR (300 MHz, CDCl$_3$): δ 10.03-9.14 (m, 2H), 4.21-3.39 (m, 4H), 2.20-0.76 (m, 18H). ESMS cacld (C$_{15}$H$_{24}$N$_4$O$_2$S$_2$): 356.13; found: 355 (M–H)$^+$.

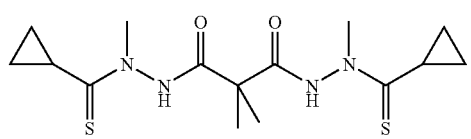

$^1$H NMR (300 MHz, CDCl$_3$): δ 7.57 (br, 2H), 3.72 (s, 6H), 2.95 (m, 6H), 1.96-0.81 (m, 10H). ESMS cacld (C$_{21}$H$_{36}$N$_4$O$_2$S$_2$): 440.13; found: 439 (M–H)$^+$.

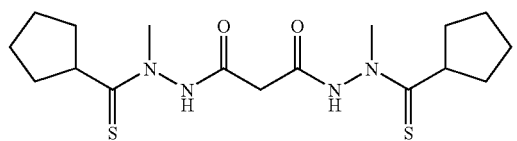

$^1$H NMR (300 MHz, CDCl$_3$): δ 10.09-8.95 (m, 2H), 3.78-3.05 (m, 6H), 2.04-1.22 (m, 20H). ESMS cacld (C$_{17}$H$_{28}$N$_4$O$_2$S$_2$): 384.17; found: 383 (M–H)$^+$.

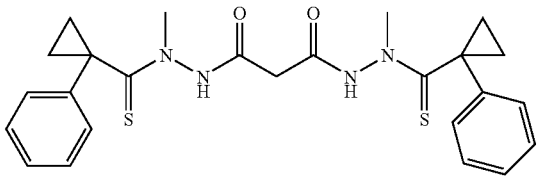

$^1$H NMR (300 MHz, CDCl$_3$): δ 10.09-8.51 (m, 2H), 7.41-7.01 (m, 10H), 3.62-3.02 (m, 6H), 1.78-1.03 (m, 10H). ESMS cacld (C$_{25}$H$_{28}$N$_4$O$_2$S$_2$): 480.17; found: 479 (M–H)$^+$.

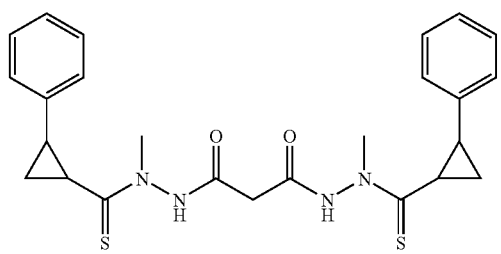

$^1$H NMR (300 MHz, CDCl$_3$): δ 10.09-8.81 (m, 2H), 7.51-7.11 (m, 10H), 3.80-3.06 (m, 6H), 2.92-1.53 (m, 10H). ESMS cacld (C$_{25}$H$_{28}$N$_4$O$_2$S$_2$): 480.17; found: 479 (M−H)$^+$.

Example 15

Compound (1) Demonstrates Multi-Drug Resistant Specific Anti-Cancer Activity In Vitro

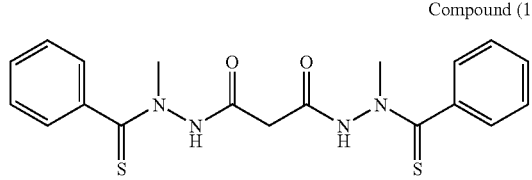

Compound (1)

The in vitro activity of the compounds was assessed in a selected set of human cancer cell lines. Three pairs of tumor cell lines (non-resistant/resistant) were used to identify novel potent antitumor compounds which are capable of overcoming multi-drug resistance.

HL-60, a model of myeloid leukemia, was obtained from ATCC (ATCC CCL-240); and HL60/TX1000 was isolated in vitro by subculturing HL-60 in progressively higher concentration of paclitaxel. HL-60/TX1000 cells over-express mdr-1 mRNA and p-glycoprotein (PCP), as determined by western blot and immunofluorescence labeling with antiPGP antibodies. The cells are cross-resistant to paclitaxel, Vincristine, Adriamycin, Etoposide and Doxorubicin.

MES-SA, a model of uterine sarcoma, is sensitive to a number of chemotherapeutic agents, including Doxorubicin, Dactinomycin, Mitomycin C, paclitaxel and Bleomycin, but resistant to Vinblastine and Cisplatin. MES-SA/DX5 was established in the presence of increasing concentrations of Doxorubicin. The cells express high levels of mdr-1 mRNA and p-glycoprotein and exhibit cross resistance to more than fifteen chemotherapeutic agents including paclitaxel, Etoposide, Mitomycin C, Colchicine, Vinblastine, Dactinomycin, 5-Fluorouracil, Methotrexate and others. Both MES-SA and MES-SA/Dx5 were purchased from ATCC (ATCC CRL-1976 and ATCC CRL-1977, respectively).

Bowes is a melanoma cell line; and Bowes/OV2 is a Vincristine resistant Bowes melanoma cell line.

The cell lines were maintained in RPMI 1640 (GIBCO) supplemented with 10% FCS, 100 units/ml penicillin, 100 ug/ml streptomycin, and 2 mM L-glutamine. The cells were split every third day and diluted to a concentration of 2×110 cells/ml one day before experiment. All experiments were performed on exponentially growing cell culture. Cell densities were 2.5×10$^4$ cells/ml in all experiment except special.

A stock solution of Compound (1), paclitaxel (positive control) and Vincristine (positive control) were prepared by dissolving the compound at a concentration of 1 mM in 100% DMSO. Final concentrations were obtained by diluting the stock solution directly into the tissue culture medium. Cells were incubated with varying concentrations of compounds for 72 hours and the IC$_{50}$ was determined by MTS (i.e. 3-(4.5-dimethylthiazol-2-yl)-2.5-diphenyl tetrazolium bromide) assay. The IC$_{50}$ is the concentration of compound required to inhibit 50% tumor cell growth. The results are shown in Table 1.

TABLE 1

Inhibition of Growth of Multi-Drug Resistant Tumor Cell Lines by Anti-Cancer Agents and Compound (1)

| | IC$_{50}$ (uM) | | | | | |
|---|---|---|---|---|---|---|
| | MES-SA | MES-SA/DX5 | HL-60 | HL-60/TX1000 | Bowes | Bowes/OV2 |
| Paclitaxel | 0.005 | 5 | 0.002 | 5 | 0.005 | 5 |
| Vincristine | 0.004 | 5 | 0.002 | 5 | 0.002 | 5 |
| Compound (1) | 0.05 | 0.005 | 0.4 | 0.05 | 0.2 | 0.01 |

As can be seen from the data in Table 1, paclitaxel and Vincristine demonstrated significantly high anti-cancer activity (IC$_{50}$: 0.002-0.005 uM) aganist normal cancer cell lines (MES-SA, HL-60, Bowes). However, these anti-cancer drugs were significantly less effective (IC$_{50}$: 5 uM) against the MDR cell lines (MES-SA/DX5, HL-60/TX1000, Bowes/OV2). On the other hand, Compound (1) surprisingly showed higher anti-cancer activity against all three MDR cell lines. The specificity were 10 (=0.05/0.005), 8 (=0.4/0.05), and 20 (=0.2/0.01) against MES-SA/DX5, HL60/TX1000, and Bowes/OV2, respectively.

Example 16

Compounds (2)-(18) Demonstrate High Anti-Cancer Activity Against Multi-Drug Resistant MES-SA/DX5 In Vitro The protocol described in Example 15 was used to test Compounds (2)-(18) for investigating inhibitory activity of cancer cell growth of MES-SA/DX5, which is a MDR uterine sarcoma cell line. The results are shown in Table 2, below.

TABLE 2

Inhibition of Growth of the Multi-Drug Resistant Tumor Cell Line MES-SA/DX5 by Compounds (2)-(18).

| Compound | IC$_{50}$ (uM) MES/DX5 |
|---|---|
| Paclitaxel | 5 |
| 2 | 0.005 |
| 3 | 0.05 |
| 4 | 0.005 |
| 5 | 0.05 |
| 6 | 0.005 |
| 7 | 0.01 |
| 8 | 0.005 |
| 9 | 0.005 |
| 10 | 0.005 |
| 11 | 0.005 |
| 12 | 0.005 |
| 13 | 0.05 |
| 14 | 0.01 |
| 15 | 0.005 |
| 16 | 0.05 |
| 17 | 0.005 |
| 18 | 0.01 |

As can be seen from the data in Table 2, Compounds (2)-(18) demonstrated significant anti-cancer activity (IC$_{50}$: 0.05-0.005 uM) against the multi-drug resistant (MDR) cell line MES-SA/DX5, while paclitaxel showed very week anticancer activity (IC$_{50}$:5 uM) against the same MDR cell line.

Example 17

Compound (16) Demonstrates Anti-Cancer Activity Against Multi-Drug Resistant Human Uterine Sarcoma MES/SA-DX5 Tumors in Nude Mice

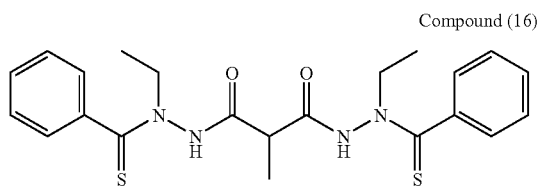

Compound (16)

Procedure

A supplemented media was prepared from 50% DMEM/Dulbecco Modified Eagle Medium (High Glucose), 50% RPMI 1640, 10% FBS/Fetal Bovine Serum (Hybridoma Tested; Sterile Filtered), 1% L-Glutamine, 1% Penicillin-Streptomycin, 1% MEM Sodium Pyruvate and 1% MEM Non-Essential Amino Acids. FBS was obtained from Sigma Chemical Co. and other ingredients were obtained from Invitrogen Life Technologies, USA). The supplemental media was warmed to 37° C. and 50 ml of media was added to a 175 cm$^2$ tissue culture flask.

The cells used in the assay were multi-drug resistant MES-SA/DX-5 Human Uterine Sarcoma cells from the American Type Culture Collection. 1 vial of MES-SA/DX-5 cells from the liquid nitrogen frozen cell stock was removed. The frozen vial of cells was immediately placed into a 37° C. water bath and gently swirled until thawed. The freeze-vial was wiped with 70% ethanol and cells were immediately pipetted into the 175 cm$^2$ tissue culture flask containing supplemented media. The cells were incubated overnight and the media was removed and replaced with fresh supplemented media the next day. The flask was incubated until the cells became about 90% confluent. This took anywhere from 5-7 days.

The flask was washed with 10 ml of sterile room temperature phosphate buffered saline (PBS). The cells were trypsinized by adding 5 ml of warmed Trypsin-EDTA (Invitrogen) to the flask of cells. The cells were then incubated for 2-3 minutes at 37° C. until cells begun to detach from the surface of the flask. An equal volume of supplemented media (5 ml) was added to the flask. All the cells were collected into 50 ml tube, and centrifuged at 1000 RPM for 5 minutes at 20° C. The supernatant was aspirated and the cell pellet was resuspended in 10 ml of supplemented media and the cells were counted. 1-3 million cells/flask were seeded into 5-7 tissue culture flasks (175 cm$^2$). Each flask contained 50 ml of supplemented media. The flasks were incubated until about 90% confluent. The passaging of the cells was repeated until enough cells had been grown for tumor implantation.

The above procedure for trypsinizing and centrifuging the cells were followed. The supernatant was aspirated and the cell pellet was resuspended in 10 ml of sterile PBS and the cells were counted. The cells were centrifuged and then resuspended with appropriate volume of sterile PBS for injection of correct number of cells needed for tumor implantation. 100 million cells were suspended with 2.0 ml of sterile PBS to a final concentration of 50 million cells/ml in order to inject 5 million cells in 0.1 ml/mouse.

Five million MES-SA/DX5 cells were injected subcutaneously into the flan (lateral side) of female CB. 17/SCID mice (Age 6-7 wks). These mice were obtained from Taconic, Germantown, N.Y. (Nomenclature: C.B-Igh-1$^b$IcrTac-Prkdc-$^{scid}$) CB.17/SCID (FOX CHASE SCID) and are homozygous for the autosomal recessive scid (severe combined immuno-deficient) gene and lack both T and B cells due to a defect in V(D)J recombination. Therefore, they easily accept foreign tissue transplants. These tumors were allowed to grow until they reached a size of about 200-300 mm$^3$ before they were excised and prepared as a single cell suspension. These cells were then seeded into tissue culture flasks. The cells went through two passages in vitro before the tumor cells were collected.

Mice (CD-1 nu/nu) were obtained from Charles River Laboratories: nomenclature: Crl:CD-1-nuBR, Age: 6-8 weeks. The mice were allowed to acclimate for 1 week prior to their being used in an experimental procedure.

Implantation of the MES-SA/DX5 tumor cell suspension took place in the lateral flank of the female CD-1 nu/nu mouse. Five million tumor cells in 0.1 mL of PBS were injected using a 27G (½ inch) needle. MES-SA/DX5 tumors developed after 2-3 weeks after implantation.

Compound stock solutions were prepared by dissolving the compound in cell-culture-grade DMSO (dimethyl sulfoxide) at the desired concentration. This stock solution in DMSO was sonicated in an ultrasonic water bath until all the powder dissolved.

The Formulation Solvent was prepared as follows: 20% of Cremophore RH40 (Polyoxyl 40 Hydrogenated Castor Oil obtained from BASF corp.) in water was prepared by first heating 100% Cremophore RH40 in a water bath at 50-60° C. until it liquefied and became clear. 10 ml of the 100% Cremophore RH40 aliquoted into a conical centrifuge tube containing 40 ml of sterile water (1:5 dilution of Cremophore RH40). The 20% Cremophore RH40 solution was reheated until it became clear again, and mixed by inverting the tube several times. This 20% Cremophore RH40 solution was stored at room temperature, and was kept for up to 3 months.

Preparation of Dosing Solution for Compound Administration: The compound stock solution was diluted 1:10 with 20% Cremophore RH40:1) 2.0 ml of 10 mg/ml dosing solution of Compound (16) was prepared by diluting 100 mg/ml Compound Stock solution with 1.8 ml of 20% Cremophore RH40 water solution. The final formulation for the dosing solution was 10% DMSO, 18% Cremophore RH40 and 72% water.

The Dosing Solution (Dosing Volume: 0.01 ml/gram=10 ml/kg) was injected intravenously into the mice bearing MES-SA/DX-5 human sarcoma tumor.

Protocol

| Group | Compounds | (Dose) |
|---|---|---|
| 1 | Vehicle Only | |
| 2 | Compound (16) | (15 mg/kg) |

Figure 2:
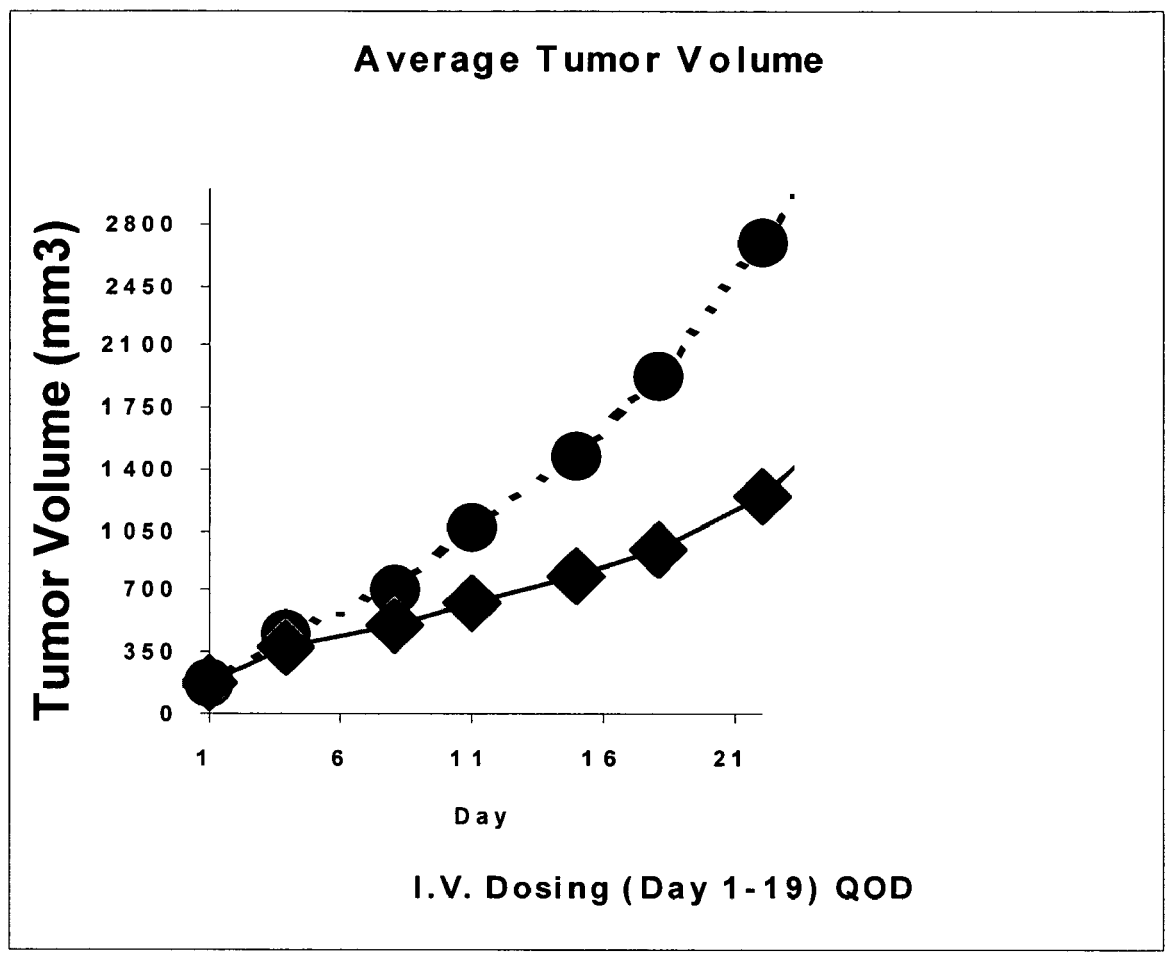
FIG. 2 is a graph showing the average tumor size in nude mice (CD-1 nu/nu) over time after having been treated with vehicle (●) or Compound (16) (◆). The tumor volume is in mm$^3$ and the time is in days after having begun treatment. The tumors are from the multi-drug resistant human uterine sarcoma MES-SA/DX5.

Dosing Schedule: 3 times a week (Monday, Wednesday, Friday) for 3 weeks 5 mice were used for each group Results FIG. 2 shows the effects of Compound (16) on inhibiting tumor growth of MES/SA-DX5. As can be seen from FIG. 2, Compound (16) significantly inhibits the tumor growth without any obvious toxicity such as body weight suppression and behavior changes.

Example 18

Combination Treatment of Compound (1) and Epothilone D Demonstrated Anti-tumor Activity Against Human Breast Carcinoma MDA-435 in Nude Mice Procedure A supplemented media was prepared from 50% DMEM/ Dulbecco Modified Eagle Medium (High Glucose), 50% RPMI 1640, 10% FBS/Fetal Bovine Serum (Hybridoma Tested; Sterile Filtered), 1% L-Glutamine, 1% Penicillin-Streptomycin, 1% MEM Sodium Pyruvate and 1% MEM Non-Essential Amino Acids. FBS was obtained from Sigma Chemical Co. and other ingredients were obtained from Invitrogen Life Technologies, USA). The supplemental media was warmed to 37° C. and 50 ml of media was added to a 175 cm² tissue culture flask.

The cells used in the assay were MDA-435 Human Breast Carcinoma from the American Type Culture Collection. 1 vial of MDA-435 cells from the liquid nitrogen frozen cell stock was removed. The frozen vial of cells was immediately placed into a 37° C. water bath and gently swirled until thawed. The freeze-vial was wiped with 70% ethanol and cells were immediately pipetted into the 175 cm² tissue culture flask containing supplemented media. The cells were incubated overnight and the media was removed and replaced with fresh supplemented media the next day. The flask was incubated until flask became about 90% confluent. This took anywhere from 5-7 days.

The flask was washed with 10 ml of sterile room temperature phosphate buffered saline (PBS). The cells were trypsinized by adding 5 ml of warmed Trypsin-EDTA (Invitrogen) to the flask of cells. The cells were then incubated for 2-3 minutes at 37° C. until cells begun to detach from the surface of the flask. An equal volume of supplemented media (5 ml) was added to the flask. All the cells were collected into 50 ml tube, and centrifuged at 1000 RPM for 5 minutes at 20° C. The supernatant was aspirated and the cell pellet was resuspended in 10 ml of supplemented media and the cells were counted. 1-3 million cells/flask were seeded into 5-7 tissue culture flasks (175 cm²). Each flask contained 50 ml of supplemented media. The flasks were incubated until about 90% confluent. The passaging of the cells was repeated until enough cells have been grown for tumor implantation.

The above procedure for trypsinizing and centrifuging the cells were followed. The supernatant was aspirated and the cell pellet was resuspended in 10 ml of sterile PBS and the cells were counted. The cells were centrifuged and then resuspended with appropriate volume of sterile PBS for injection of correct number of cells needed for tumor implantation. In the case of MDA-435, 100 million cells were suspended with 2.0 ml of sterile PBS to a final concentration of 50 million cells/ml in order to inject 5 million cells in 0.1 ml/mouse. Mice (CD-1 nu/nu) were obtained from Charles River Laboratories: nomenclature: Crl:CD-1-nuBR, Age: 6-8 weeks. The mice were allowed to acclimate for 1 week prior to their being used in an experimental procedure.

Implantation of the MDA-435 tumor cell suspension took place into the corpus adiposum of the female CD-1 nu/nu mouse. This fat body is located in the ventral abdominal viscera of the mouse. Tumor cells were implanted subsutaneously into the fat body located in the right quadrant of the abdomen at the juncture of the os coxae (pelvic bone) and the os femoris (femur). 5 million MDA-435 cells in 0.1 ml of sterile PBS were injected using 27 G (½ inch) needle. MDA-435 tumors developed 2-3 weeks after implantation.

Compound stock solutions were prepared by dissolving the compound in cell-culture-grade DMSO (dimethyl sulfoxide) at the desired concentration. This stock solution in DMSO was sonicated in an ultrasonic water bath until all the powder dissolved.

The Formulation Solvent was prepared as follows: 20% of Cremophore RH40 (Polyoxyl 40 Hydrogenated Castor Oil obtained from BASF corp.) in water was prepared by first heating 100% Cremophore RH40 in a water bath at 50-60° C. until it liquefied and became clear. 10 ml of the 100% Cremophore RH40 aliquoted into a conical centrifuge tube containing 40 ml of sterile water (1:5 dilution of Cremophore RH40). The 20% Cremophore RH40 solution was reheated until it became clear again, and mixed by inverting the tube several times. This 20% Cremophore RH40 solution was stored at room temperature, and was kept for up to 3 months.

Preparation of Dosing Solution for Compound Administration: The compound stock solution was diluted 1:10 with 20% Cremophore RH40:1) 2.0 ml of 10 mg/ml dosing solution of Compound (1) was prepared by diluting 100 mg/ml Compound Stock solution with 1.8 ml of 20% Cremophore RH40 water solution; and 2) a dosing solution comprising 2.0 ml of 1 mg/ml of Epothilone D and 5 mg/ml of Compound (1) was obtained by mixing 0.1 ml of Compound (1) DMSO stock solution (50 mg/ml) and 0.1 ml of Epothilone D DMSO stock solution (10 mg/ml) and diluting with 1.8 ml of 20% Cremophore RH40 water solution. The final formulation for the dosing solution was 10% DMSO, 18% Cremophore RH40 and 72% water.

The Dosing Solution (Dosing Volume: 0.01 ml/gram=10 ml/kg) was injected intravenously into the mice bearing MDA-435 human breast tumor.

Protocol

| Group | Compounds | (Dose) |
|---|---|---|
| 1 | Vehicle Only | |
| 2 | Epothilone D | (5 mg/kg) |
| 3 | Epothilone D | (5 mg/kg) + Compound (1) (50 mg/kg) |

Figure 3:
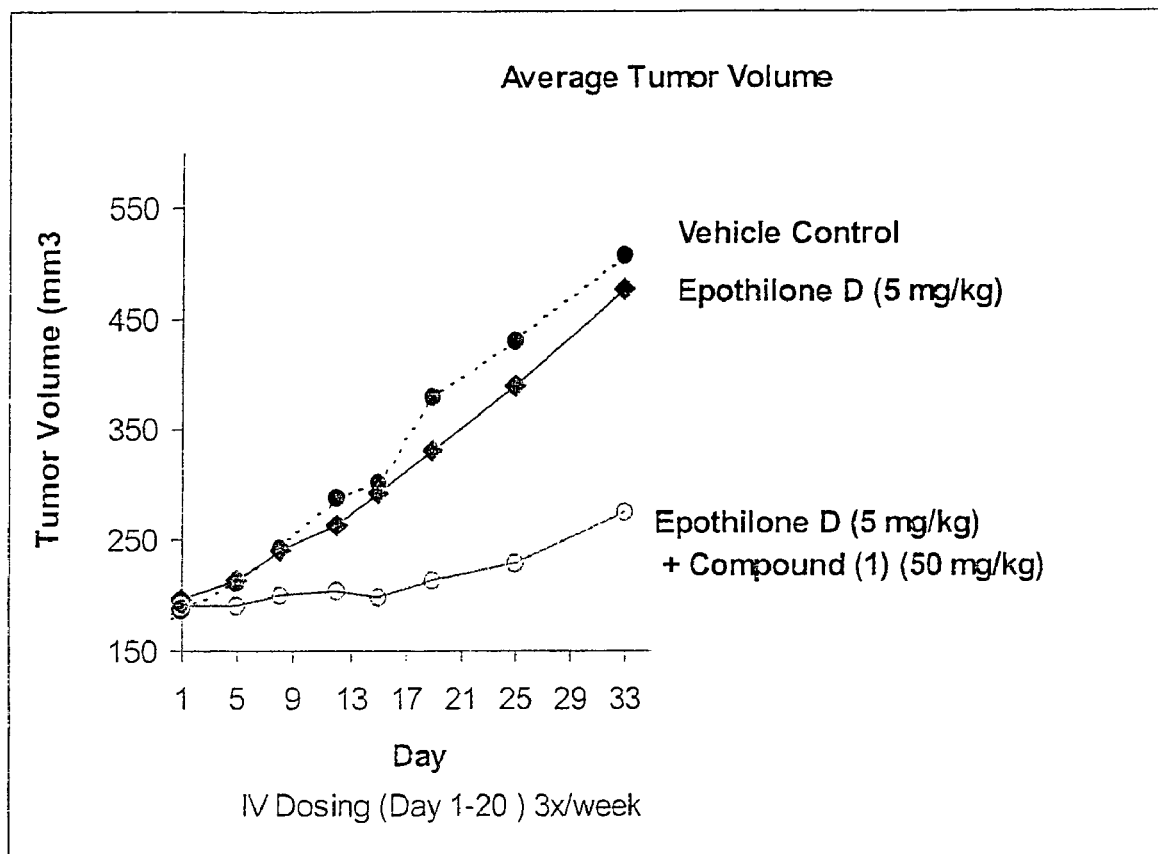
FIG. 3 is a graph showing the average tumor volume in milliliters over time (in days) in nude mice (CD-1 nu/nu) treated with vehicle (●); Epothilone D (5 mg/kg) (◆); and Compound (1) (50 mg/kg) and Epothilone (5 mg/kg) (○). The tumors were generated from the human breast tumor cell line MDA-435.
Figure 4:
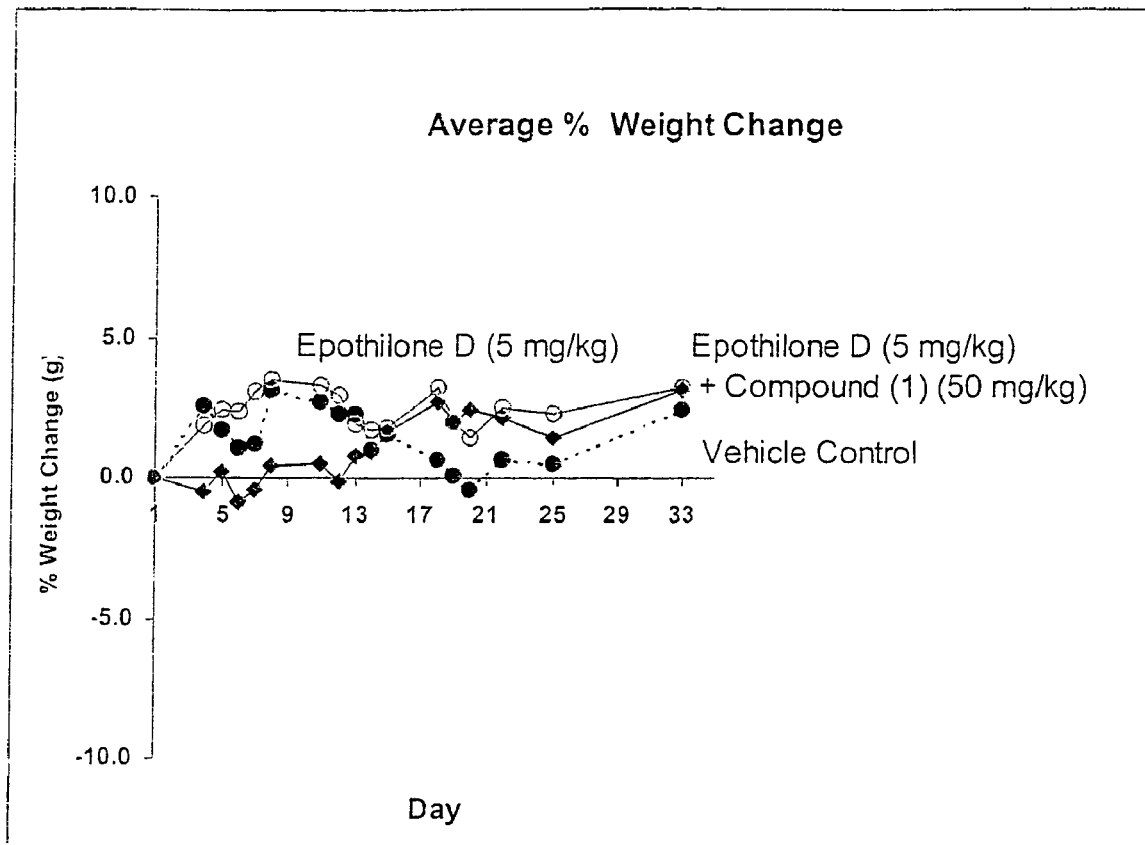
FIG. 4 is a graph showing the average percent weight change in nude mice (CD-1 nu/nu) over time after having been treated with vehicle ( ); Epothilone D (5 mg/kg) (◆); and Compound (1) (50 mg/kg) and Epothilone (5 mg/kg) (○). The mice were being treated for tumors generated tumors generated from the human breast tumor cell line MDA-435.

Dosing Schedule: 3 times a week (Monday, Wednesday, Friday) for 3 weeks. 5 mice were used for each group Results FIG. 3 shows the effects of Compound (1) on enhancing anti-tumor activity of Epothilone D. As can be seen from FIG. 3, Compound (1) significantly enhanced anti-tumor activity of Epothilone D on human breast tumor MDA-435 in nude mice. FIG. 4 shows the effects of treatment of Epothilone D and the combination of Compound (1) and Epothilone D on the body weight of nude mice bearing MDA-435 human breast tumor. As can be seen from FIG. 4, Compound (1) enhanced anti-tumor activity of Epothilone D without increasing toxicity.

Example 19

Compound (1) has Anti-Leukemia Activity In Vitro

The in vitro activity of the compounds was determined in a selected set of human leukemia cell lines. CEM (T-cell leukemia), Jurkat (T-cell leukemia), K562 (chronic myelocyte), THP-1 (monocyte), SB (B-cell leukemia), U937 (lymphoma)

were purchased from ATCC. H2 leukemia cell line was a gift from Harvard Medical School.

The cell lines were maintained in RPMI1640 (GIBCO) supplemented with 10% FCS, 100 units/ml penicillin, 100 ug/ml streptomycin, and 2 mM L-glutamine. The cells were split every third day and diluted to a concentration of 2×10⁵ cells/mL one day before experiment. All experiments were performed on exponentially growing cell culture. Cell densities were 2.5×10⁴ cells/mL in all experiments.

Compound (1) was prepared by dissolving the compound at a concentration of 10 mM in 100% DMSO. Final concentrations 10, 1, 0.1, 0.01 and 0.001 µM were obtained by diluting the stock solution directly into the tissue culture medium. Cells were incubated with varying concentrations of compounds for 72 hours and the IC50 was determined by MTS (i.e. 3-(4.5.-dimethylthiazol-2-yl)-2.5-diphenyl tetrazolium bromide) assay. IC50 is the concentration of compound required to inhibit 50% tumor cell growth. Table 3 shows the in vitro IC50 (ÿM) cytotoxicity results of Compound (1) versus vincristin and paclitaxel.

TABLE 3

In vitro Cytotoxicity (IC50, µM) of Compound (1) versus Vincristin and Taxol

| Cell Line | Species | Cell type | Compound (1) | Vincristin | Taxol |
|---|---|---|---|---|---|
| 39SK | Human | normal fibroblast | >10 | 1 | 1 |
| Jurkat | Human | T cell leukemia | 0.005 | 0.001 | 0.001 |
| CEM | Human | T cell leukemia | 0.01 | 0.005 | 0.01 |
| K-562 | Human | chronic myelocyte | 0.05 | 0.005 | 0.005 |
| THP-1 | Human | monocyte | 0.01 | 0.005 | 0.005 |
| U937 | Human | lymphoma | 0.05 | 0.005 | 0.005 |
| SB | Human | B cell leukemia | 0.005 | 0.001 | 0.001 |
| H2 | Human | Leukemia | 0.005 | 0.005 | 0.005 |

Example 20

Compound 1 Inhibits Human T-Cell Leukemia Growth (CEM Cell Line)

Human T-cell leukemia cell line, CEM, was obtained from American Type Culture Collection. Eight-week old female SCID mice were purchased from Charles Rive Laboratories (Wilmington, Mass.). FITC conjugated anti-human HLA-A, B,C was obtained from BD ParMingen (Cat # 32294x). ACK lysing buffer was obtained from BioWhittaker.

CEM cells (1×10⁶ cells in 100 µl saline) were implanted intravenously into female SCID mice through the tail vein. Vehicle and Compound (1) (25 mg/kg) were administrated intraperitoneally twice a day and total for 3 weeks. After three weeks treatment, bloods were taken from mouse retro-orbital sinus at 33. Red blood cells were partially lyzed with ACK lysing buffer. The cells were stained with FITC conjugated anti-human HLA-A,B,C antibody for one hour at 4° C. FACS analysis was performed to quantitate the amount of CEM cells in the blood. White blood cells were gated for FACS analysis. The results showed that about 37.7%, 4.6% and 1.07% of CEM cells were detected in the white blood cells from vehicle treated, Compound (1) treated, and untreated group respectively (Table 4).

TABLE 4

Summary of CEM cell quantitation at day 33

| Treatment | % circulating leukemia cells | % relative to vehicle |
|---|---|---|
| Vehicle (n = 5) | 37.7 | 100 |
| Compound (1) (n = 5) | 4.6 | 12.2 |
| Untreated mice (n = 2) | 1.07 | 2.8 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a subject with a multi-drug resistant leukemia, said method comprising administering to the subject an effective amount of a compound represented by the following structural formula:

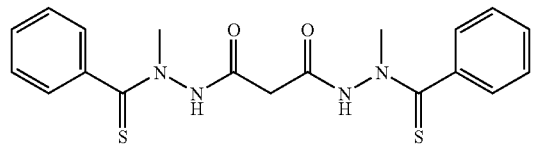

or a pharmaceutically acceptable salt thereof.

2. The method of claim 1, wherein the method further comprises administering to the subject an effective amount of paclitaxel or docetaxol.

3. A method of treating a subject with a multi-drug resistant uterine sarcoma, said method comprising administering to the subject an effective amount of a compound represented by the following structural formula:

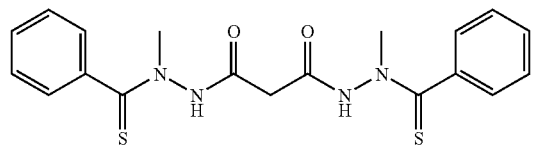

or a pharmaceutically acceptable salt thereof.

4. The method of claim 3, wherein the method further comprises administering to the subject an effective amount of paclitaxel or docetaxol.

5. A method of treating a subject with a multi-drug resistant melanoma, said method comprising administering to the subject an effective amount of a compound represented by the following structural formula:

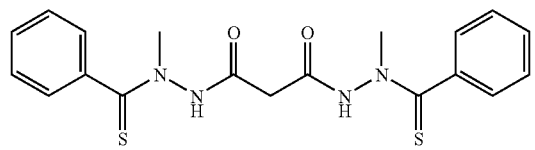

or a pharmaceutically acceptable salt thereof.

6. The method of claim 5, wherein the method further comprises administering to the subject an effective amount of paclitaxel or docetaxol.

* * * * *